(12) United States Patent
Liao et al.

(10) Patent No.: US 10,266,831 B2
(45) Date of Patent: *Apr. 23, 2019

(54) RECOMBINANT MICROORGANISMS HAVING A METHANOL ELONGATION CYCLE (MEC)

(71) Applicant: The Regents of the University of California, Oakland, CA (US)

(72) Inventors: James C. Liao, Los Angeles, CA (US); Igor Bogorad, Tarzana, CA (US)

(73) Assignee: The Regents of the University of California, Oakland, CA (US)

( * ) Notice: Subject to any disclaimer, the term of this patent is extended or adjusted under 35 U.S.C. 154(b) by 289 days.

This patent is subject to a terminal disclaimer.

(21) Appl. No.: 15/376,489

(22) Filed: Dec. 12, 2016

(65) Prior Publication Data

US 2017/0166902 A1 Jun. 15, 2017

Related U.S. Application Data

(63) Continuation of application No. 14/211,415, filed on Mar. 14, 2014, now Pat. No. 9,518,278.

(60) Provisional application No. 61/785,143, filed on Mar. 14, 2013.

(51) Int. Cl.
*C12N 15/52* (2006.01)
*C12N 15/70* (2006.01)
*C12P 9/00* (2006.01)
*C12N 9/88* (2006.01)
*C12N 15/63* (2006.01)

(52) U.S. Cl.
CPC .............. *C12N 15/52* (2013.01); *C12N 9/88* (2013.01); *C12N 15/63* (2013.01); *C12N 15/70* (2013.01); *C12P 9/00* (2013.01); *C12Y 401/02009* (2013.01); *C12Y 401/02022* (2013.01); *Y02P 20/52* (2015.11)

(58) Field of Classification Search
None
See application file for complete search history.

(56) References Cited

U.S. PATENT DOCUMENTS

2006/0040365 A1* 2/2006 Kozlov ................... C12N 9/88
435/106

* cited by examiner

*Primary Examiner* — Manjunath N Rao
*Assistant Examiner* — Jae W Lee
(74) *Attorney, Agent, or Firm* — Gavrilovich, Dodd & Lindsey LLP

(57) ABSTRACT

Provided are microorganisms that catalyze the synthesis of chemicals and biochemicals from a methanol, methane and/or formaldehyde. Also provided are methods of generating such organisms and methods of synthesizing chemicals and biochemicals using such organisms.

10 Claims, 7 Drawing Sheets

Specification includes a Sequence Listing.

FIGURE 1A-D

```
F/Xpk (Bifidobacterium adolescentis) (SEQ ID NO:1)
ATGACGAGTCCTGTTATTGGCACCCCTTGGAAGAAGCTGAACGCTCCGGTTTCCGAGGAAGCTATCGAAGGCGT
GGATAAGTACTGGCGCGCAGCCAACTACCTCTCCATCGGCCAGATCTATCTGCGTAGCAACCCGCTGATGAAGG
AGCCTTTCACCCGCGAAGACGTCAAGCACCGTCTGGTCGGTCACTGGGGCACCACCCGGGCCTGAACTTCCTC
ATCGGCCACATCAACCGTCTCATTGCTGATCACCAGCAGAACACTGTGATCATCATGGGCCCGGGCCACGGCGG
CCCGGCTGGTACCGCTCAGTCCTACCTGGACGGCACCTACACCGAGTACTTCCCGAACATCACCAAGGATGAGG
CTGGCCTGCAGAAGTTCTTCCGCCAGTTCTCCTACCCGGGGTGGCATCCCGTCCCACTACGCTCCGGAGACCCCG
GGCTCCATCCACGAAGGCGGCGAGCTGGGTTACGCCCTGTCCCACGCCTACGGCGCTGTGATGAACAACCCGAG
CCTGTTCGTCCCGGCCATCGTCGGCGACGGTGAAGCTGAGACCGGCCCGCTGGCCACCGGCTGGCAGTCCAACA
AGCTCATCAACCCGCGCACCGACGGTATCGTGCTGCCGATCCTGCACCTCAACGGCTACAAGATCGCCAACCCG
ACCATCCTGTCCCGCATCTCCGACGAAGAGCTCCACGAGTTCTTCCACGGCATGGGCTATGAGCCGTACGAGTT
CGTCGCTGGCTTCGACAACGAGGATCACCTGTCGATCCACCGTCGTTTCGCCGAGCTGTTCGAGACCGTCTTCG
ACGAGATCTGCGACATCAAGGCCGCCGCTCAGACCGACGACATGACTCGTCCGTTCTACCCGATGATCATCTTC
CGTACCCCGAAGGGCTGGACCTGCCCGAAGTTCATCGACGGCAAGAAGACCGAGGGCTCCTGGCGTTCCCACCA
GGTGCCGCTGGCTTCCGCCCGCGATACCGAGGCCCACTTCGAGGTCCTCAAGAACTGGCTCGAGTCCTACAAGC
CGGAAGAGCTGTTCGACGAGAACGGCGCCGTGAAGCCGGAAGTCACCGCCTTCATGCCGACCGGCGAACTGCGC
ATCGGTGAGAACCCGAACGCCAACGGTGGCCGCATCCGCGAAGAGCTGAAGCTGCCGAAGCTGGAAGACTACGA
GGTCAAGGAAGTCGCCGAGTACGGCCACGGCTGGGGCCAGCTCGAGGCCACCCGTCGTCTGGGCGTCTACACCC
GCGACATCATCAAGAACAACCCGGACTCCTTCCGTATCTTCGGACCGGATGAGACCGCTTCCAACCGTCTGCAG
GCCGCTTACGACGTCACCAACAAGCAGTGGGACGGCCGGCTACCTGTCCGCTCAGGTCGACGAGCACATGGCTGT
CACCGGCCAGGTCACCGAGCAGCTTTCCGAGCACCAGATGGAAGGCTTCCTCGAGGGCTACCTGCTGACCGGCC
GTCACGGCATCTGGAGCTCCTATGAGTCCTTCGTGCACGTGATCGACTCCATGCTGAACCAGCACGCCAAGTGG
CTCGAGGCTACCGTCCGCGAGATTCCGTGGCGCAAGCCGATCTCCTCCATGAACCTGCTCGTCTCCTCCCACGT
GTGGCGTCAGGATCACAACGGCTTCTCCCACCAGGATCCGGGTGTCACCTCCGTCCTGCTGAACAAGTGCTTCA
ACAACGATCACGTGATCGGCATCTACTTCCCGGTGGATTCCAACATGCTGCTCGCTGTGGCTGAGAAGTGCTAC
AAGTCCACCAACAAGATCAACGCCATCATCGCCGGCAAGCAGCCGGCCGCCACCTGGCTGACCCTGGACGAAGC
TCGCGCCGAGCTCGAGAAGGGTGCTGCCGAGTGGAAGTGGGCTTCCAACGTGAAGTCCAACGATGAGGCTCAGA
TCGTGCTCGCCGCCACCGGTGATGTTCCGACTCAGGAAATCATGGCCGCTGCCGACAAGCTGGACGCCATGGGC
ATCAAGTTCAAGGTCGTCAACGTGGTTGACCTGGTCAAGCTGCAGTCCGCCAAGGAGAACAACGAGGCCCTCTC
CGATGAGGAGTTCGCTGAGCTGTTCACCGAGGACAAGCCGGTCCTGTTCGCTTACCACTCCTATGCCCGCGATG
TGCGTGGTCTGATCTACGATCGCCCGAACCACGACAACTTCAACGTTCACGGCTACGAGGAGCAGGGCTCCACC
ACCACCCCGTACGACATGTTCGCGTGAACAACATCGATCGCTACGAGCTCCAGGCTGAAGCTCTGCGCATGAT
TGACGCTGACAAGTACGCCGACAAGATCAACGAGCTCGAGGCCTTCCGTCAGGAAGCCTTCCAGTTCGCTGTCG
ACAACGGCTACGATCACCCGGATTACACCGACTGGGTCTACTCCGGTGTCAACACCAACAAGCAGGGTGCTATC
TCCGCTACCGCCGCAACCGCTGGCGATAACGAGTGA
```

FIGURE 6

```
Rpe (E. coli) (SEQ ID NO:5)
ATGAAACAGTATTTGATTGCCCCCTCAATTCTGTCGGCTGATTTTGCCCGCCTGGGTGAAGATACCGCAAAAGC
CCTGGCAGCTGGCGCTGATGTCGTGCATTTTGACGTCATGGATAACCACTATGTTCCCAATCTGACGATTGGGC
CAATGGTGCTGAAATCCTTGCGTAACTATGGCATTACCGCCCCTATCGACGTACACCTGATGGTGAAACCCGTC
GATCGCATTGTGCCTGATTTCGCTGCCGCTGGTGCCAGCATCATTACCTTTCATCCAGAAGCCTCCGAGCATGT
TGACCGCACGCTGCAACTGATTAAAGAAAATGGCTGTAAAGCGGGTCTGGTATTTAACCCGGCGACACCTCTGA
GCTATCTGGATTACGTGATGGATAAGCTGGATGTGATCCTGCTGATGTCCGTCAACCCTGGTTTCGGCGGTCAG
TCTTTCATTCCTCAAACACTGGATAAACTGCGCGAAGTACGTCGCCGTATCGACGAGTCTGGCTTTGACATTCG
ACTAGAAGTGGACGGTGGCGTGAAGGTGAACAACATTGGCGAAATCGCTGCGGCGGGCGCGGATATGTTCGTCG
CCGGTTCGGCAATCTTCGACCAGCCAGACTACAAAAAAGTCATTGATGAAATGCGCAGTGAACTGGCAAAGGTA
AGTCATGAATAA
```

FIGURE 7

RpiA (*E. coli*) (SEQ ID NO:7)
ATGACGCAGGATGAATTGAAAAAAGCAGTAGGATGGGCGGCACTTCAGTATGTTCAGCCCGGCACCATTGTTGG
TGTAGGTACAGGTTCCACCGCCGCACACTTTATTGACGCGCTCGGTACAATGAAAGGCCAGATTGAAGGGGCCG
TTTCCAGTTCAGATGCTTCCACTGAAAAACTGAAAAGCCTCGGCATTCACGTTTTTGATCTCAACGAAGTCGAC
AGCCTTGGCATCTACGTTGATGGCGCAGATGAAATCAACGGCCACATGCAAATGATCAAAGGCGGCGGCGCGGC
GCTGACCCGTGAAAAAATCATTGCTTCGGTTGCAGAAAAATTTATCTGTATTGCAGACGCTTCCAAGCAGGTTG
ATATTCTGGGTAAATTCCCGCTGCCAGTAGAAGTTATCCCGATGGCACGTAGTGCAGTGGCGCGTCAGCTGGTG
AAACTGGGCGGTCGTCCGGAATACCGTCAGGGCGTGGTGACCGATAATGGCAACGTGATCCTCGACGTCCACGG
CATGGAAATCCTTGACCCGATAGCGATGGAAAACGCCATAAATGCGATTCCTGGCGTGGTGACTGTTGGCTTGT
TTGCTAACCGTGGCGCGGACGTTGCGCTGATTGGCACACCTGACGGTGTCAAAACCATTGTGAAATGA
FIGURE 8

TalB (*E. coli*) (SEQ ID NO:9)
ATGACGGACAAATTGACCTCCCTTCGTCAGTACACCACCGTAGTGGCCGACACTGGGGACATCGCGGCAATGAA
GCTGTATCAACCGCAGGATGCCACAACCAACCCTTCTCTCATTCTTAACGCAGCGCAGATTCCGGAATACCGTA
AGTTGATTGATGATGCTGTCGCCTGGGCGAAACAGCAGAGCAACGATCGCGCGCAGCAGATCGTGGACGCGACC
GACAAACTGGCAGTAAATATTGGTCTGGAAATCCTGAAACTGGTTCCGGGCCGTATCTCAACTGAAGTTGATGC
GCGTCTTTCCTATGACACCGAAGCGTCAATTGCGAAAGCAAAACGCCTGATCAAACTCTACAACGATGCTGGTA
TTAGCAACGATCGTATTCTGATCAAACTGGCTTCTACCTGGCAGGGTATCCGTGCTGCAGAACAGCTGGAAAAA
GAAGGCATCAACTGTAACCTGACCCTGCTGTTCTCCTTCGCTCAGGCTCGTGCTTGTGCGGAAGCGGGCGTGTT
CCTGATCTCGCCGTTTGTTGGCCGTATTCTTGACTGGTACAAAGCGAATACCGATAAGAAAGAGTACGCTCCGG
CAGAAGATCCGGGCGTGGTTTCTGTATCTGAAATCTACCAGTACTACAAAGAGCACGGTTATGAAACCGTGGTT
ATGGGCGCAAGCTTCCGTAACATCGGCGAAATTCTGGAACTGGCAGGCTGCGACCGTCTGACCATCGCACCGGC
ACTGCTGAAAGAGCTGGCGGAGAGCGAAGGGGCTATCGAACGTAAACTGTCTTACACCGGCGAAGTGAAAGCGC
GTCCGGCGCGTATCACTGAGTCCGAGTTCCTGTGGCAGCACAACCAGGATCCAATGGCAGTAGATAAACTGGCG
GAAGGTATCCGTAAGTTTGCTATTGACCAGGAAAAACTGGAAAAAATGATCGGCGATCTGCTGTAA
FIGURE 9

TktA (*E. coli*) (SEQ ID NO:11)
ATGTCCTCACGTAAAGAGCTTGCCAATGCTATTCGTGCGCTGAGCATGGACGCAGTACAGAAAGCCAAATCCGG
TCACCCGGGTGCCCCTATGGGTATGGCTGACATTGCCGAAGTCCTGTGGCGTGATTTCCTGAAACACAACCCGC
AGAATCCGTCCTGGGCTGACCGTGACCGCTTCGTGCTGTCCAACGGCCACGGCTCCATGCTGATCTACAGCCTG
CTGCACCTCACCGGTTACGATCTGCCGATGGAAGAACTGAAAAACTTCCGTCAGCTGCACTCTAAAACTCCGGG
TCACCCGGAAGTGGGTTACACCGCTGGTGTGGAAACCACCACCGGCCCGCTGGGTCAGGGTATTGCCAACGCAG
TCGGTATGGCGATTGCAGAAAAAACGCTGGCGGCGCAGTTTAACCGTCCGGGCCACGACATTGTCGACCACTAC
ACCTACGCCTTCATGGGCGACGGCTGCATGATGGAAGGCATCTCCCACGAAGTTTGCTCTCTGGCGGGTACGCT
GAAGCTGGGTAAACTGATTGCATTCTACGATGACAACGGTATTTCTATCGATGGTCACGTTGAAGGCTGGTTCA
CCGACGACACCGCAATGCGTTTCGAAGCTTACGGCTGGCACGTTATTCGCGACATCGACGGTCATGACGCGGCA
TCTATCAAACGCGCAGTAGAAGAAGCGCGCGCAGTGACTGACAAACCTTCCCTGCTGATGTGCAAAACCATCAT
CGGTTTCGGTTCCCCGAACAAAGCCGGTACCCACGACTCCCACGGTGCGCCGCTGGGCGACGCTGAAATTGCCC
TGACCCGCGAACAACTGGGCTGGAAATATGCGCCGTTCGAAATCCCGTCTGAAATCTATGCTCAGTGGGATGCG
AAAGAAGCAGGCCAGGCGAAAGAATCCGCATGGAACGAGAAATTCGCTGCTTACGCGAAAGCTTATCCGCAGGA
AGCCGCTGAATTTACCCGCCGTATGAAAGGCGAAATGCCGTCTGACTTCGACGCTAAAGCGAAAGAGTTCATCG
CTAAACTGCAGGCTAATCCGGCGAAAATCGCCAGCCGTAAAGCGTCTCAGAATGCTATCGAAGCGTTCGGTCCG
CTGTTGCCGGAATTCCTCGGCGGTTCTGCTGACCTGGCGCCGTCTAACCTGACCCTGTGGTCTGGTTCTAAAGC
AATCAACGAAGATGCTGCGGGTAACTACATCCACTACGGTGTTCGCGAGTTCGGTATGACCGCGATTGCTAACG
GTATCTCCCTGCACGGTGGCTTCCTGCCGTACACCTCCACCTTCCTGATGTTCGTGGAATACGCACGTAACGCC
GTACGTATGGCTGCGCTGATGAAACAGCGTCAGGTGATGGTTTACACCCACGACTCCATCGGTCTGGGCGAAGA
CGGCCCGACTCACCAGCCGGTTGAGCAGGTCGCTTCTCTGCGCGTAACCCCGAACATGTCTACATGGCGTCCGT
GTGACCAGGTTGAATCCGCGGTCGCGTGGAAATACGGTGTTGAGCGTCAGGACGGCCCGACCGCACTGATCCTC
TCCCGTCAGAACCTGGCGCAGCAGGAACGAACTGAAGAGCAACTGGCAAACATCGCGCGCGGTGGTTATGTGCT
GAAAGACTCGGCTCAGCCGGAACTGATTTTCATCGCTACCGGTTCAGAAGTTGAACTGGCTGTTGCTGCCT
ACGAAAAACTGACTGCCGAAGGCGTGAAAGCGCGCGTGGTGTCCATGCCGTCTACCGACGCATTTGACAAGCAG
GATGCTGCTTACCGTGAATCCGTACTGCCGAAAGCGGTTACTGCACGCGTTGCTGTAGAAGCGGGTATTGCTGA
CTACTGGTACAAGTATGTTGGCCTGAACGGTGCTATCGTCGGTATGACCACCTTCGGTGAATCTGCTCCGGCAG
AGCTGCTGTTTGAAGAGTTCGGCTTCACTGTTGATAACGTTGTTGCGAAAGCAAAAGAACTGCTGTAA
FIGURE 10

SEQUENCE LISTING

```
<160> NUMBER OF SEQ ID NOS: 20

<210> SEQ ID NO 1
<211> LENGTH: 2478
<212> TYPE: DNA
<213> ORGANISM: Bifidobacterium adolescentis
<220> FEATURE:
<221> NAME/KEY: CDS
<222> LOCATION: (1)..(2478)

<400> SEQUENCE: 1 atg acg agt cct gtt att ggc acc cct tgg aag aag ctg aac gct ccg     48
Met Thr Ser Pro Val Ile Gly Thr Pro Trp Lys Lys Leu Asn Ala Pro
1               5                   10                  15
```

```
gtt tcc gag gaa gct atc gaa ggc gtg gat aag tac tgg cgc gca gcc      96
Val Ser Glu Glu Ala Ile Glu Gly Val Asp Lys Tyr Trp Arg Ala Ala
        20                  25                  30 aac tac ctc tcc atc ggc cag atc tat ctg cgt agc aac ccg ctg atg     144
Asn Tyr Leu Ser Ile Gly Gln Ile Tyr Leu Arg Ser Asn Pro Leu Met
         35                  40                  45 aag gag cct ttc acc cgc gaa gac gtc aag cac cgt ctg gtc ggt cac     192
Lys Glu Pro Phe Thr Arg Glu Asp Val Lys His Arg Leu Val Gly His
 50                  55                  60 tgg ggc acc acc ccg ggc ctg aac ttc ctc atc ggc cac atc aac cgt     240
Trp Gly Thr Thr Pro Gly Leu Asn Phe Leu Ile Gly His Ile Asn Arg
 65                  70                  75                  80 ctc att gct gat cac cag cag aac act gtg atc atc atg ggc ccg ggc     288
Leu Ile Ala Asp His Gln Gln Asn Thr Val Ile Ile Met Gly Pro Gly
                 85                  90                  95 cac ggc ggc ccg gct ggt acc gct cag tcc tac ctg gac ggc acc tac     336
His Gly Gly Pro Ala Gly Thr Ala Gln Ser Tyr Leu Asp Gly Thr Tyr
            100                 105                 110 acc gag tac ttc ccg aac atc acc aag gat gag gct ggc ctg cag aag     384
Thr Glu Tyr Phe Pro Asn Ile Thr Lys Asp Glu Ala Gly Leu Gln Lys
        115                 120                 125 ttc ttc cgc cag ttc tcc tac ccg ggt ggc atc ccg tcc cac tac gct     432
Phe Phe Arg Gln Phe Ser Tyr Pro Gly Gly Ile Pro Ser His Tyr Ala
130                 135                 140 ccg gag acc ccg ggc tcc atc cac gaa ggc ggc gag ctg ggt tac gcc     480
Pro Glu Thr Pro Gly Ser Ile His Glu Gly Gly Glu Leu Gly Tyr Ala
145                 150                 155                 160 ctg tcc cac gcc tac ggc gct gtg atg aac aac ccg agc ctg ttc gtc     528
Leu Ser His Ala Tyr Gly Ala Val Met Asn Asn Pro Ser Leu Phe Val
                165                 170                 175 ccg gcc atc gtc ggc gac ggt gaa gct gag acc ggc ccg ctg gcc acc     576
Pro Ala Ile Val Gly Asp Gly Glu Ala Glu Thr Gly Pro Leu Ala Thr
            180                 185                 190 ggc tgg cag tcc aac aag ctc atc aac ccg cgc acc gac ggt atc gtg     624
Gly Trp Gln Ser Asn Lys Leu Ile Asn Pro Arg Thr Asp Gly Ile Val
        195                 200                 205 ctg ccg atc ctg cac ctc aac ggc tac aag atc gcc aac ccg acc atc     672
Leu Pro Ile Leu His Leu Asn Gly Tyr Lys Ile Ala Asn Pro Thr Ile
210                 215                 220 ctg tcc cgc atc tcc gac gaa gag ctc cac gag ttc ttc cac ggc atg     720
Leu Ser Arg Ile Ser Asp Glu Glu Leu His Glu Phe Phe His Gly Met
225                 230                 235                 240 ggc tat gag ccg tac gag ttc gtc gct ggc ttc gac aac gag gat cac     768
Gly Tyr Glu Pro Tyr Glu Phe Val Ala Gly Phe Asp Asn Glu Asp His
                245                 250                 255 ctg tcg atc cac cgt cgt ttc gcc gag ctg ttc gag acc gtc ttc gac     816
Leu Ser Ile His Arg Arg Phe Ala Glu Leu Phe Glu Thr Val Phe Asp
            260                 265                 270 gag atc tgc gac atc aag gcc gcc gct cag acc gac gac atg act cgt     864
Glu Ile Cys Asp Ile Lys Ala Ala Ala Gln Thr Asp Asp Met Thr Arg
        275                 280                 285 ccg ttc tac ccg atg atc atc ttc cgt acc ccg aag ggc tgg acc tgc     912
Pro Phe Tyr Pro Met Ile Ile Phe Arg Thr Pro Lys Gly Trp Thr Cys
290                 295                 300 ccg aag ttc atc gac ggc aag aag acc gag ggc tcc tgg cgt tcc cac     960
Pro Lys Phe Ile Asp Gly Lys Lys Thr Glu Gly Ser Trp Arg Ser His
305                 310                 315                 320 cag gtg ccg ctg gct tcc gcc cgc gat acc gag gcc cac ttc gag gtc    1008
Gln Val Pro Leu Ala Ser Ala Arg Asp Thr Glu Ala His Phe Glu Val
```

|  |  |  |  |  |  |  |  |  |  |  |  |  |  |  |  |
|---|---|---|---|---|---|---|---|---|---|---|---|---|---|---|---|
|  |  | 325 |  |  |  | 330 |  |  |  |  | 335 |  |  |  |  |
| ctc | aag | aac | tgg | ctc | gag | tcc | tac | aag | ccg | gaa | gag | ctg | ttc | gac | gag |
| Leu | Lys | Asn | Trp | Leu | Glu | Ser | Tyr | Lys | Pro | Glu | Glu | Leu | Phe | Asp | Glu |
|  |  | 340 |  |  |  | 345 |  |  |  |  | 350 |  |  |  |  |

1056 aac ggc gcc gtg aag ccg gaa gtc acc gcc ttc atg ccg acc ggc gaa  1104
Asn Gly Ala Val Lys Pro Glu Val Thr Ala Phe Met Pro Thr Gly Glu
             355                 360                 365 ctg cgc atc ggt gag aac ccg aac gcc aac ggt ggc cgc atc cgc gaa  1152
Leu Arg Ile Gly Glu Asn Pro Asn Ala Asn Gly Gly Arg Ile Arg Glu
        370                 375                 380 gag ctg aag ctg ccg aag ctg gaa gac tac gag gtc aag gaa gtc gcc  1200
Glu Leu Lys Leu Pro Lys Leu Glu Asp Tyr Glu Val Lys Glu Val Ala
385                 390                 395                 400 gag tac ggc cac ggc tgg ggc cag ctc gag gcc acc cgt cgt ctg ggc  1248
Glu Tyr Gly His Gly Trp Gly Gln Leu Glu Ala Thr Arg Arg Leu Gly
                405                 410                 415 gtc tac acc cgc gac atc atc aag aac aac ccg gac tcc ttc cgt atc  1296
Val Tyr Thr Arg Asp Ile Ile Lys Asn Asn Pro Asp Ser Phe Arg Ile
            420                 425                 430 ttc gga ccg gat gag acc gct tcc aac cgt ctg cag gcc gct tac gac  1344
Phe Gly Pro Asp Glu Thr Ala Ser Asn Arg Leu Gln Ala Ala Tyr Asp
        435                 440                 445 gtc acc aac aag cag tgg gac gcc ggc tac ctg tcc gct cag gtc gac  1392
Val Thr Asn Lys Gln Trp Asp Ala Gly Tyr Leu Ser Ala Gln Val Asp
    450                 455                 460 gag cac atg gct gtc acc ggc cag gtc acc gag cag ctt tcc gag cac  1440
Glu His Met Ala Val Thr Gly Gln Val Thr Glu Gln Leu Ser Glu His
465                 470                 475                 480 cag atg gaa ggc ttc ctc gag ggc tac ctg ctg acc ggc cgt cac ggc  1488
Gln Met Glu Gly Phe Leu Glu Gly Tyr Leu Leu Thr Gly Arg His Gly
                485                 490                 495 atc tgg agc tcc tat gag tcc ttc gtg cac gtg atc gac tcc atg ctg  1536
Ile Trp Ser Ser Tyr Glu Ser Phe Val His Val Ile Asp Ser Met Leu
            500                 505                 510 aac cag cac gcc aag tgg ctc gag gct acc gtc cgc gag att ccg tgg  1584
Asn Gln His Ala Lys Trp Leu Glu Ala Thr Val Arg Glu Ile Pro Trp
        515                 520                 525 cgc aag ccg atc tcc tcc atg aac ctg ctc gtc tcc tcc cac gtg tgg  1632
Arg Lys Pro Ile Ser Ser Met Asn Leu Leu Val Ser Ser His Val Trp
    530                 535                 540 cgt cag gat cac aac ggc ttc tcc cac cag gat ccg ggt gtc acc tcc  1680
Arg Gln Asp His Asn Gly Phe Ser His Gln Asp Pro Gly Val Thr Ser
545                 550                 555                 560 gtc ctg ctg aac aag tgc ttc aac aac gat cac gtg atc ggc atc tac  1728
Val Leu Leu Asn Lys Cys Phe Asn Asn Asp His Val Ile Gly Ile Tyr
                565                 570                 575 ttc ccg gtg gat tcc aac atg ctg ctc gct gtg gct gag aag tgc tac  1776
Phe Pro Val Asp Ser Asn Met Leu Leu Ala Val Ala Glu Lys Cys Tyr
            580                 585                 590 aag tcc acc aac aag atc aac gcc atc atc gcc ggc aag cag ccg gcc  1824
Lys Ser Thr Asn Lys Ile Asn Ala Ile Ile Ala Gly Lys Gln Pro Ala
        595                 600                 605 gcc acc tgg ctg acc ctg gac gaa gct cgc gcc gag ctc gag aag ggt  1872
Ala Thr Trp Leu Thr Leu Asp Glu Ala Arg Ala Glu Leu Glu Lys Gly
    610                 615                 620 gct gcc gag tgg aag tgg gct tcc aac gtg aag tcc aac gat gag gct  1920
Ala Ala Glu Trp Lys Trp Ala Ser Asn Val Lys Ser Asn Asp Glu Ala
625                 630                 635                 640 cag atc gtg ctc gcc gcc acc ggt gat gtt ccg act cag gaa atc atg  1968
Gln Ile Val Leu Ala Ala Thr Gly Asp Val Pro Thr Gln Glu Ile Met

```
Gln Ile Val Leu Ala Ala Thr Gly Asp Val Pro Thr Gln Glu Ile Met
                645                 650                 655 gcc gct gcc gac aag ctg gac gcc atg ggc atc aag ttc aag gtc gtc    2016
Ala Ala Ala Asp Lys Leu Asp Ala Met Gly Ile Lys Phe Lys Val Val
            660                 665                 670 aac gtg gtt gac ctg gtc aag ctg cag tcc gcc aag gag aac aac gag    2064
Asn Val Val Asp Leu Val Lys Leu Gln Ser Ala Lys Glu Asn Asn Glu
        675                 680                 685 gcc ctc tcc gat gag gag ttc gct gag ctg ttc acc gag gac aag ccg    2112
Ala Leu Ser Asp Glu Glu Phe Ala Glu Leu Phe Thr Glu Asp Lys Pro
    690                 695                 700 gtc ctg ttc gct tac cac tcc tat gcc cgc gat gtg cgt ggt ctg atc    2160
Val Leu Phe Ala Tyr His Ser Tyr Ala Arg Asp Val Arg Gly Leu Ile
705                 710                 715                 720 tac gat cgc ccg aac cac gac aac ttc aac gtt cac ggc tac gag gag    2208
Tyr Asp Arg Pro Asn His Asp Asn Phe Asn Val His Gly Tyr Glu Glu
                725                 730                 735 cag ggc tcc acc acc acc ccg tac gac atg gtt cgc gtg aac aac atc    2256
Gln Gly Ser Thr Thr Thr Pro Tyr Asp Met Val Arg Val Asn Asn Ile
            740                 745                 750 gat cgc tac gag ctc cag gct gaa gct ctg cgc atg att gac gct gac    2304
Asp Arg Tyr Glu Leu Gln Ala Glu Ala Leu Arg Met Ile Asp Ala Asp
        755                 760                 765 aag tac gcc gac aag atc aac gag ctc gag gcc ttc cgt cag gaa gcc    2352
Lys Tyr Ala Asp Lys Ile Asn Glu Leu Glu Ala Phe Arg Gln Glu Ala
    770                 775                 780 ttc cag ttc gct gtc gac aac ggc tac gat cac ccg gat tac acc gac    2400
Phe Gln Phe Ala Val Asp Asn Gly Tyr Asp His Pro Asp Tyr Thr Asp
785                 790                 795                 800 tgg gtc tac tcc ggt gtc aac acc aac aag cag ggt gct atc tcc gct    2448
Trp Val Tyr Ser Gly Val Asn Thr Asn Lys Gln Gly Ala Ile Ser Ala
                805                 810                 815 acc gcc gca acc gct ggc gat aac gag tga                            2478
Thr Ala Ala Thr Ala Gly Asp Asn Glu
            820                 825

<210> SEQ ID NO 2
<211> LENGTH: 825
<212> TYPE: PRT
<213> ORGANISM: Bifidobacterium adolescentis

<400> SEQUENCE: 2

Met Thr Ser Pro Val Ile Gly Thr Pro Trp Lys Lys Leu Asn Ala Pro
1               5                   10                  15

Val Ser Glu Glu Ala Ile Glu Gly Val Asp Lys Tyr Trp Arg Ala Ala
                20                  25                  30

Asn Tyr Leu Ser Ile Gly Gln Ile Tyr Leu Arg Ser Asn Pro Leu Met
            35                  40                  45

Lys Glu Pro Phe Thr Arg Glu Asp Val Lys His Arg Leu Val Gly His
        50                  55                  60

Trp Gly Thr Thr Pro Gly Leu Asn Phe Leu Ile Gly His Ile Asn Arg
65                  70                  75                  80

Leu Ile Ala Asp His Gln Gln Asn Thr Val Ile Ile Met Gly Pro Gly
                85                  90                  95

His Gly Gly Pro Ala Gly Thr Ala Gln Ser Tyr Leu Asp Gly Thr Tyr
            100                 105                 110

Thr Glu Tyr Phe Pro Asn Ile Thr Lys Asp Glu Ala Gly Leu Gln Lys
        115                 120                 125
```

```
Phe Phe Arg Gln Phe Ser Tyr Pro Gly Gly Ile Pro Ser His Tyr Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Ala Ile Val Gly Asp Gly Glu Ala Glu Thr Gly Pro Leu Ala Thr
            180                 185                 190

Gly Trp Gln Ser Asn Lys Leu Ile Asn Pro Arg Thr Asp Gly Ile Val
        195                 200                 205

Leu Pro Ile Leu His Leu Asn Gly Tyr Lys Ile Ala Asn Pro Thr Ile
210                 215                 220

Leu Ser Arg Ile Ser Asp Glu Glu Leu His Glu Phe His Gly Met
225                 230                 235                 240

Gly Tyr Glu Pro Tyr Glu Phe Val Ala Gly Phe Asp Asn Glu Asp His
                245                 250                 255

Leu Ser Ile His Arg Arg Phe Ala Glu Leu Phe Glu Thr Val Phe Asp
            260                 265                 270

Glu Ile Cys Asp Ile Lys Ala Ala Gln Thr Asp Asp Met Thr Arg
        275                 280                 285

Pro Phe Tyr Pro Met Ile Ile Phe Arg Thr Pro Lys Gly Trp Thr Cys
290                 295                 300

Pro Lys Phe Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
                325                 330                 335

Leu Lys Asn Trp Leu Glu Ser Tyr Lys Pro Glu Glu Leu Phe Asp Glu
            340                 345                 350

Asn Gly Ala Val Lys Pro Glu Val Thr Ala Phe Met Pro Thr Gly Glu
        355                 360                 365

Leu Arg Ile Gly Glu Asn Pro Asn Ala Asn Gly Arg Ile Arg Glu
370                 375                 380

Glu Leu Lys Leu Pro Lys Leu Glu Asp Tyr Glu Val Lys Glu Val Ala
385                 390                 395                 400

Glu Tyr Gly His Gly Trp Gly Gln Leu Glu Ala Thr Arg Arg Leu Gly
                405                 410                 415

Val Tyr Thr Arg Asp Ile Ile Lys Asn Asn Pro Asp Ser Phe Arg Ile
            420                 425                 430

Phe Gly Pro Asp Glu Thr Ala Ser Asn Arg Leu Gln Ala Ala Tyr Asp
        435                 440                 445

Val Thr Asn Lys Gln Trp Asp Ala Gly Tyr Leu Ser Ala Gln Val Asp
450                 455                 460

Glu His Met Ala Val Thr Gly Gln Val Thr Glu Gln Leu Ser Glu His
465                 470                 475                 480

Gln Met Glu Gly Phe Leu Glu Gly Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Met Asn Leu Leu Val Ser Ser His Val Trp
530                 535                 540

Arg Gln Asp His Asn Gly Phe Ser His Gln Asp Pro Gly Val Thr Ser
```

```
                545                 550                 555                 560
Val Leu Leu Asn Lys Cys Phe Asn Asn Asp His Val Ile Gly Ile Tyr
                565                 570                 575

Phe Pro Val Asp Ser Asn Met Leu Leu Ala Val Ala Glu Lys Cys Tyr
                580                 585                 590

Lys Ser Thr Asn Lys Ile Asn Ala Ile Ile Ala Gly Lys Gln Pro Ala
                595                 600                 605

Ala Thr Trp Leu Thr Leu Asp Glu Ala Arg Ala Glu Leu Glu Lys Gly
                610                 615                 620

Ala Ala Glu Trp Lys Trp Ala Ser Asn Val Lys Ser Asn Asp Glu Ala
625                 630                 635                 640

Gln Ile Val Leu Ala Ala Thr Gly Asp Val Pro Thr Gln Glu Ile Met
                645                 650                 655

Ala Ala Ala Asp Lys Leu Asp Ala Met Gly Ile Lys Phe Lys Val Val
                660                 665                 670

Asn Val Val Asp Leu Val Lys Leu Gln Ser Ala Lys Glu Asn Asn Glu
                675                 680                 685

Ala Leu Ser Asp Glu Glu Phe Ala Glu Leu Phe Thr Glu Asp Lys Pro
                690                 695                 700

Val Leu Phe Ala Tyr His Ser Tyr Ala Arg Asp Val Arg Gly Leu Ile
705                 710                 715                 720

Tyr Asp Arg Pro Asn His Asp Asn Phe Asn Val His Gly Tyr Glu Glu
                725                 730                 735

Gln Gly Ser Thr Thr Thr Pro Tyr Asp Met Val Arg Val Asn Asn Ile
                740                 745                 750

Asp Arg Tyr Glu Leu Gln Ala Glu Ala Leu Arg Met Ile Asp Ala Asp
                755                 760                 765

Lys Tyr Ala Asp Lys Ile Asn Glu Leu Glu Ala Phe Arg Gln Glu Ala
                770                 775                 780

Phe Gln Phe Ala Val Asp Asn Gly Tyr Asp His Pro Asp Tyr Thr Asp
785                 790                 795                 800

Trp Val Tyr Ser Gly Val Asn Thr Asn Lys Gln Gly Ala Ile Ser Ala
                805                 810                 815

Thr Ala Ala Thr Ala Gly Asp Asn Glu
                820                 825

<210> SEQ ID NO 3
<211> LENGTH: 1152
<212> TYPE: DNA
<213> ORGANISM: Bacillus methanolicus
<220> FEATURE:
<221> NAME/KEY: CDS
<222> LOCATION: (1)..(1152)

<400> SEQUENCE: 3 atg acg caa aga aac ttt ttc att cca cca gct agc gta att gga cgc     48
Met Thr Gln Arg Asn Phe Phe Ile Pro Pro Ala Ser Val Ile Gly Arg
1               5                   10                  15 ggc gct gta aaa gaa gta gga aca aga ctt aag caa att gga gct aca     96
Gly Ala Val Lys Glu Val Gly Thr Arg Leu Lys Gln Ile Gly Ala Thr
            20                  25                  30 aaa gca ctt atc gtt aca gat gca ttt ctt cat ggc aca ggt ttg tca    144
Lys Ala Leu Ile Val Thr Asp Ala Phe Leu His Gly Thr Gly Leu Ser
        35                  40                  45 gaa gaa gtt gct aaa aac att cgt gaa gct ggc ctt gat gct gta att    192
Glu Glu Val Ala Lys Asn Ile Arg Glu Ala Gly Leu Asp Ala Val Ile
    50                  55                  60
```

-continued

| | |
|---|---|
| ttc cca aaa gct caa cca gat cca gca gat aca caa gtt cat gaa ggc<br>Phe Pro Lys Ala Gln Pro Asp Pro Ala Asp Thr Gln Val His Glu Gly<br>65                    70                        75                    80 | 240 |
| gta gat ata ttc aaa caa gaa aaa tgt gat gca ctt gtt tct atc ggt<br>Val Asp Ile Phe Lys Gln Glu Lys Cys Asp Ala Leu Val Ser Ile Gly<br>                    85                        90                        95 | 288 |
| gga ggt agc tct cac gat aca gca aaa gca atc ggt tta gtt gca gca<br>Gly Gly Ser Ser His Asp Thr Ala Lys Ala Ile Gly Leu Val Ala Ala<br>                  100                      105                      110 | 336 |
| aac ggc gga aga atc aac gac tat caa ggt gta aac agt gta gaa aaa<br>Asn Gly Gly Arg Ile Asn Asp Tyr Gln Gly Val Asn Ser Val Glu Lys<br>            115                      120                      125 | 384 |
| ccg gtt gtt cca gta gtt gca atc act aca aca gct ggt act ggt agt<br>Pro Val Val Pro Val Val Ala Ile Thr Thr Thr Ala Gly Thr Gly Ser<br>130                        135                      140 | 432 |
| gaa aca aca tct ctt gcg gtt att aca gat tct gca cgt aaa gta aaa<br>Glu Thr Thr Ser Leu Ala Val Ile Thr Asp Ser Ala Arg Lys Val Lys<br>145                        150                      155                      160 | 480 |
| atg cca gtt atc gat gag aaa att aca cca act gta gca att gtt gac<br>Met Pro Val Ile Asp Glu Lys Ile Thr Pro Thr Val Ala Ile Val Asp<br>                  165                      170                      175 | 528 |
| cca gaa tta atg gtg aaa aaa cca gct gga tta aca att gca act ggt<br>Pro Glu Leu Met Val Lys Lys Pro Ala Gly Leu Thr Ile Ala Thr Gly<br>                      180                      185                      190 | 576 |
| atg gat gca tta tcc cat gca att gaa gca tat gtt gca aaa cgt gct<br>Met Asp Ala Leu Ser His Ala Ile Glu Ala Tyr Val Ala Lys Arg Ala<br>            195                      200                      205 | 624 |
| aca cca gtt act gat gcg ttt gca att caa gca atg aaa ctc att aat<br>Thr Pro Val Thr Asp Ala Phe Ala Ile Gln Ala Met Lys Leu Ile Asn<br>210                        215                      220 | 672 |
| gaa tac tta cca cgt gcg gtt gca aat gga gaa gac atc gaa gca cgt<br>Glu Tyr Leu Pro Arg Ala Val Ala Asn Gly Glu Asp Ile Glu Ala Arg<br>225                        230                      235                      240 | 720 |
| gaa gca atg gct tat gca caa tac atg gca gga gtg gca ttt aac aac<br>Glu Ala Met Ala Tyr Ala Gln Tyr Met Ala Gly Val Ala Phe Asn Asn<br>                  245                      250                      255 | 768 |
| gga ggt tta gga tta gta cac tct att tct cac caa gta ggt gga gtt<br>Gly Gly Leu Gly Leu Val His Ser Ile Ser His Gln Val Gly Gly Val<br>            260                      265                      270 | 816 |
| tac aag tta caa cac gga atc tgt aac tca gtt aat atg cca cac gtt<br>Tyr Lys Leu Gln His Gly Ile Cys Asn Ser Val Asn Met Pro His Val<br>            275                      280                      285 | 864 |
| tgc caa ttc aac tta att gct cgt act gaa cgc ttc gca cac att gct<br>Cys Gln Phe Asn Leu Ile Ala Arg Thr Glu Arg Phe Ala His Ile Ala<br>            290                      295                      300 | 912 |
| gag ctt tta ggc gag aat gtt tct ggc tta agc act gca tct gct gct<br>Glu Leu Leu Gly Glu Asn Val Ser Gly Leu Ser Thr Ala Ser Ala Ala<br>305                        310                      315                      320 | 960 |
| gag aga gca att gta gcg ctt caa cgc tat aac aaa aac ttc ggt atc<br>Glu Arg Ala Ile Val Ala Leu Gln Arg Tyr Asn Lys Asn Phe Gly Ile<br>                  325                      330                      335 | 1008 |
| cca tct ggc tat gca gaa atg ggc gta aaa gaa gag gat atc gaa tta<br>Pro Ser Gly Tyr Ala Glu Met Gly Val Lys Glu Glu Asp Ile Glu Leu<br>                  340                      345                      350 | 1056 |
| tta gcg aac aac gcg tac caa gac gta tgt act cta gat aac cca cgt<br>Leu Ala Asn Asn Ala Tyr Gln Asp Val Cys Thr Leu Asp Asn Pro Arg<br>            355                      360                      365 | 1104 |
| gtt cct act gtt caa gac att gca caa atc atc aaa aac gct ctg taa<br>Val Pro Thr Val Gln Asp Ile Ala Gln Ile Ile Lys Asn Ala Leu | 1152 |

```
            370             375             380
```

<210> SEQ ID NO 4
<211> LENGTH: 383
<212> TYPE: PRT
<213> ORGANISM: Bacillus methanolicus

<400> SEQUENCE: 4

```
Met Thr Gln Arg Asn Phe Phe Ile Pro Pro Ala Ser Val Ile Gly Arg
1               5                   10                  15

Gly Ala Val Lys Glu Val Gly Thr Arg Leu Lys Gln Ile Gly Ala Thr
            20                  25                  30

Lys Ala Leu Ile Val Thr Asp Ala Phe Leu His Gly Thr Gly Leu Ser
        35                  40                  45

Glu Glu Val Ala Lys Asn Ile Arg Glu Ala Gly Leu Asp Ala Val Ile
    50                  55                  60

Phe Pro Lys Ala Gln Pro Asp Pro Ala Asp Thr Gln Val His Glu Gly
65                  70                  75                  80

Val Asp Ile Phe Lys Gln Glu Lys Cys Asp Ala Leu Val Ser Ile Gly
                85                  90                  95

Gly Gly Ser Ser His Asp Thr Ala Lys Ala Ile Gly Leu Val Ala Ala
            100                 105                 110

Asn Gly Gly Arg Ile Asn Asp Tyr Gln Gly Val Asn Ser Val Glu Lys
        115                 120                 125

Pro Val Val Pro Val Ala Ile Thr Thr Thr Ala Gly Thr Gly Ser
    130                 135                 140

Glu Thr Thr Ser Leu Ala Val Ile Thr Asp Ser Ala Arg Lys Val Lys
145                 150                 155                 160

Met Pro Val Ile Asp Glu Lys Ile Thr Pro Thr Val Ala Ile Val Asp
                165                 170                 175

Pro Glu Leu Met Val Lys Lys Pro Ala Gly Leu Thr Ile Ala Thr Gly
            180                 185                 190

Met Asp Ala Leu Ser His Ala Ile Glu Ala Tyr Val Ala Lys Arg Ala
        195                 200                 205

Thr Pro Val Thr Asp Ala Phe Ala Ile Gln Ala Met Lys Leu Ile Asn
    210                 215                 220

Glu Tyr Leu Pro Arg Ala Val Ala Asn Gly Glu Asp Ile Glu Ala Arg
225                 230                 235                 240

Glu Ala Met Ala Tyr Ala Gln Tyr Met Ala Gly Val Ala Phe Asn Asn
                245                 250                 255

Gly Gly Leu Gly Leu Val His Ser Ile Ser His Gln Val Gly Gly Val
            260                 265                 270

Tyr Lys Leu Gln His Gly Ile Cys Asn Ser Val Asn Met Pro His Val
        275                 280                 285

Cys Gln Phe Asn Leu Ile Ala Arg Thr Glu Arg Phe Ala His Ile Ala
    290                 295                 300

Glu Leu Leu Gly Glu Asn Val Ser Gly Leu Ser Thr Ala Ser Ala Ala
305                 310                 315                 320

Glu Arg Ala Ile Val Ala Leu Gln Arg Tyr Asn Lys Asn Phe Gly Ile
                325                 330                 335

Pro Ser Gly Tyr Ala Glu Met Gly Val Lys Glu Glu Asp Ile Glu Leu
            340                 345                 350

Leu Ala Asn Asn Ala Tyr Gln Asp Val Cys Thr Leu Asp Asn Pro Arg
        355                 360                 365
```

```
Val Pro Thr Val Gln Asp Ile Ala Gln Ile Ile Lys Asn Ala Leu
    370                 375                 380
```

<210> SEQ ID NO 5
<211> LENGTH: 678
<212> TYPE: DNA
<213> ORGANISM: Escherichia coli
<220> FEATURE:
<221> NAME/KEY: CDS
<222> LOCATION: (1)..(678)

<400> SEQUENCE: 5

```
atg aaa cag tat ttg att gcc ccc tca att ctg tcg gct gat ttt gcc    48
Met Lys Gln Tyr Leu Ile Ala Pro Ser Ile Leu Ser Ala Asp Phe Ala
1               5                   10                  15 cgc ctg ggt gaa gat acc gca aaa gcc ctg gca gct ggc gct gat gtc    96
Arg Leu Gly Glu Asp Thr Ala Lys Ala Leu Ala Ala Gly Ala Asp Val
                20                  25                  30 gtg cat ttt gac gtc atg gat aac cac tat gtt ccc aat ctg acg att   144
Val His Phe Asp Val Met Asp Asn His Tyr Val Pro Asn Leu Thr Ile
            35                  40                  45 ggg cca atg gtg ctg aaa tcc ttg cgt aac tat ggc att acc gcc cct   192
Gly Pro Met Val Leu Lys Ser Leu Arg Asn Tyr Gly Ile Thr Ala Pro
        50                  55                  60 atc gac gta cac ctg atg gtg aaa ccc gtc gat cgc att gtg cct gat   240
Ile Asp Val His Leu Met Val Lys Pro Val Asp Arg Ile Val Pro Asp
65                  70                  75                  80 ttc gct gcc gct ggt gcc agc atc att acc ttt cat cca gaa gcc tcc   288
Phe Ala Ala Ala Gly Ala Ser Ile Ile Thr Phe His Pro Glu Ala Ser
                85                  90                  95 gag cat gtt gac cgc acg ctg caa ctg att aaa gaa aat ggc tgt aaa   336
Glu His Val Asp Arg Thr Leu Gln Leu Ile Lys Glu Asn Gly Cys Lys
                100                 105                 110 gcg ggt ctg gta ttt aac ccg gcg aca cct ctg agc tat ctg gat tac   384
Ala Gly Leu Val Phe Asn Pro Ala Thr Pro Leu Ser Tyr Leu Asp Tyr
            115                 120                 125 gtg atg gat aag ctg gat gtg atc ctg ctg atg tcc gtc aac cct ggt   432
Val Met Asp Lys Leu Asp Val Ile Leu Leu Met Ser Val Asn Pro Gly
        130                 135                 140 ttc ggc ggt cag tct ttc att cct caa aca ctg gat aaa ctg cgc gaa   480
Phe Gly Gly Gln Ser Phe Ile Pro Gln Thr Leu Asp Lys Leu Arg Glu
145                 150                 155                 160 gta cgt cgc cgt atc gac gag tct ggc ttt gac att cga cta gaa gtg   528
Val Arg Arg Arg Ile Asp Glu Ser Gly Phe Asp Ile Arg Leu Glu Val
                165                 170                 175 gac ggt ggc gtg aag gtg aac aac att ggc gaa atc gct gcg gcg ggc   576
Asp Gly Gly Val Lys Val Asn Asn Ile Gly Glu Ile Ala Ala Ala Gly
                180                 185                 190 gcg gat atg ttc gtc gcc ggt tcg gca atc ttc gac cag cca gac tac   624
Ala Asp Met Phe Val Ala Gly Ser Ala Ile Phe Asp Gln Pro Asp Tyr
            195                 200                 205 aaa aaa gtc att gat gaa atg cgc agt gaa ctg gca aag gta agt cat   672
Lys Lys Val Ile Asp Glu Met Arg Ser Glu Leu Ala Lys Val Ser His
        210                 215                 220 gaa taa                                                           678
Glu
225
```

<210> SEQ ID NO 6
<211> LENGTH: 225
<212> TYPE: PRT
<213> ORGANISM: Escherichia coli

<400> SEQUENCE: 6

```
Met Lys Gln Tyr Leu Ile Ala Pro Ser Ile Leu Ser Ala Asp Phe Ala
1               5                   10                  15

Arg Leu Gly Glu Asp Thr Ala Lys Ala Leu Ala Ala Gly Ala Asp Val
            20                  25                  30

Val His Phe Asp Val Met Asp Asn His Tyr Val Pro Asn Leu Thr Ile
        35                  40                  45

Gly Pro Met Val Leu Lys Ser Leu Arg Asn Tyr Gly Ile Thr Ala Pro
    50                  55                  60

Ile Asp Val His Leu Met Val Lys Pro Val Asp Arg Ile Val Pro Asp
65                  70                  75                  80

Phe Ala Ala Ala Gly Ala Ser Ile Ile Thr Phe His Pro Glu Ala Ser
                85                  90                  95

Glu His Val Asp Arg Thr Leu Gln Leu Ile Lys Glu Asn Gly Cys Lys
            100                 105                 110

Ala Gly Leu Val Phe Asn Pro Ala Thr Pro Leu Ser Tyr Leu Asp Tyr
        115                 120                 125

Val Met Asp Lys Leu Asp Val Ile Leu Leu Met Ser Val Asn Pro Gly
    130                 135                 140

Phe Gly Gly Gln Ser Phe Ile Pro Gln Thr Leu Asp Lys Leu Arg Glu
145                 150                 155                 160

Val Arg Arg Arg Ile Asp Glu Ser Gly Phe Asp Ile Arg Leu Glu Val
                165                 170                 175

Asp Gly Gly Val Lys Val Asn Asn Ile Gly Glu Ile Ala Ala Ala Gly
            180                 185                 190

Ala Asp Met Phe Val Ala Gly Ser Ala Ile Phe Asp Gln Pro Asp Tyr
        195                 200                 205

Lys Lys Val Ile Asp Glu Met Arg Ser Glu Leu Ala Lys Val Ser His
    210                 215                 220

Glu
225
```

<210> SEQ ID NO 7
<211> LENGTH: 660
<212> TYPE: DNA
<213> ORGANISM: Escherichia coli
<220> FEATURE:
<221> NAME/KEY: CDS
<222> LOCATION: (1)..(660)

<400> SEQUENCE: 7

```
atg acg cag gat gaa ttg aaa aaa gca gta gga tgg gcg gca ctt cag     48
Met Thr Gln Asp Glu Leu Lys Lys Ala Val Gly Trp Ala Ala Leu Gln
1               5                   10                  15 tat gtt cag ccc ggc acc att gtt ggt gta ggt aca ggt tcc acc gcc     96
Tyr Val Gln Pro Gly Thr Ile Val Gly Val Gly Thr Gly Ser Thr Ala
            20                  25                  30 gca cac ttt att gac gcg ctc ggt aca atg aaa ggc cag att gaa ggg    144
Ala His Phe Ile Asp Ala Leu Gly Thr Met Lys Gly Gln Ile Glu Gly
        35                  40                  45 gcc gtt tcc agt tca gat gct tcc act gaa aaa ctg aaa agc ctc ggc    192
Ala Val Ser Ser Ser Asp Ala Ser Thr Glu Lys Leu Lys Ser Leu Gly
    50                  55                  60 att cac gtt ttt gat ctc aac gaa gtc gac agc ctt ggc atc tac gtt    240
Ile His Val Phe Asp Leu Asn Glu Val Asp Ser Leu Gly Ile Tyr Val
65                  70                  75                  80
```

```
gat ggc gca gat gaa atc aac ggc cac atg caa atg atc aaa ggc ggc       288
Asp Gly Ala Asp Glu Ile Asn Gly His Met Gln Met Ile Lys Gly Gly
                85                  90                  95 ggc gcg gcg ctg acc cgt gaa aaa atc att gct tcg gtt gca gaa aaa       336
Gly Ala Ala Leu Thr Arg Glu Lys Ile Ile Ala Ser Val Ala Glu Lys
            100                 105                 110 ttt atc tgt att gca gac gct tcc aag cag gtt gat att ctg ggt aaa       384
Phe Ile Cys Ile Ala Asp Ala Ser Lys Gln Val Asp Ile Leu Gly Lys
        115                 120                 125 ttc ccg ctg cca gta gaa gtt atc ccg atg gca cgt agt gca gtg gcg       432
Phe Pro Leu Pro Val Glu Val Ile Pro Met Ala Arg Ser Ala Val Ala
    130                 135                 140 cgt cag ctg gtg aaa ctg ggc ggt cgt ccg gaa tac cgt cag ggc gtg       480
Arg Gln Leu Val Lys Leu Gly Gly Arg Pro Glu Tyr Arg Gln Gly Val
145                 150                 155                 160 gtg acc gat aat ggc aac gtg atc ctc gac gtc cac ggc atg gaa atc       528
Val Thr Asp Asn Gly Asn Val Ile Leu Asp Val His Gly Met Glu Ile
                165                 170                 175 ctt gac ccg ata gcg atg gaa aac gcc ata aat gcg att cct ggc gtg       576
Leu Asp Pro Ile Ala Met Glu Asn Ala Ile Asn Ala Ile Pro Gly Val
            180                 185                 190 gtg act gtt ggc ttg ttt gct aac cgt ggc gcg gac gtt gcg ctg att       624
Val Thr Val Gly Leu Phe Ala Asn Arg Gly Ala Asp Val Ala Leu Ile
        195                 200                 205 ggc aca cct gac ggt gtc aaa acc att gtg aaa tga                       660
Gly Thr Pro Asp Gly Val Lys Thr Ile Val Lys
    210                 215

<210> SEQ ID NO 8
<211> LENGTH: 219
<212> TYPE: PRT
<213> ORGANISM: Escherichia coli

<400> SEQUENCE: 8

Met Thr Gln Asp Glu Leu Lys Lys Ala Val Gly Trp Ala Ala Leu Gln
1               5                   10                  15

Tyr Val Gln Pro Gly Thr Ile Val Gly Val Gly Thr Gly Ser Thr Ala
            20                  25                  30

Ala His Phe Ile Asp Ala Leu Gly Thr Met Lys Gly Gln Ile Glu Gly
        35                  40                  45

Ala Val Ser Ser Ser Asp Ala Ser Thr Glu Lys Leu Lys Ser Leu Gly
    50                  55                  60

Ile His Val Phe Asp Leu Asn Glu Val Asp Ser Leu Gly Ile Tyr Val
65                  70                  75                  80

Asp Gly Ala Asp Glu Ile Asn Gly His Met Gln Met Ile Lys Gly Gly
                85                  90                  95

Gly Ala Ala Leu Thr Arg Glu Lys Ile Ile Ala Ser Val Ala Glu Lys
            100                 105                 110

Phe Ile Cys Ile Ala Asp Ala Ser Lys Gln Val Asp Ile Leu Gly Lys
        115                 120                 125

Phe Pro Leu Pro Val Glu Val Ile Pro Met Ala Arg Ser Ala Val Ala
    130                 135                 140

Arg Gln Leu Val Lys Leu Gly Gly Arg Pro Glu Tyr Arg Gln Gly Val
145                 150                 155                 160

Val Thr Asp Asn Gly Asn Val Ile Leu Asp Val His Gly Met Glu Ile
                165                 170                 175

Leu Asp Pro Ile Ala Met Glu Asn Ala Ile Asn Ala Ile Pro Gly Val
            180                 185                 190
```

```
Val Thr Val Gly Leu Phe Ala Asn Arg Gly Ala Asp Val Ala Leu Ile
        195                 200                 205

Gly Thr Pro Asp Gly Val Lys Thr Ile Val Lys
        210                 215

<210> SEQ ID NO 9
<211> LENGTH: 954
<212> TYPE: DNA
<213> ORGANISM: Escherichia coli
<220> FEATURE:
<221> NAME/KEY: CDS
<222> LOCATION: (1)..(954)

<400> SEQUENCE: 9 atg acg gac aaa ttg acc tcc ctt cgt cag tac acc acc gta gtg gcc       48
Met Thr Asp Lys Leu Thr Ser Leu Arg Gln Tyr Thr Thr Val Val Ala
1               5                   10                  15 gac act ggg gac atc gcg gca atg aag ctg tat caa ccg cag gat gcc       96
Asp Thr Gly Asp Ile Ala Ala Met Lys Leu Tyr Gln Pro Gln Asp Ala
            20                  25                  30 aca acc aac cct tct ctc att ctt aac gca gcg cag att ccg gaa tac      144
Thr Thr Asn Pro Ser Leu Ile Leu Asn Ala Ala Gln Ile Pro Glu Tyr
        35                  40                  45 cgt aag ttg att gat gat gct gtc gcc tgg gcg aaa cag cag agc aac      192
Arg Lys Leu Ile Asp Asp Ala Val Ala Trp Ala Lys Gln Gln Ser Asn
    50                  55                  60 gat cgc gcg cag cag atc gtg gac gcg acc gac aaa ctg gca gta aat      240
Asp Arg Ala Gln Gln Ile Val Asp Ala Thr Asp Lys Leu Ala Val Asn
65                  70                  75                  80 att ggt ctg gaa atc ctg aaa ctg gtt ccg ggc cgt atc tca act gaa      288
Ile Gly Leu Glu Ile Leu Lys Leu Val Pro Gly Arg Ile Ser Thr Glu
                85                  90                  95 gtt gat gcg cgt ctt tcc tat gac acc gaa gcg tca att gcg aaa gca      336
Val Asp Ala Arg Leu Ser Tyr Asp Thr Glu Ala Ser Ile Ala Lys Ala
            100                 105                 110 aaa cgc ctg atc aaa ctc tac aac gat gct ggt att agc aac gat cgt      384
Lys Arg Leu Ile Lys Leu Tyr Asn Asp Ala Gly Ile Ser Asn Asp Arg
        115                 120                 125 att ctg atc aaa ctg gct tct acc tgg cag ggt atc cgt gct gca gaa      432
Ile Leu Ile Lys Leu Ala Ser Thr Trp Gln Gly Ile Arg Ala Ala Glu
    130                 135                 140 cag ctg gaa aaa gaa ggc atc aac tgt aac ctg acc ctg ctg ttc tcc      480
Gln Leu Glu Lys Glu Gly Ile Asn Cys Asn Leu Thr Leu Leu Phe Ser
145                 150                 155                 160 ttc gct cag gct cgt gct tgt gcg gaa gcg ggc gtg ttc ctg atc tcg      528
Phe Ala Gln Ala Arg Ala Cys Ala Glu Ala Gly Val Phe Leu Ile Ser
                165                 170                 175 ccg ttt gtt ggc cgt att ctt gac tgg tac aaa gcg aat acc gat aag      576
Pro Phe Val Gly Arg Ile Leu Asp Trp Tyr Lys Ala Asn Thr Asp Lys
            180                 185                 190 aaa gag tac gct ccg gca gaa gat ccg ggc gtg gtt tct gta tct gaa      624
Lys Glu Tyr Ala Pro Ala Glu Asp Pro Gly Val Val Ser Val Ser Glu
        195                 200                 205 atc tac cag tac tac aaa gag cac ggt tat gaa acc gtg gtt atg ggc      672
Ile Tyr Gln Tyr Tyr Lys Glu His Gly Tyr Glu Thr Val Val Met Gly
    210                 215                 220 gca agc ttc cgt aac atc ggc gaa att ctg gaa ctg gca ggc tgc gac      720
Ala Ser Phe Arg Asn Ile Gly Glu Ile Leu Glu Leu Ala Gly Cys Asp
225                 230                 235                 240 cgt ctg acc atc gca ccg gca ctg ctg aaa gag ctg gcg gag agc gaa      768
```

-continued

```
                Arg Leu Thr Ile Ala Pro Ala Leu Leu Lys Glu Leu Ala Glu Ser Glu
                                245                 250                 255 ggg gct atc gaa cgt aaa ctg tct tac acc ggc gaa gtg aaa gcg cgt              816
Gly Ala Ile Glu Arg Lys Leu Ser Tyr Thr Gly Glu Val Lys Ala Arg
            260                 265                 270 ccg gcg cgt atc act gag tcc gag ttc ctg tgg cag cac aac cag gat              864
Pro Ala Arg Ile Thr Glu Ser Glu Phe Leu Trp Gln His Asn Gln Asp
        275                 280                 285 cca atg gca gta gat aaa ctg gcg gaa ggt atc cgt aag ttt gct att              912
Pro Met Ala Val Asp Lys Leu Ala Glu Gly Ile Arg Lys Phe Ala Ile
    290                 295                 300 gac cag gaa aaa ctg gaa aaa atg atc ggc gat ctg ctg taa                      954
Asp Gln Glu Lys Leu Glu Lys Met Ile Gly Asp Leu Leu
305                 310                 315
```

<210> SEQ ID NO 10
<211> LENGTH: 317
<212> TYPE: PRT
<213> ORGANISM: Escherichia coli

<400> SEQUENCE: 10

```
Met Thr Asp Lys Leu Thr Ser Leu Arg Gln Tyr Thr Thr Val Val Ala
1               5                   10                  15

Asp Thr Gly Asp Ile Ala Ala Met Lys Leu Tyr Gln Pro Gln Asp Ala
            20                  25                  30

Thr Thr Asn Pro Ser Leu Ile Leu Asn Ala Ala Gln Ile Pro Glu Tyr
        35                  40                  45

Arg Lys Leu Ile Asp Asp Ala Val Ala Trp Ala Lys Gln Gln Ser Asn
    50                  55                  60

Asp Arg Ala Gln Gln Ile Val Asp Ala Thr Asp Lys Leu Ala Val Asn
65                  70                  75                  80

Ile Gly Leu Glu Ile Leu Lys Leu Val Pro Gly Arg Ile Ser Thr Glu
                85                  90                  95

Val Asp Ala Arg Leu Ser Tyr Asp Thr Glu Ala Ser Ile Ala Lys Ala
            100                 105                 110

Lys Arg Leu Ile Lys Leu Tyr Asn Asp Ala Gly Ile Ser Asn Asp Arg
        115                 120                 125

Ile Leu Ile Lys Leu Ala Ser Thr Trp Gln Gly Ile Arg Ala Ala Glu
    130                 135                 140

Gln Leu Glu Lys Glu Gly Ile Asn Cys Asn Leu Thr Leu Leu Phe Ser
145                 150                 155                 160

Phe Ala Gln Ala Arg Ala Cys Ala Glu Ala Gly Val Phe Leu Ile Ser
                165                 170                 175

Pro Phe Val Gly Arg Ile Leu Asp Trp Tyr Lys Ala Asn Thr Asp Lys
            180                 185                 190

Lys Glu Tyr Ala Pro Ala Glu Asp Pro Gly Val Val Ser Val Ser Glu
        195                 200                 205

Ile Tyr Gln Tyr Tyr Lys Glu His Gly Tyr Glu Thr Val Val Met Gly
    210                 215                 220

Ala Ser Phe Arg Asn Ile Gly Glu Ile Leu Glu Leu Ala Gly Cys Asp
225                 230                 235                 240

Arg Leu Thr Ile Ala Pro Ala Leu Leu Lys Glu Leu Ala Glu Ser Glu
                245                 250                 255

Gly Ala Ile Glu Arg Lys Leu Ser Tyr Thr Gly Glu Val Lys Ala Arg
            260                 265                 270

Pro Ala Arg Ile Thr Glu Ser Glu Phe Leu Trp Gln His Asn Gln Asp
```

```
                275                 280                 285
        Pro Met Ala Val Asp Lys Leu Ala Glu Gly Ile Arg Lys Phe Ala Ile
            290                 295                 300

Asp Gln Glu Lys Leu Glu Lys Met Ile Gly Asp Leu Leu
        305                 310                 315

<210> SEQ ID NO 11
<211> LENGTH: 1992
<212> TYPE: DNA
<213> ORGANISM: Escherichia coli
<220> FEATURE:
<221> NAME/KEY: CDS
<222> LOCATION: (1)..(1992)

<400> SEQUENCE: 11 atg tcc tca cgt aaa gag ctt gcc aat gct att cgt gcg ctg agc atg      48
Met Ser Ser Arg Lys Glu Leu Ala Asn Ala Ile Arg Ala Leu Ser Met
1               5                   10                  15 gac gca gta cag aaa gcc aaa tcc ggt cac ccg ggt gcc cct atg ggt      96
Asp Ala Val Gln Lys Ala Lys Ser Gly His Pro Gly Ala Pro Met Gly
                20                  25                  30 atg gct gac att gcc gaa gtc ctg tgg cgt gat ttc ctg aaa cac aac     144
Met Ala Asp Ile Ala Glu Val Leu Trp Arg Asp Phe Leu Lys His Asn
            35                  40                  45 ccg cag aat ccg tcc tgg gct gac cgt gac cgc ttc gtg ctg tcc aac     192
Pro Gln Asn Pro Ser Trp Ala Asp Arg Asp Arg Phe Val Leu Ser Asn
        50                  55                  60 ggc cac ggc tcc atg ctg atc tac agc ctg ctg cac ctc acc ggt tac     240
Gly His Gly Ser Met Leu Ile Tyr Ser Leu Leu His Leu Thr Gly Tyr
65                  70                  75                  80 gat ctg ccg atg gaa gaa ctg aaa aac ttc cgt cag ctg cac tct aaa     288
Asp Leu Pro Met Glu Glu Leu Lys Asn Phe Arg Gln Leu His Ser Lys
                85                  90                  95 act ccg ggt cac ccg gaa gtg ggt tac acc gct ggt gtg gaa acc acc     336
Thr Pro Gly His Pro Glu Val Gly Tyr Thr Ala Gly Val Glu Thr Thr
                100                 105                 110 acc ggt ccg ctg ggt cag ggt att gcc aac gca gtc ggt atg gcg att     384
Thr Gly Pro Leu Gly Gln Gly Ile Ala Asn Ala Val Gly Met Ala Ile
            115                 120                 125 gca gaa aaa acg ctg gcg gcg cag ttt aac cgt ccg ggc cac gac att     432
Ala Glu Lys Thr Leu Ala Ala Gln Phe Asn Arg Pro Gly His Asp Ile
        130                 135                 140 gtc gac cac tac acc tac gcc ttc atg ggc gac ggc tgc atg atg gaa     480
Val Asp His Tyr Thr Tyr Ala Phe Met Gly Asp Gly Cys Met Met Glu
145                 150                 155                 160 ggc atc tcc cac gaa gtt tgc tct ctg gcg ggt acg ctg aag ctg ggt     528
Gly Ile Ser His Glu Val Cys Ser Leu Ala Gly Thr Leu Lys Leu Gly
                165                 170                 175 aaa ctg att gca ttc tac gat gac aac ggt att tct atc gat ggt cac     576
Lys Leu Ile Ala Phe Tyr Asp Asp Asn Gly Ile Ser Ile Asp Gly His
                180                 185                 190 gtt gaa ggc tgg ttc acc gac gac acc gca atg cgt ttc gaa gct tac     624
Val Glu Gly Trp Phe Thr Asp Asp Thr Ala Met Arg Phe Glu Ala Tyr
            195                 200                 205 ggc tgg cac gtt att cgc gac atc gac ggt cat gac gcg gca tct atc     672
Gly Trp His Val Ile Arg Asp Ile Asp Gly His Asp Ala Ala Ser Ile
        210                 215                 220 aaa cgc gca gta gaa gaa gcg cgc gca gtg act gac aaa cct tcc ctg     720
Lys Arg Ala Val Glu Glu Ala Arg Ala Val Thr Asp Lys Pro Ser Leu
225                 230                 235                 240
```

|   |   |
|---|---|
| ctg atg tgc aaa acc atc atc ggt ttc ggt tcc ccg aac aaa gcc ggt<br>Leu Met Cys Lys Thr Ile Ile Gly Phe Gly Ser Pro Asn Lys Ala Gly<br>245 250 255 | 768 |
| acc cac gac tcc cac ggt gcg ccg ctg ggc gac gct gaa att gcc ctg<br>Thr His Asp Ser His Gly Ala Pro Leu Gly Asp Ala Glu Ile Ala Leu<br>260 265 270 | 816 |
| acc cgc gaa caa ctg ggc tgg aaa tat gcg ccg ttc gaa atc ccg tct<br>Thr Arg Glu Gln Leu Gly Trp Lys Tyr Ala Pro Phe Glu Ile Pro Ser<br>275 280 285 | 864 |
| gaa atc tat gct cag tgg gat gcg aaa gaa gca ggc cag gcg aaa gaa<br>Glu Ile Tyr Ala Gln Trp Asp Ala Lys Glu Ala Gly Gln Ala Lys Glu<br>290 295 300 | 912 |
| tcc gca tgg aac gag aaa ttc gct gct tac gcg aaa gct tat ccg cag<br>Ser Ala Trp Asn Glu Lys Phe Ala Ala Tyr Ala Lys Ala Tyr Pro Gln<br>305 310 315 320 | 960 |
| gaa gcc gct gaa ttt acc cgc cgt atg aaa ggc gaa atg ccg tct gac<br>Glu Ala Ala Glu Phe Thr Arg Arg Met Lys Gly Glu Met Pro Ser Asp<br>325 330 335 | 1008 |
| ttc gac gct aaa gcg aaa gag ttc atc gct aaa ctg cag gct aat ccg<br>Phe Asp Ala Lys Ala Lys Glu Phe Ile Ala Lys Leu Gln Ala Asn Pro<br>340 345 350 | 1056 |
| gcg aaa atc gcc agc cgt aaa gcg tct cag aat gct atc gaa gcg ttc<br>Ala Lys Ile Ala Ser Arg Lys Ala Ser Gln Asn Ala Ile Glu Ala Phe<br>355 360 365 | 1104 |
| ggt ccg ctg ttg ccg gaa ttc ctc ggc ggt tct gct gac ctg gcg ccg<br>Gly Pro Leu Leu Pro Glu Phe Leu Gly Gly Ser Ala Asp Leu Ala Pro<br>370 375 380 | 1152 |
| tct aac ctg acc ctg tgg tct ggt tct aaa gca atc aac gaa gat gct<br>Ser Asn Leu Thr Leu Trp Ser Gly Ser Lys Ala Ile Asn Glu Asp Ala<br>385 390 395 400 | 1200 |
| gcg ggt aac tac atc cac tac ggt gtt cgc gag ttc ggt atg acc gcg<br>Ala Gly Asn Tyr Ile His Tyr Gly Val Arg Glu Phe Gly Met Thr Ala<br>405 410 415 | 1248 |
| att gct aac ggt atc tcc ctg cac ggt ggc ttc ctg ccg tac acc tcc<br>Ile Ala Asn Gly Ile Ser Leu His Gly Gly Phe Leu Pro Tyr Thr Ser<br>420 425 430 | 1296 |
| acc ttc ctg atg ttc gtg gaa tac gca cgt aac gcc gta cgt atg gct<br>Thr Phe Leu Met Phe Val Glu Tyr Ala Arg Asn Ala Val Arg Met Ala<br>435 440 445 | 1344 |
| gcg ctg atg aaa cag cgt cag gtg atg gtt tac acc cac gac tcc atc<br>Ala Leu Met Lys Gln Arg Gln Val Met Val Tyr Thr His Asp Ser Ile<br>450 455 460 | 1392 |
| ggt ctg ggc gaa gac ggc ccg act cac cag ccg gtt gag cag gtc gct<br>Gly Leu Gly Glu Asp Gly Pro Thr His Gln Pro Val Glu Gln Val Ala<br>465 470 475 480 | 1440 |
| tct ctg cgc gta acc ccg aac atg tct aca tgg cgt ccg tgt gac cag<br>Ser Leu Arg Val Thr Pro Asn Met Ser Thr Trp Arg Pro Cys Asp Gln<br>485 490 495 | 1488 |
| gtt gaa tcc gcg gtc gcg tgg aaa tac ggt gtt gag cgt cag gac ggc<br>Val Glu Ser Ala Val Ala Trp Lys Tyr Gly Val Glu Arg Gln Asp Gly<br>500 505 510 | 1536 |
| ccg acc gca ctg atc ctc tcc cgt cag aac ctg gcg cag cag gaa cga<br>Pro Thr Ala Leu Ile Leu Ser Arg Gln Asn Leu Ala Gln Gln Glu Arg<br>515 520 525 | 1584 |
| act gaa gag caa ctg gca aac atc gcg cgc ggt ggt tat gtg ctg aaa<br>Thr Glu Glu Gln Leu Ala Asn Ile Ala Arg Gly Gly Tyr Val Leu Lys<br>530 535 540 | 1632 |
| gac tgc gcc ggt cag ccg gaa ctg att ttc atc gct acc ggt tca gaa<br>Asp Cys Ala Gly Gln Pro Glu Leu Ile Phe Ile Ala Thr Gly Ser Glu<br>545 550 555 560 | 1680 |

```
gtt gaa ctg gct gtt gct gcc tac gaa aaa ctg act gcc gaa ggc gtg      1728
Val Glu Leu Ala Val Ala Ala Tyr Glu Lys Leu Thr Ala Glu Gly Val
                565                 570                 575 aaa gcg cgc gtg gtg tcc atg ccg tct acc gac gca ttt gac aag cag      1776
Lys Ala Arg Val Val Ser Met Pro Ser Thr Asp Ala Phe Asp Lys Gln
            580                 585                 590 gat gct gct tac cgt gaa tcc gta ctg ccg aaa gcg gtt act gca cgc      1824
Asp Ala Ala Tyr Arg Glu Ser Val Leu Pro Lys Ala Val Thr Ala Arg
        595                 600                 605 gtt gct gta gaa gcg ggt att gct gac tac tgg tac aag tat gtt ggc      1872
Val Ala Val Glu Ala Gly Ile Ala Asp Tyr Trp Tyr Lys Tyr Val Gly
    610                 615                 620 ctg aac ggt gct atc gtc ggt atg acc acc ttc ggt gaa tct gct ccg      1920
Leu Asn Gly Ala Ile Val Gly Met Thr Thr Phe Gly Glu Ser Ala Pro
625                 630                 635                 640 gca gag ctg ctg ttt gaa gag ttc ggc ttc act gtt gat aac gtt gtt      1968
Ala Glu Leu Leu Phe Glu Glu Phe Gly Phe Thr Val Asp Asn Val Val
                645                 650                 655 gcg aaa gca aaa gaa ctg ctg taa                                      1992
Ala Lys Ala Lys Glu Leu Leu
            660

<210> SEQ ID NO 12
<211> LENGTH: 663
<212> TYPE: PRT
<213> ORGANISM: Escherichia coli

<400> SEQUENCE: 12

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
            20                  25                  30

Met Ala Asp Ile Ala Glu Val Leu Trp Arg Asp Phe Leu Lys His Asn
        35                  40                  45

Pro Gln Asn Pro Ser Trp Ala Asp Arg Asp Arg Phe Val Leu Ser Asn
    50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
            100                 105                 110

Thr Gly Pro Leu Gly Gln Gly Ile Ala Asn Ala Val Gly Met Ala Ile
        115                 120                 125

Ala Glu Lys Thr Leu Ala Ala Gln Phe Asn Arg Pro Gly His Asp Ile
    130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
            180                 185                 190

Val Glu Gly Trp Phe Thr Asp Thr Ala Met Arg Phe Glu Ala Tyr
        195                 200                 205

Gly Trp His Val Ile Arg Asp Ile Asp Gly His Asp Ala Ala Ser Ile
    210                 215                 220
```

-continued

Lys Arg Ala Val Glu Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
            245                 250                 255

Thr His Asp Ser His Gly Ala Pro Leu Gly Asp Ala Glu Ile Ala Leu
            260                 265                 270

Thr Arg Glu Gln Leu Gly Trp Lys Tyr Ala Pro Phe Glu Ile Pro Ser
            275                 280                 285

Glu Ile Tyr Ala Gln Trp Asp Ala Lys Glu Ala Gly Gln Ala Lys Glu
        290                 295                 300

Ser Ala Trp Asn Glu Lys Phe Ala Ala Tyr Ala Lys Ala Tyr Pro Gln
305                 310                 315                 320

Glu Ala Ala Glu Phe Thr Arg Arg Met Lys Gly Glu Met Pro Ser Asp
                325                 330                 335

Phe Asp Ala Lys Ala Lys Glu Phe Ile Ala Lys Leu Gln Ala Asn Pro
            340                 345                 350

Ala Lys Ile Ala Ser Arg Lys Ala Ser Gln Asn Ala Ile Glu Ala Phe
        355                 360                 365

Gly Pro Leu Leu Pro Glu Phe Leu Gly Gly Ser Ala Asp Leu Ala Pro
370                 375                 380

Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
                405                 410                 415

Ile Ala Asn Gly Ile Ser Leu His Gly Gly Phe Leu Pro Tyr Thr Ser
            420                 425                 430

Thr Phe Leu Met Phe Val Glu Tyr Ala Arg Asn Ala Val Arg Met Ala
        435                 440                 445

Ala Leu Met Lys Gln Arg Gln Val Met Val Tyr Thr His Asp Ser Ile
450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
                485                 490                 495

Val Glu Ser Ala Val Ala Trp Lys Tyr Gly Val Glu Arg Gln Asp Gly
            500                 505                 510

Pro Thr Ala Leu Ile Leu Ser Arg Gln Asn Leu Ala Gln Gln Glu Arg
        515                 520                 525

Thr Glu Glu Gln Leu Ala Asn Ile Ala Arg Gly Gly Tyr Val Leu Lys
530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
                565                 570                 575

Lys Ala Arg Val Val Ser Met Pro Ser Thr Asp Ala Phe Asp Lys Gln
            580                 585                 590

Asp Ala Ala Tyr Arg Glu Ser Val Leu Pro Lys Ala Val Thr Ala Arg
        595                 600                 605

Val Ala Val Glu Ala Gly Ile Ala Asp Tyr Trp Tyr Lys Tyr Val Gly
610                 615                 620

Leu Asn Gly Ala Ile Val Gly Met Thr Thr Phe Gly Glu Ser Ala Pro
625                 630                 635                 640

Ala Glu Leu Leu Phe Glu Glu Phe Gly Phe Thr Val Asp Asn Val Val

Ala Lys Ala Lys Glu Leu Leu
             660

<210> SEQ ID NO 13
<211> LENGTH: 633
<212> TYPE: DNA
<213> ORGANISM: Bacillus subtilis
<220> FEATURE:
<221> NAME/KEY: CDS
<222> LOCATION: (1)..(633)

<400> SEQUENCE: 13

```
atg gaa tta cag ctt gca tta gac ctc gtc aac atc cca gaa gcc att    48
Met Glu Leu Gln Leu Ala Leu Asp Leu Val Asn Ile Pro Glu Ala Ile
1               5                   10                  15 gag ctc gtc aaa gag gta gaa caa tac atc gac gta gtt gaa atc gga    96
Glu Leu Val Lys Glu Val Glu Gln Tyr Ile Asp Val Val Glu Ile Gly
            20                  25                  30 aca ccg gtc gtc att aat gaa ggc cta aga gcc gtt aaa gaa tta aaa   144
Thr Pro Val Val Ile Asn Glu Gly Leu Arg Ala Val Lys Glu Leu Lys
        35                  40                  45 gaa gca ttt cct caa ttg aag gtt ctt gca gac ctg aaa atc atg gat   192
Glu Ala Phe Pro Gln Leu Lys Val Leu Ala Asp Leu Lys Ile Met Asp
 50                  55                  60 gcc gga ggc tac gaa att atg aaa gcg tcg gaa gca ggc gct gac atc   240
Ala Gly Gly Tyr Glu Ile Met Lys Ala Ser Glu Ala Gly Ala Asp Ile
 65                  70                  75                  80 atc acc gtt tta ggg gct aca gac gac gca acg att aaa ggc gca gta   288
Ile Thr Val Leu Gly Ala Thr Asp Asp Ala Thr Ile Lys Gly Ala Val
                 85                  90                  95 gaa gaa gcc aaa aaa caa aag aag aaa atc tta gtg gac atg att aac   336
Glu Glu Ala Lys Lys Gln Lys Lys Lys Ile Leu Val Asp Met Ile Asn
            100                 105                 110 gtg aaa gat atc gag tcc cgt gcg caa gaa att gac gca ctc ggt gtt   384
Val Lys Asp Ile Glu Ser Arg Ala Gln Glu Ile Asp Ala Leu Gly Val
        115                 120                 125 gac tac atc tgc gtc cac act ggc tat gat ctt caa gca gag ggc aag   432
Asp Tyr Ile Cys Val His Thr Gly Tyr Asp Leu Gln Ala Glu Gly Lys
    130                 135                 140 aac tct ttc gaa gaa tta acg aca atc aaa aac acc gta aaa aac gca   480
Asn Ser Phe Glu Glu Leu Thr Thr Ile Lys Asn Thr Val Lys Asn Ala
145                 150                 155                 160 aaa acc gca atc gcg ggc ggc atc aaa ctt gat aca ctg cca gaa gtg   528
Lys Thr Ala Ile Ala Gly Gly Ile Lys Leu Asp Thr Leu Pro Glu Val
                165                 170                 175 atc aag caa aac ccc gac ctt gtc att gtt ggg ggc gga att aca agc   576
Ile Lys Gln Asn Pro Asp Leu Val Ile Val Gly Gly Gly Ile Thr Ser
            180                 185                 190 gca gct gat aag gca gaa aca gct tca aaa atg aag cag ctg att gtc   624
Ala Ala Asp Lys Ala Glu Thr Ala Ser Lys Met Lys Gln Leu Ile Val
        195                 200                 205 caa gga taa                                                       633
Gln Gly
    210
```

<210> SEQ ID NO 14
<211> LENGTH: 210
<212> TYPE: PRT
<213> ORGANISM: Bacillus subtilis

<400> SEQUENCE: 14

```
Met Glu Leu Gln Leu Ala Leu Asp Leu Val Asn Ile Pro Glu Ala Ile
1               5                   10                  15

Glu Leu Val Lys Glu Val Glu Gln Tyr Ile Asp Val Glu Ile Gly
            20                  25                  30

Thr Pro Val Val Ile Asn Glu Gly Leu Arg Ala Val Lys Glu Leu Lys
        35                  40                  45

Glu Ala Phe Pro Gln Leu Lys Val Leu Ala Asp Leu Lys Ile Met Asp
50                  55                  60

Ala Gly Gly Tyr Glu Ile Met Lys Ala Ser Glu Ala Gly Ala Asp Ile
65                  70                  75                  80

Ile Thr Val Leu Gly Ala Thr Asp Ala Thr Ile Lys Gly Ala Val
                85                  90                  95

Glu Glu Ala Lys Lys Gln Lys Lys Lys Ile Leu Val Asp Met Ile Asn
            100                 105                 110

Val Lys Asp Ile Glu Ser Arg Ala Gln Glu Ile Asp Ala Leu Gly Val
        115                 120                 125

Asp Tyr Ile Cys Val His Thr Gly Tyr Asp Leu Gln Ala Glu Gly Lys
    130                 135                 140

Asn Ser Phe Glu Glu Leu Thr Thr Ile Lys Asn Thr Val Lys Asn Ala
145                 150                 155                 160

Lys Thr Ala Ile Ala Gly Gly Ile Lys Leu Asp Thr Leu Pro Glu Val
                165                 170                 175

Ile Lys Gln Asn Pro Asp Leu Val Ile Val Gly Gly Ile Thr Ser
            180                 185                 190

Ala Ala Asp Lys Ala Glu Thr Ala Ser Lys Met Lys Gln Leu Ile Val
        195                 200                 205

Gln Gly
    210

<210> SEQ ID NO 15
<211> LENGTH: 687
<212> TYPE: DNA
<213> ORGANISM: Methylobacillus flagellatus
<220> FEATURE:
<221> NAME/KEY: CDS
<222> LOCATION: (1)..(687)

<400> SEQUENCE: 15 gtg gca aaa cca tta gtt caa atg gca tta gat tca cta gat ttc gat     48
Val Ala Lys Pro Leu Val Gln Met Ala Leu Asp Ser Leu Asp Phe Asp
1               5                   10                  15 cag act gta gcg ctt gct acg act gtt gca cca cat gtt gat att ctt     96
Gln Thr Val Ala Leu Ala Thr Thr Val Ala Pro His Val Asp Ile Leu
            20                  25                  30 gaa atc ggt act cct tgt atc aag tac aac ggt atc aag ttg ctg gag   144
Glu Ile Gly Thr Pro Cys Ile Lys Tyr Asn Gly Ile Lys Leu Leu Glu
        35                  40                  45 act ctc cgc gca aag ttc cct aac aac aag atc ctg gtt gac ctg aag   192
Thr Leu Arg Ala Lys Phe Pro Asn Asn Lys Ile Leu Val Asp Leu Lys
50                  55                  60 acc atg gat gct ggt ttt tac gaa gca gag cct ttc tac aag gca ggt   240
Thr Met Asp Ala Gly Phe Tyr Glu Ala Glu Pro Phe Tyr Lys Ala Gly
65                  70                  75                  80 gcc gac atc gtg acc gtg ctc ggc act gct gac att ggc acg atc aaa   288
Ala Asp Ile Val Thr Val Leu Gly Thr Ala Asp Ile Gly Thr Ile Lys
                85                  90                  95 ggc gtc att gat gtt gcc aac aaa tac ggc aag aag gct caa gtc gac   336
```

```
                                                                              384
ctg atc aac gtg act gac aag gct gca cgc acc aag gaa gtg gcc aag
Leu Ile Asn Val Thr Asp Lys Ala Ala Arg Thr Lys Glu Val Ala Lys
        115                 120                 125

432
ctc ggc gct cac atc att ggc gtt cac act ggt ttg gat caa cag gct
Leu Gly Ala His Ile Ile Gly Val His Thr Gly Leu Asp Gln Gln Ala
130                 135                 140

480
gct ggt cag aca ccg ttt gcc gat ctc aac ctt gtt tcc agc ctg aac
Ala Gly Gln Thr Pro Phe Ala Asp Leu Asn Leu Val Ser Ser Leu Asn
145                 150                 155                 160

528
ctg ggt gtt gac att tcc gta gct ggt ggc gtg aag gcg act acc gcc
Leu Gly Val Asp Ile Ser Val Ala Gly Gly Val Lys Ala Thr Thr Ala
                165                 170                 175

576
aaa caa gtg gtt gat gca ggt gcc aca att gtt gtt gct ggt gcg gct
Lys Gln Val Val Asp Ala Gly Ala Thr Ile Val Val Ala Gly Ala Ala
            180                 185                 190

624
atc tat ggt gct gcc gat cct gct gct gct gct gaa atc agc gct
Ile Tyr Gly Ala Ala Asp Pro Ala Ala Ala Ala Glu Ile Ser Ala
        195                 200                 205

672
gcg gcc aag ggt aca caa agc agt ggt ggc ctg ttt ggc tgg ctg aag
Ala Ala Lys Gly Thr Gln Ser Ser Gly Gly Leu Phe Gly Trp Leu Lys
210                 215                 220

687
aaa ctg ttc agc taa
Lys Leu Phe Ser
225

<210> SEQ ID NO 16
<211> LENGTH: 228
<212> TYPE: PRT
<213> ORGANISM: Methylobacillus flagellatus

<400> SEQUENCE: 16

Val Ala Lys Pro Leu Val Gln Met Ala Leu Asp Ser Leu Asp Phe Asp
1               5                   10                  15

Gln Thr Val Ala Leu Ala Thr Thr Val Ala Pro His Val Asp Ile Leu
            20                  25                  30

Glu Ile Gly Thr Pro Cys Ile Lys Tyr Asn Gly Ile Lys Leu Leu Glu
        35                  40                  45

Thr Leu Arg Ala Lys Phe Pro Asn Asn Lys Ile Leu Val Asp Leu Lys
50                  55                  60

Thr Met Asp Ala Gly Phe Tyr Glu Ala Glu Pro Phe Tyr Lys Ala Gly
65                  70                  75                  80

Ala Asp Ile Val Thr Val Leu Gly Thr Ala Asp Ile Gly Thr Ile Lys
                85                  90                  95

Gly Val Ile Asp Val Ala Asn Lys Tyr Gly Lys Lys Ala Gln Val Asp
            100                 105                 110

Leu Ile Asn Val Thr Asp Lys Ala Ala Arg Thr Lys Glu Val Ala Lys
        115                 120                 125

Leu Gly Ala His Ile Ile Gly Val His Thr Gly Leu Asp Gln Gln Ala
130                 135                 140

Ala Gly Gln Thr Pro Phe Ala Asp Leu Asn Leu Val Ser Ser Leu Asn
145                 150                 155                 160

Leu Gly Val Asp Ile Ser Val Ala Gly Gly Val Lys Ala Thr Thr Ala
                165                 170                 175

Lys Gln Val Val Asp Ala Gly Ala Thr Ile Val Val Ala Gly Ala Ala
            180                 185                 190
```

```
Ile Tyr Gly Ala Ala Asp Pro Ala Ala Ala Ala Glu Ile Ser Ala
            195                 200                 205

Ala Ala Lys Gly Thr Gln Ser Ser Gly Gly Leu Phe Gly Trp Leu Lys
    210                 215                 220

Lys Leu Phe Ser
225

<210> SEQ ID NO 17
<211> LENGTH: 2121
<212> TYPE: DNA
<213> ORGANISM: Candida boidinii
<220> FEATURE:
<221> NAME/KEY: CDS
<222> LOCATION: (1)..(2121)

<400> SEQUENCE: 17 atg gct ctc gca aaa gct gct tca att aac gat gat atc cat gat tta        48
Met Ala Leu Ala Lys Ala Ala Ser Ile Asn Asp Asp Ile His Asp Leu
1               5                   10                  15 aca atg aga gca ttc cgt tgt tat gtc ttg gat tta gtt gaa caa tat       96
Thr Met Arg Ala Phe Arg Cys Tyr Val Leu Asp Leu Val Glu Gln Tyr
                20                  25                  30 gaa ggt ggt cat cct ggt tct gct atg ggt atg gtt gcc atg ggt att      144
Glu Gly Gly His Pro Gly Ser Ala Met Gly Met Val Ala Met Gly Ile
            35                  40                  45 gca tta tgg aaa tat aca atg aaa tat tct aca aat gat cca aca tgg      192
Ala Leu Trp Lys Tyr Thr Met Lys Tyr Ser Thr Asn Asp Pro Thr Trp
        50                  55                  60 ttc aat cgt gat aga ttt gtt tta tca aat ggt cat gtt tgt tta ttt      240
Phe Asn Arg Asp Arg Phe Val Leu Ser Asn Gly His Val Cys Leu Phe
65                  70                  75                  80 caa tat tta ttt caa cat tta tca ggt ttg aaa tct atg act gaa aag      288
Gln Tyr Leu Phe Gln His Leu Ser Gly Leu Lys Ser Met Thr Glu Lys
                85                  90                  95 caa tta aaa tct tat cat tca tca gat tac cat tct aaa tgt cct gga      336
Gln Leu Lys Ser Tyr His Ser Ser Asp Tyr His Ser Lys Cys Pro Gly
            100                 105                 110 cat cca gaa att gaa aat gaa gct gtt gaa gtt act act ggt cca tta      384
His Pro Glu Ile Glu Asn Glu Ala Val Glu Val Thr Thr Gly Pro Leu
        115                 120                 125 ggt caa ggt att tct aat tct gtt ggt tta gct att gca tct aaa aat      432
Gly Gln Gly Ile Ser Asn Ser Val Gly Leu Ala Ile Ala Ser Lys Asn
    130                 135                 140 ttg ggt gca tta tat aac aag cca gga tat gaa gtt gtt aat aat act      480
Leu Gly Ala Leu Tyr Asn Lys Pro Gly Tyr Glu Val Val Asn Asn Thr
145                 150                 155                 160 aca tat tgt att gtt ggt gat gct tgt tta caa gaa ggt cca gca tta      528
Thr Tyr Cys Ile Val Gly Asp Ala Cys Leu Gln Glu Gly Pro Ala Leu
                165                 170                 175 gaa tct att tca ttt gca ggt cat tta gga tta gat aat tta gtt gtt      576
Glu Ser Ile Ser Phe Ala Gly His Leu Gly Leu Asp Asn Leu Val Val
            180                 185                 190 att tat gat aac aat caa gtt tgt tgt gat ggt tct gtt gat att gct      624
Ile Tyr Asp Asn Asn Gln Val Cys Cys Asp Gly Ser Val Asp Ile Ala
        195                 200                 205 aat act gaa gat att tca gct aag ttt aga gct tgt aat tgg aat gtt      672
Asn Thr Glu Asp Ile Ser Ala Lys Phe Arg Ala Cys Asn Trp Asn Val
    210                 215                 220 att gaa gtt gaa gat ggt gct aga gat gtt gct act att gtc aag gca      720
Ile Glu Val Glu Asp Gly Ala Arg Asp Val Ala Thr Ile Val Lys Ala
225                 230                 235                 240
```

```
ttg gaa cta gct ggt gct gaa aag aat aga cca aca tta att aat gtt      768
Leu Glu Leu Ala Gly Ala Glu Lys Asn Arg Pro Thr Leu Ile Asn Val
                245                 250                 255 cgt act att att ggt act gat tca gct ttc caa aat cat tgt gct gct      816
Arg Thr Ile Ile Gly Thr Asp Ser Ala Phe Gln Asn His Cys Ala Ala
            260                 265                 270 cat ggt agt gct tta ggt gaa gaa ggt att aga gaa ttg aaa atc aaa      864
His Gly Ser Ala Leu Gly Glu Glu Gly Ile Arg Glu Leu Lys Ile Lys
        275                 280                 285 tat ggt ttt aat cca tct caa aaa ttc cat ttt cca caa gaa gtt tat      912
Tyr Gly Phe Asn Pro Ser Gln Lys Phe His Phe Pro Gln Glu Val Tyr
    290                 295                 300 gat ttc ttt agt gat att cca gct aaa ggt gac gaa tat gtt tct aat      960
Asp Phe Phe Ser Asp Ile Pro Ala Lys Gly Asp Glu Tyr Val Ser Asn
305                 310                 315                 320 tgg aat aaa tta gtt agt agt tat gtt aaa gaa ttt cct gaa tta gga     1008
Trp Asn Lys Leu Val Ser Ser Tyr Val Lys Glu Phe Pro Glu Leu Gly
                325                 330                 335 gct gaa ttt caa tca aga gtt aaa ggt gaa tta cca aag aat tgg aaa     1056
Ala Glu Phe Gln Ser Arg Val Lys Gly Glu Leu Pro Lys Asn Trp Lys
            340                 345                 350 tca tta tta cca aat aat tta cca aat gaa gat aca gca aca aga aca     1104
Ser Leu Leu Pro Asn Asn Leu Pro Asn Glu Asp Thr Ala Thr Arg Thr
        355                 360                 365 tca gct aga gct atg gtt aga gca tta gct aaa gat gtt cca aat gtt     1152
Ser Ala Arg Ala Met Val Arg Ala Leu Ala Lys Asp Val Pro Asn Val
    370                 375                 380 att gct ggt tca gca gat tta tca gtt tcg gtt aat tta cca tgg cct     1200
Ile Ala Gly Ser Ala Asp Leu Ser Val Ser Val Asn Leu Pro Trp Pro
385                 390                 395                 400 gga tct aaa tat ttt gaa aat cca caa tta gca aca caa tgt gga tta     1248
Gly Ser Lys Tyr Phe Glu Asn Pro Gln Leu Ala Thr Gln Cys Gly Leu
                405                 410                 415 gct ggt gat tat tct ggt aga tat gtt gaa ttt ggt att aga gaa cat     1296
Ala Gly Asp Tyr Ser Gly Arg Tyr Val Glu Phe Gly Ile Arg Glu His
            420                 425                 430 tgt atg tgt gct att gct aat ggt tta gct gct ttt aac aaa ggt aca     1344
Cys Met Cys Ala Ile Ala Asn Gly Leu Ala Ala Phe Asn Lys Gly Thr
        435                 440                 445 ttt tta cca att act tca tca ttt tat atg ttt tat ctc tat gca gcc     1392
Phe Leu Pro Ile Thr Ser Ser Phe Tyr Met Phe Tyr Leu Tyr Ala Ala
    450                 455                 460 cca gca tta aga atg gct gca tta caa gaa tta aag gca att cat att     1440
Pro Ala Leu Arg Met Ala Ala Leu Gln Glu Leu Lys Ala Ile His Ile
465                 470                 475                 480 gct aca cat gat tct att ggt gct ggt gaa gat gga cca aca cat caa     1488
Ala Thr His Asp Ser Ile Gly Ala Gly Glu Asp Gly Pro Thr His Gln
                485                 490                 495 cct att gca caa tct gct tta tgg aga gca atg cct aat ttc tat tat     1536
Pro Ile Ala Gln Ser Ala Leu Trp Arg Ala Met Pro Asn Phe Tyr Tyr
            500                 505                 510 atg aga cca ggt gat gct agt gaa gta cgt gga tta ttt gaa aaa gct     1584
Met Arg Pro Gly Asp Ala Ser Glu Val Arg Gly Leu Phe Glu Lys Ala
        515                 520                 525 gtt gaa tta cca tta tct aca tta ttt tca tta tct aga cat gaa gtt     1632
Val Glu Leu Pro Leu Ser Thr Leu Phe Ser Leu Ser Arg His Glu Val
    530                 535                 540 cca caa tat cca ggt aaa tca agt att gaa tta gct aaa aga ggt ggt     1680
Pro Gln Tyr Pro Gly Lys Ser Ser Ile Glu Leu Ala Lys Arg Gly Gly
```

```
                        545                 550                 555                 560
tat gta ttt gaa gat gct aaa gat gct gat att caa tta att ggt gct      1728
Tyr Val Phe Glu Asp Ala Lys Asp Ala Asp Ile Gln Leu Ile Gly Ala
                565                 570                 575 ggt tca gaa tta gaa caa gct gtt aaa act gct aga att tta aga tct      1776
Gly Ser Glu Leu Glu Gln Ala Val Lys Thr Ala Arg Ile Leu Arg Ser
            580                 585                 590 aga gga tta aaa gtt cgt att tta tct ttc cca tgt caa cgt tta ttt      1824
Arg Gly Leu Lys Val Arg Ile Leu Ser Phe Pro Cys Gln Arg Leu Phe
        595                 600                 605 gat gaa caa tct gtt gga tat aga aga tct gtt tta caa agg ggt aaa      1872
Asp Glu Gln Ser Val Gly Tyr Arg Arg Ser Val Leu Gln Arg Gly Lys
    610                 615                 620 gtt cca act gtt gtt att gaa gct tat gtt gct tat ggt tgg gaa aga      1920
Val Pro Thr Val Val Ile Glu Ala Tyr Val Ala Tyr Gly Trp Glu Arg
625                 630                 635                 640 tat gct aca gca ggt tat act atg aat aca ttt ggt aaa tca tta cct      1968
Tyr Ala Thr Ala Gly Tyr Thr Met Asn Thr Phe Gly Lys Ser Leu Pro
                645                 650                 655 gtt gaa gat gtt tat gaa tat ttt ggt ttt aac cca tct gaa att tct      2016
Val Glu Asp Val Tyr Glu Tyr Phe Gly Phe Asn Pro Ser Glu Ile Ser
            660                 665                 670 aaa aaa att gaa ggt tat gtt aga gca gtt aaa gct aat cct gat tta      2064
Lys Lys Ile Glu Gly Tyr Val Arg Ala Val Lys Ala Asn Pro Asp Leu
        675                 680                 685 tta tat gaa ttt att gat tta acc gaa aaa cca aaa cat gat caa aat      2112
Leu Tyr Glu Phe Ile Asp Leu Thr Glu Lys Pro Lys His Asp Gln Asn
    690                 695                 700 cat tta taa                                                          2121
His Leu
705

<210> SEQ ID NO 18
<211> LENGTH: 706
<212> TYPE: PRT
<213> ORGANISM: Candida boidinii

<400> SEQUENCE: 18

Met Ala Leu Ala Lys Ala Ala Ser Ile Asn Asp Asp Ile His Asp Leu
1               5                   10                  15

Thr Met Arg Ala Phe Arg Cys Tyr Val Leu Asp Leu Val Glu Gln Tyr
            20                  25                  30

Glu Gly Gly His Pro Gly Ser Ala Met Gly Met Val Ala Met Gly Ile
        35                  40                  45

Ala Leu Trp Lys Tyr Thr Met Lys Tyr Ser Thr Asn Asp Pro Thr Trp
    50                  55                  60

Phe Asn Arg Asp Arg Phe Val Leu Ser Asn Gly His Val Cys Leu Phe
65                  70                  75                  80

Gln Tyr Leu Phe Gln His Leu Ser Gly Leu Lys Ser Met Thr Glu Lys
                85                  90                  95

Gln Leu Lys Ser Tyr His Ser Ser Asp Tyr His Ser Lys Cys Pro Gly
            100                 105                 110

His Pro Glu Ile Glu Asn Glu Ala Val Glu Val Thr Thr Gly Pro Leu
        115                 120                 125

Gly Gln Gly Ile Ser Asn Ser Val Gly Leu Ala Ile Ala Ser Lys Asn
    130                 135                 140

Leu Gly Ala Leu Tyr Asn Lys Pro Gly Tyr Glu Val Val Asn Asn Thr
145                 150                 155                 160
```

-continued

Thr Tyr Cys Ile Val Gly Asp Ala Cys Leu Gln Gly Pro Ala Leu
                165                 170                 175

Glu Ser Ile Ser Phe Ala Gly His Leu Gly Leu Asp Asn Leu Val Val
    180                 185                 190

Ile Tyr Asp Asn Asn Gln Val Cys Cys Asp Gly Ser Val Asp Ile Ala
        195                 200                 205

Asn Thr Glu Asp Ile Ser Ala Lys Phe Arg Ala Cys Asn Trp Asn Val
    210                 215                 220

Ile Glu Val Glu Asp Gly Ala Arg Asp Val Ala Thr Ile Val Lys Ala
225                 230                 235                 240

Leu Glu Leu Ala Gly Ala Glu Lys Asn Arg Pro Thr Leu Ile Asn Val
                245                 250                 255

Arg Thr Ile Ile Gly Thr Asp Ser Ala Phe Gln Asn His Cys Ala Ala
                260                 265                 270

His Gly Ser Ala Leu Gly Glu Glu Gly Ile Arg Glu Leu Lys Ile Lys
                275                 280                 285

Tyr Gly Phe Asn Pro Ser Gln Lys Phe His Phe Pro Gln Glu Val Tyr
    290                 295                 300

Asp Phe Phe Ser Asp Ile Pro Ala Lys Gly Asp Glu Tyr Val Ser Asn
305                 310                 315                 320

Trp Asn Lys Leu Val Ser Ser Tyr Val Lys Glu Phe Pro Glu Leu Gly
                325                 330                 335

Ala Glu Phe Gln Ser Arg Val Lys Gly Glu Leu Pro Lys Asn Trp Lys
                340                 345                 350

Ser Leu Leu Pro Asn Asn Leu Pro Asn Glu Asp Thr Ala Thr Arg Thr
            355                 360                 365

Ser Ala Arg Ala Met Val Arg Ala Leu Ala Lys Asp Val Pro Asn Val
370                 375                 380

Ile Ala Gly Ser Ala Asp Leu Ser Val Ser Val Asn Leu Pro Trp Pro
385                 390                 395                 400

Gly Ser Lys Tyr Phe Glu Asn Pro Gln Leu Ala Thr Gln Cys Gly Leu
                405                 410                 415

Ala Gly Asp Tyr Ser Gly Arg Tyr Val Glu Phe Gly Ile Arg Glu His
            420                 425                 430

Cys Met Cys Ala Ile Ala Asn Gly Leu Ala Ala Phe Asn Lys Gly Thr
435                 440                 445

Phe Leu Pro Ile Thr Ser Ser Phe Tyr Met Phe Tyr Leu Tyr Ala Ala
    450                 455                 460

Pro Ala Leu Arg Met Ala Ala Leu Gln Glu Leu Lys Ala Ile His Ile
465                 470                 475                 480

Ala Thr His Asp Ser Ile Gly Ala Gly Glu Asp Gly Pro Thr His Gln
                485                 490                 495

Pro Ile Ala Gln Ser Ala Leu Trp Arg Ala Met Pro Asn Phe Tyr Tyr
            500                 505                 510

Met Arg Pro Gly Asp Ala Ser Glu Val Arg Gly Leu Phe Glu Lys Ala
                515                 520                 525

Val Glu Leu Pro Leu Ser Thr Leu Phe Ser Leu Ser Arg His Glu Val
    530                 535                 540

Pro Gln Tyr Pro Gly Lys Ser Ser Ile Glu Leu Ala Lys Arg Gly Gly
545                 550                 555                 560

Tyr Val Phe Glu Asp Ala Lys Asp Ala Asp Ile Gln Leu Ile Gly Ala
                565                 570                 575

```
Gly Ser Glu Leu Glu Gln Ala Val Lys Thr Ala Arg Ile Leu Arg Ser
            580                 585                 590

Arg Gly Leu Lys Val Arg Ile Leu Ser Phe Pro Cys Gln Arg Leu Phe
        595                 600                 605

Asp Glu Gln Ser Val Gly Tyr Arg Arg Ser Val Leu Gln Arg Gly Lys
        610                 615                 620

Val Pro Thr Val Val Ile Glu Ala Tyr Val Ala Tyr Gly Trp Glu Arg
625                 630                 635                 640

Tyr Ala Thr Ala Gly Tyr Thr Met Asn Thr Phe Gly Lys Ser Leu Pro
                645                 650                 655

Val Glu Asp Val Tyr Glu Tyr Phe Gly Phe Asn Pro Ser Glu Ile Ser
            660                 665                 670

Lys Lys Ile Glu Gly Tyr Val Arg Ala Val Lys Ala Asn Pro Asp Leu
        675                 680                 685

Leu Tyr Glu Phe Ile Asp Leu Thr Glu Lys Pro Lys His Asp Gln Asn
        690                 695                 700

His Leu
705

<210> SEQ ID NO 19
<211> LENGTH: 663
<212> TYPE: DNA
<213> ORGANISM: Salmonella enterica
<220> FEATURE:
<221> NAME/KEY: CDS
<222> LOCATION: (1)..(663)

<400> SEQUENCE: 19 atg gaa ctc tat ctg gat acc gct aac gtg gcg gaa gtt gaa cgt ctg      48
Met Glu Leu Tyr Leu Asp Thr Ala Asn Val Ala Glu Val Glu Arg Leu
1               5                   10                  15 gcg cgc att ttc ccg att gcc ggc gtc acc acc aat cca agc att gtg      96
Ala Arg Ile Phe Pro Ile Ala Gly Val Thr Thr Asn Pro Ser Ile Val
                20                  25                  30 gca gcc agc aaa gaa tct atc tgg gat gtg ctg ccc agg ctg caa aac     144
Ala Ala Ser Lys Glu Ser Ile Trp Asp Val Leu Pro Arg Leu Gln Asn
            35                  40                  45 gcc atc ggc gaa gaa ggc act tta ttt gcg cag acc atg agc cgc gac     192
Ala Ile Gly Glu Glu Gly Thr Leu Phe Ala Gln Thr Met Ser Arg Asp
        50                  55                  60 gcg aaa ggg atg gtg gaa gaa gcc aaa cga ctg aat aac gcc atc ccc     240
Ala Lys Gly Met Val Glu Glu Ala Lys Arg Leu Asn Asn Ala Ile Pro
65                  70                  75                  80 ggc att gtg gtt aaa att ccg gtg acc gcc gaa ggt ctt gca gcg att     288
Gly Ile Val Val Lys Ile Pro Val Thr Ala Glu Gly Leu Ala Ala Ile
                85                  90                  95 aaa ttg ctg aaa aaa gaa ggc atc gtg acg ctg ggc acc gcc gtc tac     336
Lys Leu Leu Lys Lys Glu Gly Ile Val Thr Leu Gly Thr Ala Val Tyr
                100                 105                 110 agc gca tcg cag ggc ctg ctg gcg gcg ctg gcg ggc gca aaa tat gtc     384
Ser Ala Ser Gln Gly Leu Leu Ala Ala Leu Ala Gly Ala Lys Tyr Val
            115                 120                 125 gct ccc tac gtc aac cgc gtt gat gcg cag ggc ggc gat ggc att cgt     432
Ala Pro Tyr Val Asn Arg Val Asp Ala Gln Gly Gly Asp Gly Ile Arg
        130                 135                 140 atg gtt cag gag ctg caa acg cta ctg gaa cat cac gcg ccc gac agc     480
Met Val Gln Glu Leu Gln Thr Leu Leu Glu His His Ala Pro Asp Ser
145                 150                 155                 160 atg gta ctg gcg gcc agc ttt aaa acg ccg cgg cag gcg ctg gat tgc     528
```

```
Met Val Leu Ala Ala Ser Phe Lys Thr Pro Arg Gln Ala Leu Asp Cys
            165                 170                 175 tta ctg gca ggt tgc cag gcg att acc ctt cct tta gat gta gcg caa      576
Leu Leu Ala Gly Cys Gln Ala Ile Thr Leu Pro Leu Asp Val Ala Gln
            180                 185                 190 caa atg ctc aat acg cct gcg gta gag tcg gca ata gag aag ttt gag      624
Gln Met Leu Asn Thr Pro Ala Val Glu Ser Ala Ile Glu Lys Phe Glu
            195                 200                 205 caa gac tgg aaa aac gct ttt ggt aat ctg aac ctg tag                  663
Gln Asp Trp Lys Asn Ala Phe Gly Asn Leu Asn Leu
            210                 215                 220

<210> SEQ ID NO 20
<211> LENGTH: 220
<212> TYPE: PRT
<213> ORGANISM: Salmonella enterica

<400> SEQUENCE: 20

Met Glu Leu Tyr Leu Asp Thr Ala Asn Val Ala Glu Val Glu Arg Leu
1               5                   10                  15

Ala Arg Ile Phe Pro Ile Ala Gly Val Thr Thr Asn Pro Ser Ile Val
                20                  25                  30

Ala Ala Ser Lys Glu Ser Ile Trp Asp Val Leu Pro Arg Leu Gln Asn
            35                  40                  45

Ala Ile Gly Glu Glu Gly Thr Leu Phe Ala Gln Thr Met Ser Arg Asp
        50                  55                  60

Ala Lys Gly Met Val Glu Glu Ala Lys Arg Leu Asn Asn Ala Ile Pro
65                  70                  75                  80

Gly Ile Val Val Lys Ile Pro Val Thr Ala Glu Gly Leu Ala Ala Ile
                85                  90                  95

Lys Leu Leu Lys Lys Glu Gly Ile Val Thr Leu Gly Thr Ala Val Tyr
            100                 105                 110

Ser Ala Ser Gln Gly Leu Leu Ala Ala Leu Ala Gly Ala Lys Tyr Val
            115                 120                 125

Ala Pro Tyr Val Asn Arg Val Asp Ala Gln Gly Gly Asp Gly Ile Arg
        130                 135                 140

Met Val Gln Glu Leu Gln Thr Leu Leu Glu His His Ala Pro Asp Ser
145                 150                 155                 160

Met Val Leu Ala Ala Ser Phe Lys Thr Pro Arg Gln Ala Leu Asp Cys
                165                 170                 175

Leu Leu Ala Gly Cys Gln Ala Ile Thr Leu Pro Leu Asp Val Ala Gln
            180                 185                 190

Gln Met Leu Asn Thr Pro Ala Val Glu Ser Ala Ile Glu Lys Phe Glu
            195                 200                 205

Gln Asp Trp Lys Asn Ala Phe Gly Asn Leu Asn Leu
            210                 215                 220
```

US 10,266,831 B2

RECOMBINANT MICROORGANISMS HAVING A METHANOL ELONGATION CYCLE (MEC)

CROSS REFERENCE TO RELATED APPLICATIONS

This application is a divisional of U.S. application Ser. No. 14/211,415, filed Mar. 14, 2014 (now U.S. Pat. No. 9,518,278), which application claims priority to U.S. Provisional Application Ser. No. 61/785,143, filed Mar. 14, 2013, the disclosures of which are incorporated herein by reference in its entirety.

TECHNICAL FIELD

Metabolically-modified microorganisms and methods of producing such organisms are provided. Also provided are methods of producing chemicals by contacting a suitable substrate with a metabolically-modified microorganism and enzymatic preparations of the disclosure.

BACKGROUND

Acetyl-CoA is a central metabolite key to both cell growth as well as biosynthesis of multiple cell constituents and products, including fatty acids, amino acids, isoprenoids, and alcohols. Typically, the Embden-Meyerhof-Parnas (EMP) pathway, the Entner-Doudoroff (ED) pathway, and their variations are used to produce acetyl-CoA from sugars through oxidative decarboxylation of pyruvate. Similarly, the CBB, RuMP, and DHA pathways incorporate C1 compounds, such as $CO_2$ and methanol, to synthesize sugar-phosphates and pyruvate, which then produce acetyl-CoA through decarboxylation of pyruvate. Thus, in all heterotrophic organisms and those autotrophic organisms that use the sugar-phosphate-dependent pathways for C1 incorporation, acetyl-coA is derived from oxidative decarboxylation of pyruvate, resulting in loss of one molecule of $CO_2$ per molecule of pyruvate. While the EMP route to acetate and ethanol has been optimized, the $CO_2$ loss problem has not been solved due to inherent pathway limitations. Without using a $CO_2$ fixation pathway, such as the Wood-Ljungdahl pathway or the reductive TCA cycle, the waste $CO_2$ leads to a significant decrease in carbon yield. This loss of carbon has a major impact on the overall economy of biorefinery and the carbon efficiency of cell growth.

SUMMARY

For industrial applications, the carbon utilization pathway of the disclosure can be used to improve carbon yield in the production of fuels and chemicals derived from acetyl-CoA, such as, but not limited to, acetate, n-butanol, isobutanol, ethanol and the like. For example, if additional reducing power such as hydrogen or formic acid is provided, the carbon utilization pathway of the disclosure can be used to produce compounds that are more reduced than the substrate, for example, ethanol, 1-butanol, isoprenoids, and fatty acids from sugar.

The disclosure provides a recombinant microorganism comprising a metabolic pathway for the synthesis of acetyl phosphate from methanol, methane or formaldehyde using a pathway comprising an enzyme having fructose-6-phosphoketolase (Fpk) activity and/or xylulose-5-phosphoketolase (Xpk) activity with an acetyl-phosphate yield better than a wild-type or parental organism lacking Fpk and/or Xpk. In one embodiment, the microorganism is a prokaryote or eukaryote. In another embodiment, the microorganism is yeast. In yet another embodiment, the microorganism is a prokaryote. In yet a further embodiment, the microorganism is derived from an E. coli microorganism. In yet a further embodiment, the E. coli is engineered to express a phosphoketolase. In yet another embodiment, the phosphoketolase is Fpk, Xpk or a bifunctional F/Xpk enzyme. In another embodiment of any of the foregoing embodiments, the microorganism is engineered to heterologously expresses one or more of the following enzymes (a) a phosphoketolase (F/Xpk); (b) a transaldolase (Tal); (c) a transketolase (Tkt); (d) a ribose-5-phosphate isomerase (Rpi); (e) a ribulose-5-phosphate epimerase (Rpe); (f) a methanol dehydrogenase (Mdh); (g) a hexulose-6-phosphate synthase (Hps); (h) a hexulose-6-phosphate isomerase (Phi); (i) a dihydroxyacetone synthase (Das); and (j) a fructose-6-phosphate aldolase (Fsa). In another embodiment, the microorganism is engineered to express a phosphoketolase derived from Bifidobaceterium adolescentis. In a further embodiment, the phosphoketolase comprises a sequence that is at least 49% identical to SEQ ID NO:2 and has phosphoketolase activity.

The disclosure also provides a recombinant microorganism comprising a non-$CO_2$-evolving pathway that comprises synthesizing acetyl phosphate using a recombinant metabolic pathway that metabolizes methanol, methane, or formaldehyde with carbon conservation. In one embodiment, the microorganism is a prokaryote or eukaryote. In another embodiment, the microorganism is yeast. In yet another embodiment, the microorganism is a prokaryote. In yet a further embodiment, the microorganism is derived from an E. coli microorganism. In yet a further embodiment, the E. coli is engineered to express a phosphoketolase. In yet another embodiment, the phosphoketolase is Fpk, Xpk or a bifunctional F/Xpk enzyme. In another embodiment of any of the foregoing embodiments, the microorganism is engineered to heterologously expresses one or more of the following enzymes (a) a phosphoketolase (F/Xpk); (b) a transaldolase (Tal); (c) a transketolase (Tkt); (d) a ribose-5-phosphate isomerase (Rpi); (e) a ribulose-5-phosphate epimerase (Rpe); (f) a methanol dehydrogenase (Mdh); (g) a hexulose-6-phosphate synthase (Hps); (h) a hexulose-6-phosphate isomerase (Phi); (i) a dihydroxyacetone synthase (Das); and (j) a fructose-6-phosphate aldolase (Fsa). In another embodiment, the microorganism is engineered to express a phosphoketolase derived from Bifidobaceterium adolescentis. In a further embodiment, the phosphoketolase comprises a sequence that is at least 49% identical to SEQ ID NO:2 and has phosphoketolase activity.

The disclosure also provides a recombinant microorganism comprising a pathway that produces acetyl-phosphate through carbon rearrangement of E4P and/or G3P and metabolism of a carbon source selected from methane, methanol, or formaldehyde. In one embodiment, the microorganism is a prokaryote or eukaryote. In another embodiment, the microorganism is yeast. In yet another embodiment, the microorganism is a prokaryote. In yet a further embodiment, the microorganism is derived from an E. coli microorganism. In yet a further embodiment, the E. coli is engineered to express a phosphoketolase. In yet another embodiment, the phosphoketolase is Fpk, Xpk or a bifunctional F/Xpk enzyme. In another embodiment of any of the foregoing embodiments, the microorganism is engineered to heterologously expresses one or more of the following enzymes (a) a phosphoketolase (F/Xpk); (b) a transaldolase (Tal); (c) a transketolase (Tkt); (d) a ribose-5-phosphate isomerase (Rpi); (e) a ribulose-5-phosphate epimerase (Rpe); (f) a methanol dehydrogenase (Mdh); (g) a hexulose-6-phosphate synthase (Hps); (h) a hexulose-6-phosphate isomerase (Phi); (i) a dihydroxyacetone synthase (Das); and (j) a fructose-6-phosphate aldolase (Fsa). In another embodiment, the microorganism is engineered to express a phosphoketolase derived from *Bifidobaceterium adolescentis*. In one embodiment, the phosphoketolase comprises a sequence that is at least 49% identical to SEQ ID NO:2 and has phosphoketolase activity.

The disclosure also provides a recombinant microorganism expressing enzymes that catalyze the conversion described in (i)-(xi), wherein at least one enzyme or the regulation of at least one enzyme that performs a conversion described in (i)-(xi) is heterologous to the microorganism: (i) the production of acetyl-phosphate and erythrose-4-phosphate (E4P) from fructose-6-phosphate and/or the production of acetyl-phosphate and glyceraldehyde 3-phosphate (G3P) from xylulose 5-phosphate; (ii) the reversible conversion of fructose-6-phosphate and E4P to sedoheptulose 7-phosphate (S7P) and (G3P); (iii) the reversible conversion of S7P and G3P to ribose-5-phosphate and xylulose-5-phosphate; (iv) the reversible conversion of ribose-5-phosphate to ribulose-5-phosphate; (v) the reversible conversion of ribulose-5-phosphate to xylulose-5-phosphate; (vi) the reversible conversion of xylulose-5-phosphate and E4P to fructose-6-phosphate and glyceraldehyde-3-phosphate; (vii) the conversion of formaldehyde and ribulose-5-phosphate to D-arabino-3-Hexulose 6-phosphate; (viii) the reversible conversion of D-arabino-3-Hexulose 6-phosphate to fructose-6-phosphate; (ix) the conversion of formaldehyde and xylulose-5-phosphate to glyceraldehyde-3-phosphate and dihydroxyacetone; (x) the conversion of glyceraldehyde-3-phosphate and dihydroxyacetone to fructose-6-phosphate; and (xi) the conversion of methanol and a oxidized electron acceptor to formaldehyde and a reduced electron acceptor, wherein the microorganism produces acetyl-phosphate, or compounds derived from acetyl-phosphate using a carbon source selected from the group consisting of methanol, methane, and formaldehyde and any combination thereof. In one embodiment, the microorganism is a prokaryote or eukaryote. In another embodiment, the microorganism is yeast. In another embodiment, the microorganism is a prokaryote. In yet a further embodiment, the microorganism is derived from an *E. coli* microorganism. In yet a further embodiment, the *E. coli* is engineered to express a phosphoketolase. In another embodiment, the phosphoketolase is Fpk, Xpk or a bifunctional F/Xpk enzyme. In another embodiment of any of the foregoing embodiments, the microorganism is engineered to heterologously expresses one or more of the following enzymes (a) a phosphoketolase (F/Xpk); (b) a transaldolase (Tal); (c) a transketolase (Tkt); (d) a ribose-5-phosphate isomerase (Rpi); (e) a ribulose-5-phosphate epimerase (Rpe); (f) a methanol dehydrogenase (Mdh); (g) a hexulose-6-phosphate synthase (Hps); (h) a hexulose-6-phosphate isomerase (Phi); (i) a dihydroxyacetone synthase (Das); and (j) a fructose-6-phosphate aldolase (Fsa). In another embodiment, the microorganism is engineered to express a phosphoketolase derived from *Bifidobaceterium adolescentis*. In a further embodiment, the phosphoketolase comprises a sequence that is at least 49% identical to SEQ ID NO:2 and has phosphoketolase activity.

The disclosure also provides a recombinant *E. coli* that produces acetyl-phosphate comprising expression of mdh, act, hps, phi, and f/xpk. In a further embodiment, the microorganism comprises expression of atoB, hbd, crt, ter, and adhE2, and wherein the *E. coli* produces 1-butanol. In yet a further embodiment, the *E. coli* further comprises pta. In still a further embodiment, the *E. coli* further comprises one or more knockouts selected from the group consisting of: ΔgapA, ΔidhA, ΔfrdABCD, ΔadhE, and flack.

The disclosure also provides a recombinant yeast that produces acetyl-phosphate comprising expression of mdh, act, hps, phi, and f/xpk. In a further embodiment, the yeast further expresses atoB, hbd, crt, ter, and adhE2, and wherein the yeast produces 1-butanol. In yet a further embodiment, the yeast further expresses pta. In yet a further embodiment, the yeast further comprises one or more knockouts selected from the group consisting of: Δpdc, Δadh, ΔgapA, and a glycerol dehydrogenase.

The disclosure also provides a recombinant *Bacillus methanolicus* that produces acetyl-phosphate comprising expression of f/xpk. In a further embodiment, the *Bacillus methanolicus* further expresses atoB, hbd, crt, ter, and adhE2, and wherein the *Bacillus methanolicus* produces 1-butanol. In yet a further embodiment, the *Bacillus methanolicus* further expresses pta. In yet a further embodiment, the recombinant *Bacillus methanolicus* further comprises one or more knockouts selected from the group consisting of: Δack, and an acetaldehyde dehydrogenase (acetylating).

The disclosure also provides a recombinant microorganism comprising a metabolic pathway for the synthesis of acetyl phosphate from methanol, methane or formaldehyde using a pathway comprising an enzyme having fructose-6-phosphoketolase (Fpk) activity and/or xylulose-5-phosphoketolase (Xpk) activity and wherein the microorganism produces a metabolite selected from the group consisting of citrate, isocitrate, alpha-ketoglutarate, glutamate and any combination thereof.

In one embodiment, the microorganism is a prokaryote or eukaryote. In another embodiment, the microorganism is yeast. In yet another embodiment, the microorganism is a prokaryote. In yet a further embodiment, the microorganism is derived from an *E. coli* microorganism. In yet a further embodiment, the *E. coli* is engineered to express a phosphoketolase. In yet another embodiment, the phosphoketolase is Fpk, Xpk or a bifunctional F/Xpk enzyme. In another embodiment, the microorganism is engineered to express a phosphoketolase derived from *Bifidobaceterium adolescentis*. In a further embodiment, the phosphoketolase comprises a sequence that is at least 49% identical to SEQ ID NO:2 and has phosphoketolase activity. In yet another embodiment, the recombinant microorganism is engineered to heterologously expresses one or more of the following enzymes: (a) a phosphoketolase (F/Xpk); (b) a transaldolase (Tal); (c) a transketolase (Tkt); (d) a ribose-5-phosphate isomerase (Rpi); (e) a ribulose-5-phosphate epimerase (Rpe); (f) a methanol dehydrogenase (Mdh); (g) a hexulose-6-phosphate synthase (Hps); (h) a hexulose-6-phosphate isomerase (Phi); (i) a dihydroxyacetone synthase (Das); (j) a fructose-6-phosphate aldolase (Fsa); (k) a phosphoenolpyruvate carboxylase (Ppc); (l) an alcohol dehydrogenase (AdhA); (m) a phosphotransacetylase (Pta); (n) an isocitrate dehydrogenase (Icd); (o) a citrate synthase (GltA); and (p) an aconitase (Acn).

The disclosure also provides a recombinant microorganism of any of the foregoing embodiments, wherein the microorganism comprises an acetyl-phosphate (AcP) yield from a C1 carbon source (e.g., methanol, methane or formaldehyde better than 3:1, 2.9:1, 2.8:1, 2.7:1, 2.6:1, 2.5:1 to about 2:1 (C1 carbon source to AcP).

The details of one or more embodiments of the disclosure are set forth in the accompanying drawings and the descrip-

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

FIGS. 6-10 shows various coding sequences for enzymes useful in the methods and compositions of the disclosure.

DETAILED DESCRIPTION

Figure 1:
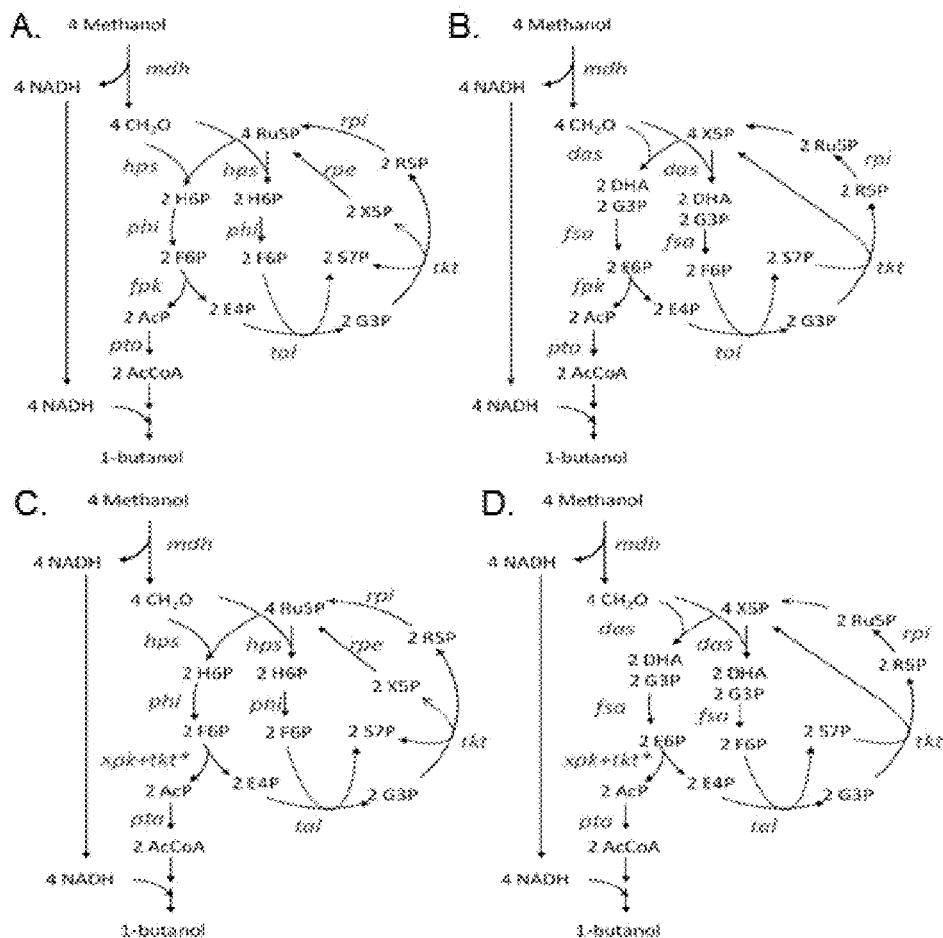
FIG. 1A-D shows four variations of methanol elongation cycle (MEC) converting methanol to acetyl-phosphate (AcP) and then further to 1-butanol. (a) MEC involving hps and phi activity. (b) MEC involving das and fsa activity. (c) MEC involving hps, phi and an xpk/tkt activity. (d) MEC involving a das, fsa, and xpk/tkt activity. Other abbreviations are: F6P, fructose 6-phosphate; E4P: erythrose-4-phosphate; G3P, glyceraldehyde 3-phosphate; DHAP, dihydroxyacetone phosphate; X5P, xylulose 5-phosphate; R5P, ribose 5-phosphate; Ru5P, ribulose 5-phosphate; S7P, sedoheptulose 7-phosphate; Tal, transaldolase; Tkt, transketolase; Rpi, ribose-5-phosphate isomerase; Rpe: ribulose-5-phosphate 3-epimerase; Fpk, Fructose-6-phosphoketolase; Xpk, Xylulose-5-phosphoketolase; Mdh, Methanol dehydrogenase; Hps, hexulose-6-phosphate synthase; Phi, Hexulose-6-phosphate isomerase; Das, dihydroxyacetone synthase; Fsa, Fructose-6-phosphate aldolase; Pta, Phosphotransacetylase; and Ack, acetate kinase.
Figure 2:
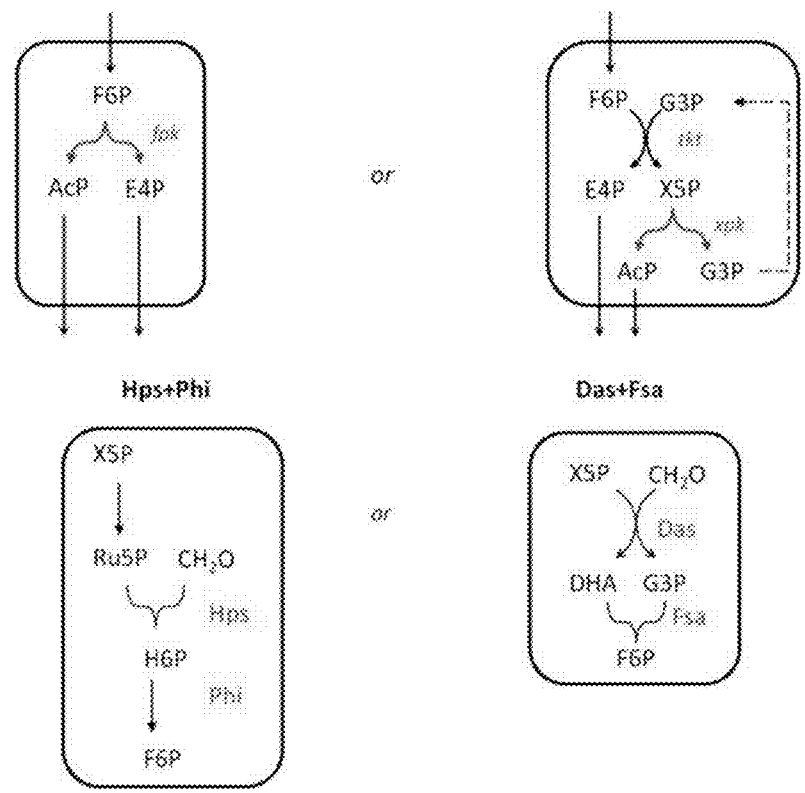
FIG. 2 shows pathways depicting formaldehyde assimilation. Formaldehyde assimilation to F6P can be accomplished by the RuMP enzymes: hps and phi. It can also be accomplished using a modified version of the DHA pathway; das and fsa can also convert a pentose phosphate and formaldehyde to F6P. Phosphoketolase are well known to be able to have X5P or dual F6P/X5P activity. When combined with transketolase, these two variants of phosphoketolase are logically identical.
Figure 3:
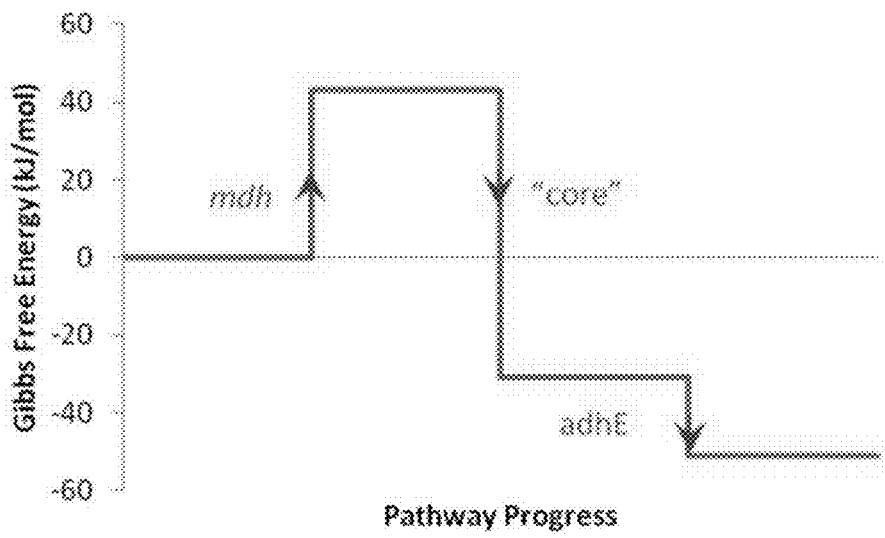
FIG. 3 is a graph depicting the thermodynamics of MEC. The initial oxidation of methanol to formaldehyde provides the main thermodynamic hurdle. However, the core portion of MEC (the conversion of two formaldehydes to AcCoA) is very thermodynamically favorable. The final sequential reduction of acetyl-CoA to ethanol is also thermodynamically favorable. Values were generated using the eQuilibrator website using pH=7.5 and ionic strength at 0.2 Molar.
Figure 4:
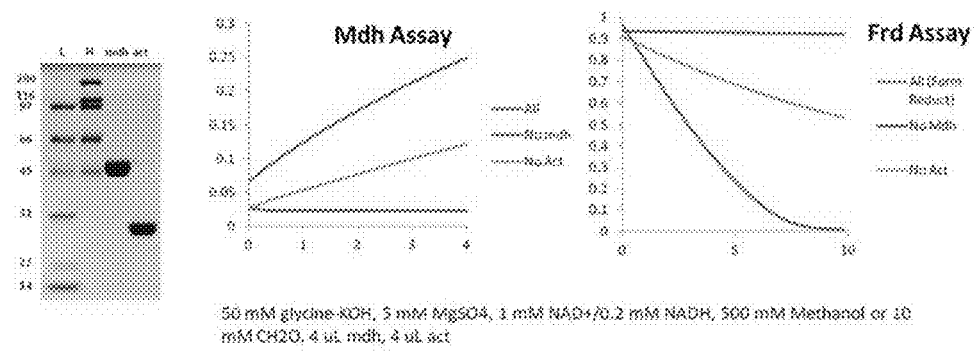
FIG. 4 shows and assay for methanol oxidation. The methanol dehydrogenase gene form *Bacillus methanolicus* is known to be activated by a specific activator production (termed Act). Here, the same enzyme can catalyze the oxidation of methanol and the reduction of formaldehyde using NAD or NADH, respectively. The oxidation of methanol is much slower than the reverse direction, and is driven by large concentration of substrate (500 mM methanol) and quick elimination of product (formaldehyde).
Figure 5:
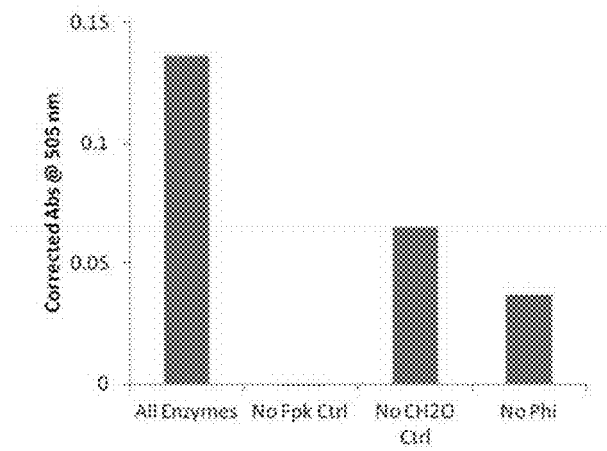
FIG. 5 is a graph showing the in vitro conversion of 2 Formaldehydes to Acetyl-Phosphate. The in vitro conversion of formaldehyde to acetyl-phosphate using the MEC enzymes was measured by the hydroxamate method. An initial amount of R5P was added to start the cycle, with excess amounts of formaldehyde. When all the MEC enzymes were added, a significantly higher conversion to acetyl-phosphate was achieved as compared with the controls.
Figure 11:
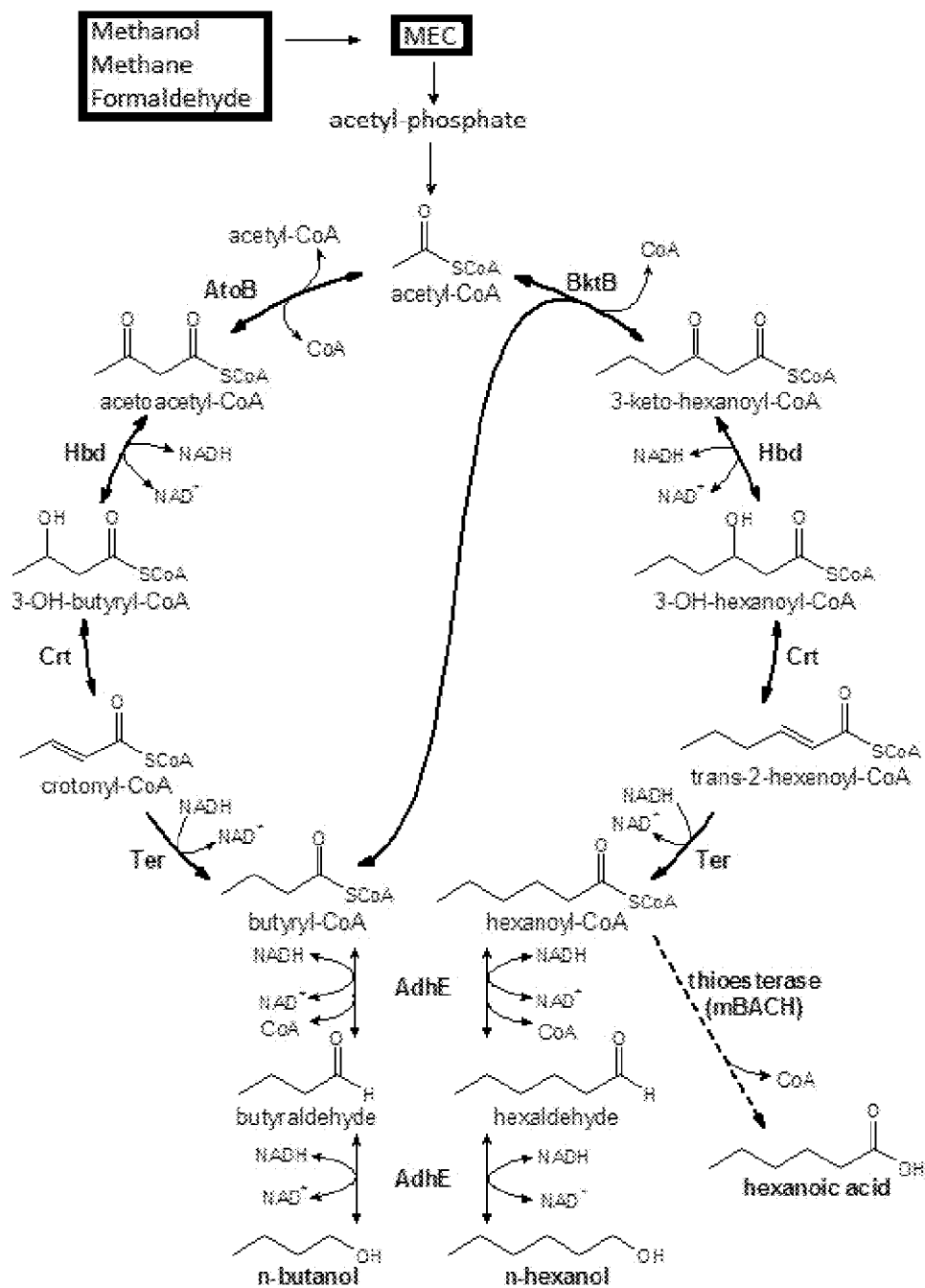
FIGS. 11-12 show general schemes depicting MEC and additional products that can be formed following production of acetyl-phosphate by the MEC pathway.
Figure 12:
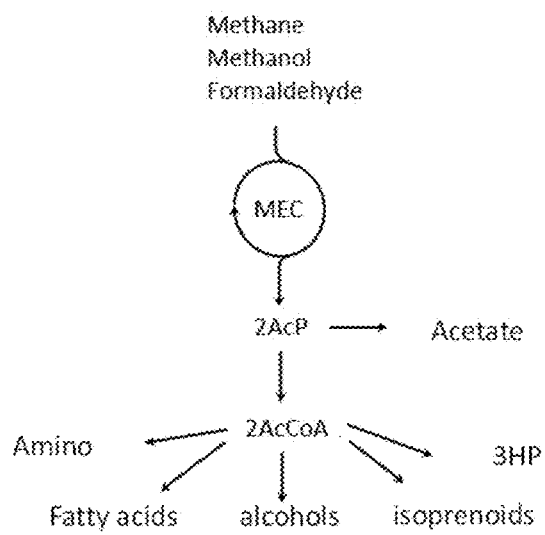
Figure 13:
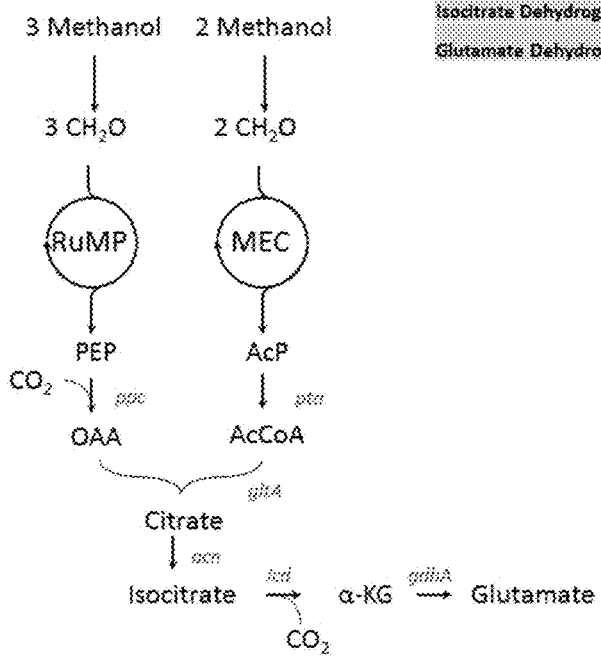
FIG. 13 shows a pathway for the production of citrate, isocitrate and glutamate using acetyl-phosphate produced through the MEC pathway of the disclosure.

As used herein and in the appended claims, the singular forms "a," "and," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

Methylotrophs are microorganisms capable of assimilating methanol into higher carbon molecules essential for cellular growth, such as acetyl-CoA. In the known methylotrophic pathways, methanol is first oxidized to formaldehyde. Formaldehyde can then be assimilated by one of several possible routes such as the RuMP, DHA, or serine pathway. These pathways allow formaldehyde to be converted to sugar-phosphates or pyruvate, which can then feed into central metabolism. However, in the native conversion of methanol to acetyl-CoA, carbon dioxide is always inevitably lost during the decarboxylation of pyruvate.

The disclosure provides methods and compositions to avoid this problem in carbon management, by using a recombinant metabolic pathway to bypass pyruvate oxidation to stoichiometrically convert two methanols into acetyl-CoA. This pathway, termed Methanol Elongation Cycle (MEC), is able to condense two methanol molecules to acetyl-CoA via a series of well-established enzymes. The acetyl-CoA can then be used in a number of pathways, such as the production of bio-alcohol. In the case of 1-butanol production from methanol, the overall pathway is thermodynamically favorable, ATP-independent, and redox balanced. Such a conversion has not been reported before. This pathway represents at 50% improvement in carbon balance over existing pathways and can be used in the conversion of methanol to higher-chain liquid fuels.

The disclosure provides methods and compositions (including cell free systems and recombinant organisms) that provide improved carbon yield compared to naturally occurring methanol utilization pathways. By "improved carbon yield" means that the process results in a conversion of methane, methanol, or formaldehyde to acetyl-phosphate with minimal to no carbon loss (e.g., loss as $CO_2$).

It should be recognized that the disclosure describes the pathway in various embodiments and is schematically depicted in FIG. 1. It will be further recognized the oxidative metabolism may occur after production of acetyl-phosphate of FIG. 1.

In the pathways shown (in FIG. 1), methanol is the input molecule; however, methane and formaldehyde (among others) may also be used in the pathway. A methanol dehydrogenase is used to initiate the metabolism of methanol to acetyl-phosphate. The pathway uses investment of 5 carbon sugar phosphates such as, for example, ribulose-5-phosphate and xylulose-5-phosphate, which reacts with $CH_2O$ to begin a series of reactions involved in non-oxidative carbon rearrangement to regenerate the 5-carbon sugar phosphates and produced acetyl-phosphate. MEC can proceed with a fructose-6-phosphoketolase (Fpk), a xylulose-5-phosphoketolase (Xpk) or bifunctional enzymes that contain both activities. Because of the flexibility of MEC, the pathway can proceed with different combinations of Fpk or Xpk and Tkt, or with different sugar phosphates as the starting molecule. In all these pathways, MEC converts the combination of sugar phosphates and methanol, methane or formaldehyde to AcP without or with minimal carbon loss. AcP can then be converted to acetyl-CoA by acetyltransferase (Pta, Pta variant or homolog thereof), or to acetate by acetate kinase (Ack, Ack variant or homolog thereof). Acetyl-CoA can be converted to alcohols, fatty acids, or other products if additional reducing power is provided. When producing acetyl phosphate from methanol, the MEC pathway converts 4 methanol to 2 acetyl phosphates.

The disclosure provides an in vitro method of producing acetyl-phosphate, acetyl-CoA and chemicals and biofuels that use acetyl-CoA as a substrate. In this embodiment, of the disclosure cell-free preparations can be made through, for example, three methods. In one embodiment, the enzymes of the MEC pathway, as described more fully below, are purchased and mixed in a suitable buffer and a suitable substrate is added and incubated under conditions suitable for acetyl-phosphate production. In another embodiment, one or more polynucleotides encoding one or more enzymes of the MEC pathway are cloned into one or more microorganism under conditions whereby the enzymes are expressed. Subsequently the cells are lysed and the lysed preparation comprising the one or more enzymes derived from the cell are combined with a suitable buffer and substrate (and one or more additional enzymes of the MEC pathway, if needed) to produced acetyl-phosphate from the substrate. Alternatively, the enzymes can be isolated from the lysed preparations and then recombined in an appropriate buffer. In yet another embodiment, a combination of purchased enzymes and expressed enzymes are used to provide a MEC pathway in an appropriate buffer.

For example, to construct an in vitro system, all the MEC enzymes can be acquired commercially or purified by affinity chromatography, tested for activity, and mixed together in a properly selected reaction buffer. The system is ATP- and redox-independent and comprises 6 enzymatic steps that include the following enzymes: (i) an Mdh (methanol dehydrogenase); (ii) an Hps (hexulose-6-phosphate synthase and a Das (dihydroxyacetone synthase) or a Phi (hexulose-6-phosphate isomerase and Fsa (fructose-6-phosphate aldolase; (iii) an Fpk (fructose-6-phosphate phosphoketolase or a Xpk (xylulose-6-phosphate phosphoketolase) and a Tkt (transketolase); (iv) an Rpi (ribose-5-phosphate isomerase); (v) a Tkt (transketolase); and (vi) a Tal (transaldolase).

Using this in vitro system comprising the foregoing 6 enzymatic steps an initial amount of 4 moles of methanol can be converted to 2 moles of AcP (within error) at room temperature after about 1.5 hours.

The disclosure also provides recombinant organisms comprising metabolically engineered biosynthetic pathways that comprise a non-$CO_2$ ATP independent pathway for the production of acetyl-phosphate, acetyl-CoA and/or products derived therefrom.

In one embodiment, the disclosure provides a recombinant microorganism comprising elevated expression of at least one target enzyme as compared to a parental microorganism or encodes an enzyme not found in the parental organism. In another or further embodiment, the microorganism comprises a reduction, disruption or knockout of at least one gene encoding an enzyme that competes with a metabolite necessary for the production of a desired metabolite or which produces an unwanted product. The recombinant microorganism produces at least one metabolite involved in a biosynthetic pathway for the production of, for example, acetyl-phosphate and/or acetyl-CoA. In general, the recombinant microorganisms comprises at least one recombinant metabolic pathway that comprises a target enzyme and may further include a reduction in activity or expression of an enzyme in a competitive biosynthetic pathway. The pathway acts to modify a substrate or metabolic intermediate in the production of, for example, acetyl-phosphate and/or acetyl-CoA. The target enzyme is encoded by, and expressed from, a polynucleotide derived from a suitable biological source. In some embodiments, the polynucleotide comprises a gene derived from a bacterial or yeast source and recombinantly engineered into the microorganism of the disclosure. In another embodiment, the polynucleotide encoding the desired target enzyme is naturally occurring in the organism but is recombinantly engineered to be overexpressed compared to the naturally expression levels.

As used herein, an "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

The term "biosynthetic pathway", also referred to as "metabolic pathway", refers to a set of anabolic or catabolic biochemical reactions for converting (transmuting) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product. The disclosure provides recombinant microorganism having a metabolically engineered pathway for the production of a desired product or intermediate.

Accordingly, metabolically "engineered" or "modified" microorganisms are produced via the introduction of genetic material into a host or parental microorganism of choice thereby modifying or altering the cellular physiology and biochemistry of the microorganism. Through the introduction of genetic material the parental microorganism acquires new properties, e.g. the ability to produce a new, or greater quantities of, an intracellular metabolite. In an illustrative embodiment, the introduction of genetic material into a parental microorganism results in a new or modified ability to produce acetyl-phosphate and/or acetyl-CoA through a non-$CO_2$ evolving and/or non-oxidative pathway for optimal carbon utilization. The genetic material introduced into the parental microorganism contains gene(s), or parts of gene(s), coding for one or more of the enzymes involved in a biosynthetic pathway for the production of acetyl-phosphate and/or acetyl-CoA, and may also include additional elements for the expression and/or regulation of expression of these genes, e.g. promoter sequences.

An engineered or modified microorganism can also include in the alternative or in addition to the introduction of a genetic material into a host or parental microorganism, the disruption, deletion or knocking out of a gene or polynucleotide to alter the cellular physiology and biochemistry of the microorganism. Through the reduction, disruption or knocking out of a gene or polynucleotide the microorganism acquires new or improved properties (e.g., the ability to produce a new or greater quantities of an intracellular metabolite, improve the flux of a metabolite down a desired pathway, and/or reduce the production of undesirable by-products).

An "enzyme" means any substance, typically composed wholly or largely of amino acids making up a protein or polypeptide that catalyzes or promotes, more or less specifically, one or more chemical or biochemical reactions.

As used herein, the term "metabolically engineered" or "metabolic engineering" involves rational pathway design and assembly of biosynthetic genes, genes associated with operons, and control elements of such polynucleotides, for the production of a desired metabolite, such as an acetyl-phosphate and/or acetyl-CoA, higher alcohols or other chemical, in a microorganism. "Metabolically engineered" can further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway. A biosynthetic gene can be heterologous to the host microorganism, either by virtue of being foreign to the host, or being modified by mutagenesis, recombination, and/or association with a heterologous expression control sequence in an endogenous host cell. In one embodiment, where the polynucleotide is xenogenetic to the host organism, the polynucleotide can be codon optimized.

A "metabolite" refers to any substance produced by metabolism or a substance necessary for or taking part in a particular metabolic process that gives rise to a desired metabolite, chemical, alcohol or ketone. A metabolite can be an organic compound that is a starting material (e.g., methanol, methane, formaldehyde etc.), an intermediate in (e.g., acetyl-coA), or an end product (e.g., 1-butanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

A "native" or "wild-type" protein, enzyme, polynucleotide, gene, or cell, means a protein, enzyme, polynucleotide, gene, or cell that occurs in nature.

A "parental microorganism" refers to a cell used to generate a recombinant microorganism. The term "parental microorganism" describes a cell that occurs in nature, i.e. a "wild-type" cell that has not been genetically modified. The term "parental microorganism" also describes a cell that serves as the "parent" for further engineering. For example, a wild-type microorganism can be genetically modified to express or over express a first target enzyme such as a phosphoketolase. This microorganism can act as a parental microorganism in the generation of a microorganism modified to express or over-express a second target enzyme e.g., a transaldolase. In turn, the microorganism can be modified to express or over express e.g., a transketolase and a ribose-5 phosphate isomerase, which can be further modified to express or over express a third target enzyme, e.g., a ribulose-5-phosphate epimerase.

Accordingly, a parental microorganism functions as a reference cell for successive genetic modification events. Each modification event can be accomplished by introducing one or more nucleic acid molecules in to the reference cell. The introduction facilitates the expression or over-expression of one or more target enzyme or the reduction or elimination of one or more target enzymes. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of exogenous polynucleotides encoding a target enzyme in to a parental microorganism.

A "protein" or "polypeptide", which terms are used interchangeably herein, comprises one or more chains of chemical building blocks called amino acids that are linked together by chemical bonds called peptide bonds. A protein or polypeptide can function as an enzyme.

Polynucleotides that encode enzymes useful for generating metabolites (e.g., enzymes such as phosphoketolase, transaldolase, transketolase, ribose-5-phosphate isomerase, ribulose-5-phosphate epimerase) including homologs, variants, fragments, related fusion proteins, or functional equivalents thereof, are used in recombinant nucleic acid molecules that direct the expression of such polypeptides in appropriate host cells, such as bacterial or yeast cells. FIGS. 6-10 provide exemplary polynucleotide sequences encoding polypeptides useful in the methods described herein. It is understood that the addition of sequences which do not alter the encoded activity of a nucleic acid molecule, such as the addition of a non-functional or non-coding sequence, is a conservative variation of the basic nucleic acid.

It is understood that a polynucleotide described above include "genes" and that the nucleic acid molecules described above include "vectors" or "plasmids." For example, a polynucleotide encoding a phosphoketolase can comprise an Fpk gene or homolog thereof, or an Xpk gene or homolog thereof, or a bifunctional F/Xpk gene or homolog thereof. Accordingly, the term "gene", also called a "structural gene" refers to a polynucleotide that codes for a particular polypeptide comprising a sequence of amino acids, which comprise all or part of one or more proteins or enzymes, and may include regulatory (non-transcribed) DNA sequences, such as promoter region or expression control elements, which determine, for example, the conditions under which the gene is expressed. The transcribed region of the gene may include untranslated regions, including introns, 5'-untranslated region (UTR), and 3'-UTR, as well as the coding sequence.

The term "polynucleotide," "nucleic acid" or "recombinant nucleic acid" refers to polynucleotides such as deoxyribonucleic acid (DNA), and, where appropriate, ribonucleic acid (RNA).

The term "expression" with respect to a gene or polynucleotide refers to transcription of the gene or polynucleotide and, as appropriate, translation of the resulting mRNA transcript to a protein or polypeptide. Thus, as will be clear from the context, expression of a protein or polypeptide results from transcription and translation of the open reading frame.

Those of skill in the art will recognize that, due to the degenerate nature of the genetic code, a variety of codons differing in their nucleotide sequences can be used to encode a given amino acid. A particular polynucleotide or gene sequence encoding a biosynthetic enzyme or polypeptide described above are referenced herein merely to illustrate an embodiment of the disclosure, and the disclosure includes polynucleotides of any sequence that encode a polypeptide comprising the same amino acid sequence of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate preferred embodiments of the disclosure.

The disclosure provides polynucleotides in the form of recombinant DNA expression vectors or plasmids, as described in more detail elsewhere herein, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) form.

A polynucleotide of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated polynucleotide molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitution, in some positions it is preferable to make conservative amino acid substitutions.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

The term "recombinant microorganism" and "recombinant host cell" are used interchangeably herein and refer to microorganisms that have been genetically modified to express or over-express endogenous polynucleotides, or to express non-endogenous sequences, such as those included in a vector. The polynucleotide generally encodes a target enzyme involved in a metabolic pathway for producing a desired metabolite as described above, but may also include protein factors necessary for regulation or activity or transcription. Accordingly, recombinant microorganisms described herein have been genetically engineered to express or over-express target enzymes not previously expressed or over-expressed by a parental microorganism. It is understood that the terms "recombinant microorganism" and "recombinant host cell" refer not only to the particular recombinant microorganism but to the progeny or potential progeny of such a microorganism.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, but also intermediate and end product metabolites used in a pathway associated with a metabolically engineered microorganism as described herein. With respect to the MEC pathway described herein, a starting material can be any suitable carbon source including, but not limited to, methanol, methane, formaldehyde etc. Methanol, for example, can be converted to formaldehyde prior to entering the MEC pathway as set forth in FIG. 1.

"Transformation" refers to the process by which a vector is introduced into a host cell. Transformation (or transduction, or transfection), can be achieved by any one of a number of means including electroporation, microinjection, biolistics (or particle bombardment-mediated delivery), or *agrobacterium* mediated transformation.

A "vector" generally refers to a polynucleotide that can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433, which is incorporated herein by reference in its entirety), can also be used. For *E. coli* expression vectors, it is useful to include an *E. coli* origin of replication, such as from pUC, p1P, p1, and pBR.

Thus, recombinant expression vectors contain at least one expression system, which, in turn, is composed of at least a portion of a gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

The disclosure provides methods for the heterologous expression of one or more of the biosynthetic genes or polynucleotides involved in acetyl-phosphate synthesis, acetyl-CoA biosynthesis or other metabolites derived therefrom and recombinant DNA expression vectors useful in the method. Thus, included within the scope of the disclosure are recombinant expression vectors that include such nucleic acids.

Recombinant microorganisms provided herein can express a plurality of target enzymes involved in pathways for the production of acetyl-phosphate, acetyl-CoA or other metabolites derived therefrom from a suitable carbon substrate such as, for example, methanol, methane, formaldehyde and the like. The carbon source can be metabolized to, for example, a desirable sugar phosphate that is metabolized in the MEC pathway of the disclosure. Sources of methanol, methane and formaldehyde are known. Of particular interest is methane gas, which is occurs in nature and is a common by-product waste degradation.

The disclosure demonstrates that the expression or over expression of one or more heterologous polynucleotide or over-expression of one or more native polynucleotides encoding (i) a polypeptide that catalyzes the production of acetyl-phosphate and erythrose-4-phosphate (E4P) from Fructose-6-phosphate; (ii) a polypeptide that catalyzes the conversion of fructose-6-phosphate and E4P to sedoheptulose 7-phosphate (S7P); (iii) a polypeptide the catalyzes the conversion of S7P to ribose-5-phosphate and xylulose-5-phosphate; (iv) a polypeptide that catalyzes the conversion of ribose-5-phosphate to ribulose-5-phosphate; (v) a polypeptide the catalyzes the conversion of ribulose-5-phosphate to xylulose-5-phosphate; (vi) a polypeptide that converts fructose 1,6-biphosphate to fructose-6-phosphate; (vii) a polypeptide that converts ribulose-5-phosphate and formaldehyde to hexulose-6-phosphate; (viii) a polypeptide that converts hexulose-6-phosphate to fructose-6-phosphate; (ix) a polypeptide that converts xylulose-5-phosphate and formaldehyde to dihydroxyacetone and glyceraldehyde-3-phosphate; and (x) a polypeptide that converts dihydroxyacetone and glyceraldehyde-3-phosphate to fructose-6-phosphate. Optionally the recombinant microorganism may further include a polypeptide that converts methanol to formaldehyde; a polypeptide that converts acetyl-phosphate to acetyl-coA, and/or acetyl-coA to 1-butanol. For example, the disclosure demonstrates that with expression of a heterologous a Fpk/Xpk genes in *Escherichia* (e.g., *E. coli*) the production of acetyl-phosphate, acetyl-CoA or other metabolites derived therefrom can be obtained.

Microorganisms provided herein are modified to produce metabolites in quantities and utilize carbon sources more effectively compared to a parental microorganism. In particular, the recombinant microorganism comprises a metabolic pathway for the production of acetyl-phosphate that conserves carbon. By "conserves carbon" is meant that the metabolic pathway that converts a sugar phosphate to acetyl-phosphate has a minimal or no loss of carbon from the starting sugar phosphate to the acetyl-phosphate. For example, in one embodiment, the recombinant microorganism produces a stoichiometrically conserved amount of carbon product from the same number of carbons in the input carbon source (e.g., 2 methanol yields 1 acetyl-phosphate).

Accordingly, the disclosure provides a recombinant microorganisms that produce acetyl-phosphate, acetyl-CoA or other metabolites derived therefrom and includes the expression or elevated expression of target enzymes such as a phosphoketolase (e.g., Fpk, Xpk, or Fpk/Xpk), a transaldolase (e.g., Tal), a transketolase (e.g., Tkt), ribose-5-phosphate isomerase (e.g., Rpi), a ribulose-5-phosphate epimerase (e.g., Rpe), a hexulose-6-phosphate synthase (e.g., Hps), a hexulose-6-phosphate isomerase (e.g., Phi), a dihydroxyacetone synthase (e.g., Das), a fructose-6-phosphate aldolase (e.g., Fsa), a methanol dehydrogenase (e.g., Mdh), or any combination thereof, as compared to a parental microorganism. In some embodiments, where an acetyl-phosphate product is to be further metabolized, the recombinant microorganism can express or over express a phosphotransacetylase (e.g., pta), and optionally may include expression or over expression of an acetate kinase. In addition, the microorganism may include a disruption, deletion or knockout of expression of an alcohol/acetaldehyde dehydrogenase that preferentially uses acetyl-coA as a substrate (e.g. adhE gene), as compared to a parental microorganism. In some embodiments, further knockouts may include knockouts in a lactate dehydrogenase (e.g., ldh) and frdBC. It will be recognized that organism that inherently have one or more (but not all) of the foregoing enzymes, which can be utilized as a parental organism. As described more fully below, a microorganism of the disclosure comprising one or more recombinant genes encoding one or more enzymes above, and may further include additional enzymes that extend the acetyl-phosphate product to acetyl-CoA, which can then be extended to produce, for example, butanol, isobutanol, 2-pentanone and the like.

Accordingly, a recombinant microorganism provided herein includes the elevated expression of at least one target enzyme, such as FpK, Xpk, or F/Xpk. In other embodiments, a recombinant microorganism can express a plurality of target enzymes involved in a pathway to produce acetyl-phosphate, acetyl-CoA or other metabolites derived therefrom as depicted in FIG. 1 from a carbon source such as methanol, methane, formaldehyde and the like. In one embodiment, the recombinant microorganism comprises expression of a heterologous or over expression of an endogenous enzyme selected from a phosphoketolase and either (i) hexulose-6-phosphate synthase and hexulose-6-phosphate isomerase, or (ii) a dihydroxyacetone synthase and a fructose-6-phosphate aldolase. In another embodiment, when the microorganism expresses or overexpress a transketolase (Tkt) and/or a transaldolase (Tal).

As previously noted, the target enzymes described throughout this disclosure generally produce metabolites. In addition, the target enzymes described throughout this disclosure are encoded by polynucleotides. For example, a fructose-6-phosphoketolase can be encoded by an Fpk gene, polynucleotide or homolog thereof. The Fpk gene can be derived from any biologic source that provides a suitable nucleic acid sequence encoding a suitable enzyme having fructose-6-phosphoketolase activity.

Accordingly, in one embodiment, a recombinant microorganism provided herein includes expression of a fructose-6-phosphoketolase (Fpk) as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes acetyl-phosphate and E4P from fructose-6-phosphate. The fructose-6-phosphoketolase can be encoded by a Fpk gene, polynucleotide or homolog thereof. The Fpk gene or polynucleotide can be derived from *Bifidobacterium adolescentis*.

Phosphoketolase enzymes (F/Xpk) catalyze the formation of acetyl-phosphate and glyceraldehyde 3-phosphate or erythrose-4-phosphate from xylulose 5-phosphate or fructose 6-phosphate, respectively. For example, the *Bifidobacterium adolescentis* Fpk and Xpk genes or homologs thereof can be used in the methods of the disclosure.

In addition to the foregoing, the terms "phosphoketolase" or "F/Xpk" refer to proteins that are capable of catalyzing the formation of acetyl-phosphate and glyceraldehyde 3-phosphate or erythrose-4-phosphate from xylulose 5-phosphate or fructose 6-phosphate, respectively, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:2. Additional homologs include: *Gardnerella vaginalis* 409-05 ref|YP_003373859.1| having 91% identity to SEQ ID NO:2; *Bifidobacterium breve* ref|ZP_06595931.1| having 89% to SEQ ID NO:2; *Cellulomonas fimi* ATCC 484 YP_004452609.1 having 55% to SEQ ID NO:2; *Methylomonas methanica* YP_004515101.1 having 50% identity to SEQ ID NO:2; and *Thermosynechococcus elongatus* BP-1] NP_681976.1 having 49% identity to SEQ ID NO:2. The sequences associated with the foregoing accession numbers are incorporated herein by reference.

In another embodiment, a recombinant microorganism provided herein includes elevated expression of methanol dehydrogenase (Mdh) as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes formaldehyde from a substrate that includes methanol. The methanol dehydrogenase can be encoded by a Mdh gene, polynucleotide or homolog thereof. The Mdh gene or polynucleotide can be derived from various microorganisms including *B. methanolicus*.

In addition to the foregoing, the terms "methanol dehydrogenase" or "Mdh" refer to proteins that are capable of catalyzing the formation of formaldehyde from methanol, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:4.

In another embodiment, a recombinant microorganism provided herein includes elevated expression of ribulose-5-phosphate epimerase as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes xylulose 5-phosphate from a substrate that includes ribulose 5-phosphate. The ribulose-5-phosphate epimerase can be encoded by a Rpe gene, polynucleotide or homolog thereof. The Rpe gene or polynucleotide can be derived from various microorganisms including *E. coli*.

In addition to the foregoing, the terms "ribulose 5-phosphate epimerase" or "Rpe" refer to proteins that are capable of catalyzing the formation of xylulose 5-phosphate from ribulose 5-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:6. Additional homologs include: *Shigella boydii* ATCC 9905 ZP_11645297.1 having 99% identity to SEQ ID NO:6; *Shewanella loihica* PV-4 YP_001092350.1 having 87% identity to SEQ ID NO:6; *Nitrosococcus halophilus* Nc4 YP_003526253.1 having 75% identity to SEQ ID NO:6; *Ralstonia eutropha* JMP134 having 72% identity to SEQ ID NO:6; and *Synechococcus* sp. CC9605 YP_381562.1 having 51% identity to SEQ ID NO:6. The sequences associated with the foregoing accession numbers are incorporated herein by reference.

In another embodiment, a recombinant microorganism provided herein includes elevated expression of ribose-5-phosphate isomerase as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes ribulose-5-phosphate from a substrate that includes ribose-5-phosphate. The ribose-5-phosphate isomerase can be encoded by a Rpi gene, polynucleotide or homolog thereof. The Rpi gene or polynucleotide can be derived from various microorganisms including *E. coli*.

In addition to the foregoing, the terms "ribose-5-phosphate isomerase" or "Rpi" refer to proteins that are capable of catalyzing the formation of ribulose-5-phosphate from ribose 5-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:8. Additional homologs include: *Vibrio sinaloensis* DSM 21326 ZP_08101051.1 having 74% identity to SEQ ID NO:8; *Aeromonas media* WS ZP_15944363.1 having 72% identity to SEQ ID NO:8; *Thermosynechococcus elongatus* BP-1 having 48% identity to SEQ ID NO:8; *Lactobacillus suebicus* KCTC 3549 ZP_09450605.1 having 42% identity to SEQ ID NO:8; and *Homo sapiens* AAK95569.1 having 37% identity to SEQ ID NO:8. The sequences associated with the foregoing accession numbers are incorporated herein by reference.

In another embodiment, a recombinant microorganism provided herein includes elevated expression of transaldolase as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes sedoheptulose-7-phosphate from a substrate that includes erythrose-4-phosphate and fructose-6-phosphate. The transaldolase can be encoded by a Tal gene, polynucleotide or homolog thereof. The Tal gene or polynucleotide can be derived from various microorganisms including *E. coli*.

In addition to the foregoing, the terms "transaldolase" or "Tal" refer to proteins that are capable of catalyzing the formation of sedoheptulose-7-phosphate from erythrose-4-phosphate and fructose-6-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:10. Additional homologs include: *Bifidobacterium breve* DSM 20213 ZP_06596167.1 having 30% identity to SEQ ID NO:10; *Homo sapiens* AAC51151.1 having 67% identity to SEQ ID NO:10; *Cyanothece* sp. CCY0110 ZP_01731137.1 having 57% identity to SEQ ID NO:10; *Ralstonia eutropha* JMP134 YP_296277.2 having 57% identity to SEQ ID NO:10; and *Bacillus subtilis* BEST7613 NP_440132.1 having 59% identity to SEQ ID NO:10. The sequences associated with the foregoing accession numbers are incorporated herein by reference.

In another embodiment, a recombinant microorganism provided herein includes elevated expression of transketolase as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes (i) ribose-5-phosphate and xylulose-5-phosphate from sedoheptulose-7-phosphate and glyceraldehyde-3-phosphate; and/or (ii) glyceraldehyde-3-phosphate and fructose-6-phosphate from xylulose-5-phosphate and erythrose-4-phosphate. The transketolase can be encoded by a Tkt gene, polynucleotide or homolog thereof. The Tkt gene or polynucleotide can be derived from various microorganisms including *E. coli*.

In addition to the foregoing, the terms "transketolase" or "Tkt" refer to proteins that are capable of catalyzing the formation of (i) ribose-5-phosphate and xylulose-5-phosphate from sedoheptulose-7-phosphate and glyceraldehyde-3-phosphate; and/or (ii) glyceraldehyde-3-phosphate and fructose-6-phosphate from xylulose-5-phosphate and erythrose-4-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:12. Additional homologs include: *Neisseria meningitidis* M13399 ZP_11612112.1 having 65% identity to SEQ ID NO:12; *Bifidobacterium breve* DSM 20213 ZP_06596168.1 having 41% identity to SEQ ID NO:12; *Ralstonia eutropha* JMP134 YP_297046.1 having 66% identity to SEQ ID NO:12; *Synechococcus elongatus* PCC 6301 YP_171693.1 having 56% identity to SEQ ID NO:12; and *Bacillus subtilis* BEST7613 NP_440630.1 having 54% identity to SEQ ID NO:12. The sequences associated with the foregoing accession numbers are incorporated herein by reference.

In another embodiment, a recombinant microorganism provided herein includes elevated expression of a hexulose-6-phosphate synthase as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes hexulose-6-phosphate from formaldehyde and ribulose-6-phosphate. The hexulose-6-phosphate synthase can be encoded by a Hps gene, polynucleotide or homolog thereof. The Hps gene or polynucleotide can be derived from various microorganisms including *B. subtilis*.

In addition to the foregoing, the terms "hexulose-6-phosphate synthase" or "Hps" refer to proteins that are capable of catalyzing the formation of hexulose-6-phosphate from formaldehyde and ribulose-6-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:14.

In another embodiment, a recombinant microorganism provided herein includes elevated expression of a hexulose-6-phosphate isomerase as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes fructose-6-phosphate from hexulose-6-phosphate. The hexulose-6-phosphate isomerase can be encoded by a Phi gene, polynucleotide or homolog thereof. The Phi gene or polynucleotide can be derived from various microorganisms including *M. Flagettus*.

In addition to the foregoing, the terms "hexulose-6-phosphate isomerase" or "Phi" refer to proteins that are capable of catalyzing the formation of fructose-6-phosphate from hexulose-6-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:16.

In another embodiment, a recombinant microorganism provided herein includes elevated expression of a dihydroxyacetone synthase as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes dihydroxyacetone and glyceraldehyde-3-phosphate from xylulose-5-phosphate and formaldehyde. The dihydroxyacetone synthase can be encoded by a Das gene, polynucleotide or homolog thereof. The Das gene or polynucleotide can be derived from various microorganisms including *C. boindii*.

In addition to the foregoing, the terms "dihydroxyacetone synthase" or "Das" refer to proteins that are capable of catalyzing the formation of dihydroxyacetone and glyceraldehyde-3-phosphate from xylulose-5-phosphate and formaldehyde, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:18.

In another embodiment, a recombinant microorganism provided herein includes elevated expression of a fructose-6-phosphate aldolase as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes fructose-6-phosphate from glyceraldehyde-3-phosphate and dihydroxyacetone. The fructose-6-phosphate aldolase can be encoded by a Fsa gene, polynucleotide or homolog thereof. The Fsa gene or polynucleotide can be derived from various microorganisms including *S. enterica*.

In addition to the foregoing, the terms "fructose-6-phosphate aldolase" or "Fsa" refer to proteins that are capable of catalyzing the formation of fructose-6-phosphate from glyceraldehyde-3-phosphate and dihydroxyacetone, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:20.

In yet another embodiment, a recombinant microorganism provided herein includes elevated expression of a crotonyl-CoA reductase as compared to a parental microorganism. This expression may be combined with the expression or over-expression with other enzymes in the metabolic pathway for the production of n-butanol, isobutanol, butyryl-coA and/or acetone. The microorganism produces a metabolite that includes butyryl-CoA from a substrate that includes crotonyl-CoA. The crotonyl-CoA reductase can be encoded by a ccr gene, polynucleotide or homolog thereof. The ccr gene or polynucleotide can be derived from the genus *Streptomyces*. Alternatively, or in addition to, the microorganism provided herein includes elevated expression of a trans-2-hexenoyl-CoA reductase as compared to a parental microorganism. The microorganism produces a metabolite that includes butyryl-CoA from a substrate that includes crotonyl-CoA. The trans-2-hexenoyl-CoA reductase can also convert trans-2-hexenoyl-CoA to hexanoyl-CoA. The trans-2-hexenoyl-CoA reductase can be encoded by a ter gene, polynucleotide or homolog thereof. The ter gene or polynucleotide can be derived from the genus *Euglena*. The ter gene or polynucleotide can be derived from *Treponema denticola*. The enzyme from *Euglena gracilis* acts on crotonoyl-CoA and, more slowly, on trans-hex-2-enoyl-CoA and trans-oct-2-enoyl-CoA.

Trans-2-enoyl-CoA reductase or TER is a protein that is capable of catalyzing the conversion of crotonyl-CoA to butyryl-CoA, and trans-2-hexenoyl-CoA to hexanoyl-CoA. In certain embodiments, the recombinant microorganism expresses a TER which catalyzes the same reaction as Bcd/EtfA/EtfB from Clostridia and other bacterial species. Mitochondrial TER from *E. gracilis* has been described, and many TER proteins and proteins with TER activity derived from a number of species have been identified forming a TER protein family (see, e.g., U.S. Pat. Appl. 2007/0022497 to Cirpus et al.; and Hoffmeister et al., J. Biol. Chem., 280:4329-4338, 2005, both of which are incorporated herein by reference in their entirety). A truncated cDNA of the *E. gracilis* gene has been functionally expressed in *E. coli*.

TER proteins can also be identified by generally well known bioinformatics methods, such as BLAST. Examples of TER proteins include, but are not limited to, TERs from species such as: *Euglena* spp. including, but not limited to, *E. gracilis*, *Aeromonas* spp. including, but not limited, to *A. hydrophila*, *Psychromonas* spp. including, but not limited to, *P. ingrahamii*, *Photobacterium* spp. including, but not limited, to *P. profundum*, *Vibrio* spp. including, but not limited, to *V. angustum*, *V. cholerae*, *V. alginolyticus*, *V. parahaemolyticus*, *V. vulnificus*, *V. fischeri*, *V. splendidus*, *Shewanella* spp. including, but not limited to, *S. amazonensis*, *S. woodyi*, *S. frigidimarina*, *S. paeleana*, *S. baltica*, *S. denitrificans*, *Oceanospirillum* spp., *Xanthomonas* spp. including, but not limited to, *X. oryzae*, *X. campestris*, *Chromohalobacter* spp. including, but not limited, to *C. salexigens*, *Idiomarina* spp. including, but not limited, to *I. baltica*, *Pseudoalteromonas* spp. including, but not limited to, *P. atlantica*, *Alteromonas* spp., *Saccharophagus* spp. including, but not limited to, *S. degradans*, *S. marine gamma proteobacterium*, *S. alpha proteobacterium*, *Pseudomonas* spp. including, but not limited to, *P. aeruginosa*, *P. putida*, *P. fluorescens*, *Burkholderia* spp. including, but not limited to, *B. phytofirmans*, *B. cenocepacia*, *B. cepacia*, *B. ambifaria*, *B. vietnamensis*, *B. multivorans*, *B. dolosa*, *Methylbacillus* spp. including, but not limited to, *M. flageliatus*, *Stenotrophomonas* spp. including, but not limited to, *S. maltophilia*, *Congregibacter* spp. including, but not limited to, *C. litoralis*, *Serratia* spp. including, but not limited to, *S. proteamaculans*, *Marinomonas* spp., *Xytella* spp. including, but not limited to, *X. fastidiosa*, *Reinekea* spp., *Colweffia* spp. including, but not limited to, *C. psychrerythraea*, *Yersinia* spp. including, but not limited to, *Y. pestis*, *Y. pseudotuberculosis*, *Methylobacillus* spp. including, but not limited to, *M. flagellatus*,

*Cytophaga* spp. including, but not limited to, *C. hutchinsonii*, *Flavobacterium* spp. including, but not limited to, *F. johnsoniae*, *Microscilla* spp. including, but not limited to, *M. marina*, *Polaribacter* spp. including, but not limited to, *P. irgensii*, *Clostridium* spp. including, but not limited to, *C. acetobutylicum*, *C. beijerenckii*, *C. cellulolyticum*, *Coxiella* spp. including, but not limited to, *C. burnetii*.

In addition to the foregoing, the terms "trans-2-enoyl-CoA reductase" or "TER" refer to proteins that are capable of catalyzing the conversion of crotonyl-CoA to butyryl-CoA, or trans-2-hexenoyl-CoA to hexanoyl-CoA and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to either or both of the truncated *E. gracilis* TER or the full length *A. hydrophila* TER.

In yet another embodiment, a recombinant microorganism provided herein includes elevated expression of a butyryl-CoA dehydrogenase as compared to a parental microorganism. This expression may be combined with the expression or over-expression with other enzymes in the metabolic pathway for the production of 1-butanol, isobutanol, acetone, octanol, hexanol, 2-pentanone, and butyryl-coA as described herein above and below. The recombinant microorganism produces a metabolite that includes butyryl-CoA from a substrate that includes crotonyl-CoA. The butyryl-CoA dehydrogenase can be encoded by a bcd gene, polynucleotide or homolog thereof. The bcd gene, polynucleotide can be derived from *Clostridium acetobutylicum*, *Mycobacterium tuberculosis*, or *Megasphaera elsdenii*.

In another embodiment, a recombinant microorganism provided herein includes expression or elevated expression of an acetyl-CoA acetyltransferase as compared to a parental microorganism. The microorganism produces a metabolite that includes acetoacetyl-CoA from a substrate that includes acetyl-CoA. The acetyl-CoA acetyltransferase can be encoded by a thlA gene, polynucleotide or homolog thereof. The thlA gene or polynucleotide can be derived from the genus *Clostridium*.

Pyruvate-formate lyase (Formate acetyltransferase) is an enzyme that catalyzes the conversion of pyruvate to acetyl-coA and formate. It is induced by pfl-activating enzyme under anaerobic conditions by generation of an organic free radical and decreases significantly during phosphate limitation. Formate acetyltransferase is encoded in *E. coli* by pflB. PFLB homologs and variants are known. For examples, such homologs and variants include, for example, Formate acetyltransferase 1 (Pyruvate formate-lyase 1) gi|129879|sp|P09373.2|PFLB_ECOLI(129879); formate acetyltransferase 1 (*Yersinia pestis* CO92) gi|16121663|ref|NP_404976.1|(16121663); formate acetyltransferase 1 (*Yersinia pseudotuberculosis* IP 32953) gi|51595748|ref|YP_069939.1|(51595748); formate acetyltransferase 1 (*Yersinia pestis* biovar Microtus str. 91001) gi|45441037|ref|NP_992576.1|(45441037); formate acetyltransferase 1 (*Yersinia pestis* CO92) gi|115347142|emb|CAL20035.1|(115347142); formate acetyltransferase 1 (*Yersinia pestis* biovar Microtus str. 91001) gi|45435896|gb|AAS61453.1|(45435896); formate acetyltransferase 1 (*Yersinia pseudotuberculosis* IP 32953) gi|51589030|emb|CAH20648.1|(51589030); formate acetyltransferase 1 (*Salmonella enterica* subsp. *enterica* serovar Typhi str. CT18) gi|16759843|ref|NP_455460.1| (16759843); formate acetyltransferase 1 (*Salmonella enterica* subsp. *enterica* serovar Paratyphi A str. ATCC 9150) gi|56413977|ref|YP_151052.1|(56413977); formate acetyltransferase 1 (*Salmonella enterica* subsp. *enterica* serovar Typhi) gi|16502136|emb|CAD05373.1|(16502136); formate acetyltransferase 1 (*Salmonella enterica* subsp. *enterica* serovar Paratyphi A str. ATCC 9150) gi|56128234|gb|AAV77740.1|(56128234); formate acetyltransferase 1 (*Shigella dysenteriae* Sd197) gi|82777577|ref|YP_403926.1|(82777577); formate acetyltransferase 1 (*Shigella flexneri* 2a str. 2457T) gi|30062438|ref|NP_836609.1|(30062438); formate acetyltransferase 1 (*Shigella flexneri* 2a str. 2457T) gi|30040684|gb|AAP16415.1|(30040684); formate acetyltransferase 1 (*Shigella flexneri* 5 str. 8401) gi|110614459|gb|ABF03126.1|(110614459); formate acetyltransferase 1 (*Shigella dysenteriae* Sd197) gi|81241725|gb|ABB62435.1|(81241725); formate acetyltransferase 1 (*Escherichia coli* O157:H7 EDL933) gi|12514066|gb|AAG55388.1|AE005279_8(12514066); formate acetyltransferase 1 (*Yersinia pestis* KIM) gi|22126668|ref|NP_670091.1|(22126668); formate acetyltransferase 1 (*Streptococcus agalactiae* A909) gi|76787667|ref|YP_330335.1|(76787667); formate acetyltransferase 1 (*Yersinia pestis* KIM) gi|21959683|gb|AAM86342.1|AE013882_3(21959683); formate acetyltransferase 1 (*Streptococcus agalactiae* A909) gi|76562724|gb|ABA45308.1|(76562724); formate acetyltransferase 1 (*Yersinia enterocolitica* subsp. *enterocolitica* 8081) gi|123441844|ref|YP_001005827.1| (123441844); formate acetyltransferase 1 (*Shigella flexneri* 5 str. 8401) gi|110804911|ref|YP_688431.1|(110804911); formate acetyltransferase 1 (*Escherichia coli* UTI89) gi|91210004|ref|YP_539990.1|(91210004); formate acetyltransferase 1 (*Shigella boydii* Sb227) gi|82544641|ref|YP_408588.1|(82544641); formate acetyltransferase 1 (*Shigella sonnei* Ss046) gi|74311459|ref|YP_309878.1|(74311459); formate acetyltransferase 1 (*Klebsiella pneumoniae* subsp. *pneumoniae* MGH 78578) gi|152969488|ref|YP_001334597.1| (152969488); formate acetyltransferase 1 (*Salmonella enterica* subsp. *enterica* serovar Typhi Ty2) gi|29142384|ref|NP_805726.1|(29142384) formate acetyltransferase 1 (*Shigella flexneri* 2a str. 301) gi|24112311|ref|NP_706821.1|(24112311); formate acetyltransferase 1 (*Escherichia coli* O157:H7 EDL933) gi|15800764|ref|NP_286778.1|(15800764); formate acetyltransferase 1 (*Klebsiella pneumoniae* subsp. *pneumoniae* MGH 78578) gi|150954337|gb|ABR76367.1|(150954337); formate acetyltransferase 1 (*Yersinia pestis* CA88-4125) gi|149366640|ref|ZP_01888674.1|(149366640); formate acetyltransferase 1 (*Yersinia pestis* CA88-4125) gi|149291014|gb|EDM41089.1|(149291014); formate acetyltransferase 1 (*Yersinia enterocolitica* subsp. *enterocolitica* 8081) gi|122088805|emb|CAL11611.1|(122088805); formate acetyltransferase 1 (*Shigella sonnei* Ss046) gi|73854936|gb|AAZ87643.1|(73854936); formate acetyltransferase 1 (*Escherichia coli* UTI89) gi|91071578|gb|ABE06459.1|(91071578); formate acetyltransferase 1 (*Salmonella enterica* subsp. *enterica* serovar Typhi Ty2) gi|29138014|gb|AAO69575.1|(29138014); formate acetyltransferase 1 (*Shigella boydii* Sb227) gi|81246052|gb|ABB66760.1|(81246052); formate acetyltransferase 1 (*Shigella flexneri* 2a str. 301) gi|24051169|gb|AAN42528.1|(24051169); formate acetyltransferase 1 (*Escherichia coli* O157:H7 str. Sakai) gi|13360445|dbj|BAB34409.1|(13360445); formate acetyltransferase 1 (*Escherichia coli* O157:H7 str. Sakai) gi|15830240|ref|NP_309013.1|(15830240); formate acetyltransferase I (pyruvate formate-lyase 1) (*Photorhabdus luminescens* subsp. *laumondii* TTO1) gi|36784986|emb|CAE13906.1|(36784986); formate acetyltransferase I (pyruvate formate-lyase 1) (*Photorhabdus luminescens* subsp. *laumondii* TTO1) gi|37525558|ref|NP_928902.1|(37525558); formate acetyltransferase (*Staphylococcus aureus* subsp. *aureus* Mu50) gi|14245993|dbj|BAB56388.1|(14245993); formate acetyltransferase (*Staphylococcus aureus* subsp. *aureus* Mu50) gi|15923216|ref|NP_370750.1|(15923216); Formate acetyltransferase (Pyruvate formate-lyase) gi|81706366|sp|Q7A7X6.1|PFLB_STAAN (81706366); Formate acetyltransferase (Pyruvate formate-lyase) gi|81782287|sp|Q99WZ7.1|PFLB_STAAM(81782287); Formate acetyltransferase (Pyruvate formate-lyase) gi|81704726|sp|Q7A1W9.1|PFLB_STAAW(81704726); formate acetyltransferase (*Staphylococcus aureus* subsp. *aureus* Mu3) gi|156720691|dbj|BAF77108.1|(156720691); formate acetyltransferase (*Erwinia carotovora* subsp. *atroseptica* SCRI1043) gi|50121521|ref|YP_050688.1| (50121521); formate acetyltransferase (*Erwinia carotovora* subsp. *atroseptica* SCRI1043) gi|49612047|emb|CAG75496.1|(49612047); formate acetyltransferase (*Staphylococcus aureus* subsp. *aureus* str. Newman) gi|150373174|dbj|BAF66434.1|(150373174); formate acetyltransferase (*Shewanella oneidensis* MR-1) gi|24374439|ref|NP_718482.1|(24374439); formate acetyltransferase (*Shewanella oneidensis* MR-1) gi|24349015|gb|AAN55926.1|AE015730_3(24349015); formate acetyltransferase (*Actinobacillus pleuropneumoniae* serovar 3 str. JL03) gi|165976461|ref|YP_001652054.1| (165976461); formate acetyltransferase (*Actinobacillus pleuropneumoniae* serovar 3 str. JL03) gi|165876562|gb|ABY69610.1|(165876562); formate acetyltransferase (*Staphylococcus aureus* subsp. *aureus* MW2) gi|21203365|dbj|BAB94066.1|(21203365); formate acetyltransferase (*Staphylococcus aureus* subsp. *aureus* N315) gi|13700141|dbj|BAB41440.1|(13700141); formate acetyltransferase (*Staphylococcus aureus* subsp. *aureus* str. Newman) gi|151220374|ref|YP_001331197.1| (151220374); formate acetyltransferase (*Staphylococcus aureus* subsp. *aureus* Mu3) gi|156978556|ref|YP_001440815.1|(156978556); formate acetyltransferase (*Synechococcus* sp. JA-2-3B'a(2-13)) gi|86607744|ref|YP_476506.1|(86607744); formate acetyltransferase (*Synechococcus* sp. JA-3-3Ab) gi|86605195|ref|YP_473958.1|(86605195); formate acetyltransferase (*Streptococcus pneumoniae* D39) gi|116517188|ref|YP_815928.1|(116517188); formate acetyltransferase (*Synechococcus* sp. JA-2-3B'a(2-13)) gi|86556286|gb|ABD01243.1|(86556286); formate acetyltransferase (*Synechococcus* sp. JA-3-3Ab) gi|86553737|gb|ABC98695.1|(86553737); formate acetyltransferase (*Clostridium novyi* NT) gi|118134908|gb|ABK61952.1|(118134908); formate acetyltransferase (*Staphylococcus aureus* subsp. *aureus* MRSA252) gi|49482458|ref|YP_039682.1|(49482458); and formate acetyltransferase (*Staphylococcus aureus* subsp. *aureus* MRSA252) gi|49240587|emb|CAG39244.1| (49240587), each sequence associated with the accession number is incorporated herein by reference.

FNR transcriptional dual regulators are transcription regulators responsive to oxygen content. FNR is an anaerobic regulator that represses the expression of PDHc. Accordingly, reducing FNR will result in an increase in PDHc expression. FNR homologs and variants are known. For examples, such homologs and variants include, for example, DNA-binding transcriptional dual regulator, global regulator of anaerobic growth (*Escherichia coli* W3110) gi|1742191|dbj|BAA14927.1|(1742191); DNA-binding transcriptional dual regulator, global regulator of anaerobic growth (*Escherichia coli* K12) gi|16129295|ref|NP_415850.1|(16129295); DNA-binding transcriptional dual regulator, global regulator of anaerobic growth (*Escherichia coli* K12) gi|1787595|gb|AAC74416.1|(1787595); DNA-binding transcriptional dual regulator, global regulator of anaerobic growth (*Escherichia coli* W3110) gi|89108182|ref|AP 001962.1|(89108182); fumarate/nitrate reduction transcriptional regulator (*Escherichia coli* UTI89) gi|162138444|ref|YP_540614.2|(162138444); fumarate/nitrate reduction transcriptional regulator (*Escherichia coli* CFT073) gi|161486234|ref|NP_753709.2|(161486234); fumarate/nitrate reduction transcriptional regulator (*Escherichia coli* O157:H7 EDL933) gi|15801834|ref|NP_287852.1|(15801834); fumarate/nitrate reduction transcriptional regulator (*Escherichia coli* APEC 01) gi|117623587|ref|YP_852500.1|(117623587); fumarate and nitrate reduction regulatory protein gi|71159334|sp|P0A9E5.1|FNR_ECOLI (71159334); transcriptional regulation of aerobic, anaerobic respiration, osmotic balance (*Escherichia coli* O157:H7 EDL933) gi|12515424|gb|AAG56466.1|AE005372_11(12515424); Fumarate and nitrate reduction regulatory protein gi|71159333|sp|P0A9E6.1|FNR_ECOL6(71159333); Fumarate and nitrate reduction Regulatory protein (*Escherichia coli* CFT073) gi|26108071|gb|AAN80271.1|AE016760_130(26108071); fumarate and nitrate reduction regulatory protein (*Escherichia coli* UTI89) gi|91072202|gb|ABE07083.1|(91072202); fumarate and nitrate reduction regulatory protein (*Escherichia coli* HS) gi|157160845|ref|YP_001458163.1| (157160845); fumarate and nitrate reduction regulatory protein (*Escherichia coli* E24377A) gi|157157974|ref|YP_001462642.1|(157157974); fumarate and nitrate reduction regulatory protein (*Escherichia coli* E24377A) gi|157080004|gb|ABV19712.1|(157080004); fumarate and nitrate reduction regulatory protein (*Escherichia coli* HS) gi|157066525|gb|ABV05780.1|(157066525); fumarate and nitrate reduction regulatory protein (*Escherichia coli* APEC 01) gi|115512711|gb|ABJ00786.1| (115512711); transcription regulator Fnr (*Escherichia coli* O157:H7 str. Sakai) gi|13361380|dbj|BAB35338.1| (13361380) DNA-binding transcriptional dual regulator (*Escherichia coli* K12) gi|16131236|ref|NP_417816.1| (16131236), to name a few, each sequence associated with the accession number is incorporated herein by reference.

An acetoacetyl-coA thiolase (also sometimes referred to as an acetyl-coA acetyltransferase) catalyzes the production of acetoacetyl-coA from two molecules of acetyl-coA. Depending upon the organism used a heterologous acetoacetyl-coA thiolase (acetyl-coA acetyltransferase) can be engineered for expression in the organism. Alternatively a native acetoacetyl-coA thiolase (acetyl-coA acetyltransferase) can be overexpressed. Acetoacetyl-coA thiolase is encoded in *E. coli* by thl. Acetyl-coA acetyltransferase is encoded in *C. acetobutylicum* by atoB. THL and AtoB homologs and variants are known. For examples, such homologs and variants include, for example, acetyl-coa acetyltransferase (thiolase) (*Streptomyces coelicolor* A3(2)) gi|21224359|ref|NP_630138.1|(21224359); acetyl-coa acetyltransferase (thiolase) (*Streptomyces coelicolor* A3(2)) gi|3169041|emb|CAA19239.1|(3169041); Acetyl CoA acetyltransferase (thiolase) (*Alcanivorax borkumensis* SK2)

gi|110834428|ref|YP_693287.1|(110834428); Acetyl CoA acetyltransferase (thiolase) (*Alcanivorax borkumensis* SK2) gi|110647539|emb|CAL17015.1|(110647539); acetyl CoA acetyltransferase (thiolase) (*Saccharopolyspora erythraea* NRRL 2338) gi|133915420|emb|CAM05533.1| (133915420); acetyl-coa acetyltransferase (thiolase) (*Saccharopolyspora erythraea* NRRL 2338) gi|134098403|ref|YP_001104064.1|(134098403); acetyl-coa acetyltransferase (thiolase) (*Saccharopolyspora erythraea* NRRL 2338) gi|133911026|emb|CAM01139.1| (133911026); acetyl-CoA acetyltransferase (thiolase) (*Clostridium botulinum* A str. ATCC 3502) gi|148290632|emb|CAL84761.1|(148290632); acetyl-CoA acetyltransferase (thiolase) (*Pseudomonas aeruginosa* UCBPP-PA14) gi|115586808|gb|ABJ12823.1| (115586808); acetyl-CoA acetyltransferase (thiolase) (*Ralstonia metallidurans* CH34) gi|93358270|gb|ABF12358.1| (93358270); acetyl-CoA acetyltransferase (thiolase) (*Ralstonia metallidurans* CH34) gi|93357190|gb|ABF11278.1|(93357190); acetyl-CoA acetyltransferase (thiolase) (*Ralstonia metallidurans* CH34) gi|93356587|gb|ABF10675.1|(93356587); acetyl-CoA acetyltransferase (thiolase) (*Ralstonia eutropha* JMP134) gi|72121949|gb|AAZ64135.1|(72121949); acetyl-CoA acetyltransferase (thiolase) (*Ralstonia eutropha* JMP134) gi|72121729|gb|AAZ63915.1|(72121729); acetyl-CoA acetyltransferase (thiolase) (*Ralstonia eutropha* JMP134) gi|72121320|gb|AAZ63506.1|(72121320); acetyl-CoA acetyltransferase (thiolase) (*Ralstonia eutropha* JMP134) gi|72121001|gb|AAZ63187.1|(72121001); acetyl-CoA acetyltransferase (thiolase) (*Escherichia coli*) gi|2764832|emb|CAA66099.1|(2764832), each sequence associated with the accession number is incorporated herein by reference.

Butyryl-coA dehydrogenase is an enzyme in the protein pathway that catalyzes the reduction of crotonyl-CoA to butyryl-CoA. A butyryl-CoA dehydrogenase complex (Bcd/EtfAB) couples the reduction of crotonyl-CoA to butyryl-CoA with the reduction of ferredoxin. Depending upon the organism used a heterologous butyryl-CoA dehydrogenase can be engineered for expression in the organism. Alternatively, a native butyryl-CoA dehydrogenase can be overexpressed. Butyryl-coA dehydrogenase is encoded in *C. acetobutylicum* and *M. elsdenii* by bcd. BCD homologs and variants are known. For examples, such homologs and variants include, for example, butyryl-CoA dehydrogenase (*Clostridium acetobutylicum* ATCC 824) gi|15895968|ref|NP_349317.1|(15895968); Butyryl-CoA dehydrogenase (*Clostridium acetobutylicum* ATCC 824) gi|15025744|gb|AAK80657.1|AE007768_11(15025744); butyryl-CoA dehydrogenase (*Clostridium botulinum* A str. ATCC 3502) gi|148381147|ref|YP_001255688.1| (148381147); butyryl-CoA dehydrogenase (*Clostridium botulinum* A str. ATCC 3502) gi|148290631|emb|CAL84760.1|(148290631), each sequence associated with the accession number is incorporated herein by reference in its entirety. BCD can be expressed in combination with a flavoprotein electron transfer protein. Useful flavoprotein electron transfer protein subunits are expressed in *C. acetobutylicum* and *M. elsdenii* by a gene etfA and etfB (or the operon etfAB). ETFA, B, and AB homologs and variants are known. For examples, such homologs and variants include, for example, putative a-subunit of electron-transfer flavoprotein gi|1055221↑gb|AAA95970.1|(1055221); putative b-subunit of electron-transfer flavoprotein gi|1055220|gb|AAA95969.1|(1055220), each sequence associated with the accession number is incorporated herein by reference.

Crotonyl-coA reductase catalyzes the reduction of crotonyl-CoA to butyryl-CoA. Depending upon the organism used a heterologous Crotonyl-coA reductase can be engineered for expression in the organism. Alternatively, a native Crotonyl-coA reductase can be overexpressed. Crotonyl-coA reductase is encoded in *S. coelicolor* by ccr. CCR homologs and variants are known. For examples, such homologs and variants include, for example, crotonyl CoA reductase (*Streptomyces coelicolor* A3(2)) gi|21224777|ref|NP_630556.1|(21224777); crotonyl CoA reductase (*Streptomyces coelicolor* A3(2)) gi|4154068|emb|CAA22721.1|(4154068); crotonyl-CoA reductase (*Methylobacterium* sp. 4-46) gi|168192678|gb|ACA14625.1|(168192678); crotonyl-CoA reductase (*Dinoroseobacter shibae* DFL 12) gi|159045393|ref|YP_001534187.1|(159045393); crotonyl-CoA reductase (*Salinispora arenicola* CNS-205) gi|159039522|ref|YP_001538775.1|(159039522); crotonyl-CoA reductase (*Methylobacterium extorquens* PA1) gi|163849740|ref|YP_001637783.1|(163849740); crotonyl-CoA reductase (*Methylobacterium extorquens* PA1) gi|163661345|gb|ABY28712.1|(163661345); crotonyl-CoA reductase (*Burkholderia ambifaria* AMMD) gi|115360962|ref|YP_778099.1|(115360962); crotonyl-CoA reductase (*Parvibaculum lavamentivorans* DS-1) gi|154252073|ref|YP_001412897.1|(154252073); Crotonyl-CoA reductase (*Silicibacter* sp. TM1040) gi|99078082|ref|YP_611340.1|(99078082); crotonyl-CoA reductase (*Xanthobacter autotrophicus* Py2) gi|154245143|ref|YP_001416101.1|(154245143); crotonyl-CoA reductase (*Nocardioides* sp. JS614) gi|119716029|ref|YP_922994.1|(119716029); crotonyl-CoA reductase (*Nocardioides* sp. JS614) gi|119536690|gb|ABL81307.1|(119536690); crotonyl-CoA reductase (*Salinispora arenicola* CNS-205) gi|157918357|gb|ABV99784.1|(157918357); crotonyl-CoA reductase (*Dinoroseobacter shibae* DFL 12) gi|157913153|gb|ABV94586.1|(157913153); crotonyl-CoA reductase (*Burkholderia ambifaria* AMMD) gi|115286290|gb|ABI91765.1|(115286290); crotonyl-CoA reductase (*Xanthobacter autotrophicus* Py2) gi|154159228|gb|ABS66444.1|(154159228); crotonyl-CoA reductase (*Parvibaculum lavamentivorans* DS-1) gi|154156023|gb|ABS63240.1|(154156023); crotonyl-CoA reductase (*Methylobacterium radiotolerans* JCM 2831) gi|170654059|gb|ACB23114.1|(170654059); crotonyl-CoA reductase (*Burkholderia graminis* C4D1M) gi|170140183|gb|EDT08361.1|(170140183); crotonyl-CoA reductase (*Methylobacterium* sp. 4-46) gi|168198006|gb|ACA19953.1|(168198006); crotonyl-CoA reductase (*Frankia* sp. EAN1pec) gi|158315836|ref|YP_001508344.1|(158315836), each sequence associated with the accession number is incorporated herein by reference in its entirety.

In yet other embodiment, in addition to any of the foregoing and combinations of the foregoing, additional genes/enzymes may be used to produce a desired product. For example, the following table provide enzymes that can be combined with the MEC pathway enzymes for the production of 1-butanol:

| Enzyme | Exemplary Gene(s) | 1-butanol | Exemplary Organism |
| --- | --- | --- | --- |
| Ethanol Dehydrogenase | adhE | – | *E. coli* |
| Lactate Dehydrogenase | ldhA | – | *E. coli* |
| Fumarate reductase | frdB, frdC, or frdBC | – | *E. coli* |
| Oxygen transcription regulator | fnr | – | *E. coli* |
| Phosphate acetyltransferase | pta | – | *E. coli* |
| Formate acetyltransferase | pflB | – | *E. coli* |
| acetyl-coA acetyltransferase | atoB | + | *C. acetobutylicum* |
| acetoacetyl-coA thiolase | thl, thlA, thlB | + | *E. coli*, *C. acetobutylicum* |
| 3-hydroxybutyryl-CoA dehydrogenase | hbd | + | *C. acetobutylicum* |
| crotonase | crt | + | *C. acetobutylicum* |
| butyryl-CoA dehydrogenase | bcd | + | *C. acetobutylicum*, *M. elsdenii* |
| electron transfer flavoprotein | etfAB | + | *C. acetobutylicum*, *M. elsdenii* |
| aldehyde/alcohol dehydrogenase (butyral-dehyde dehydrogenase/butanol dehydrogenase) | adhE2 bdhA/bdhB aad | + | *C. acetobutylicum* |
| crotonyl-coA reductase | ccr | + | *S. coelicolor* |
| trans-2-enoyl-CoA reductase | Ter | + | *T. denticola*, *F. succinogenes* |

\* knockout or a reduction in expression are optional in the synthesis of the product, however, such knockouts increase various substrate intermediates and improve yield.

In addition, and as mentioned above, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

In some instances "isozymes" can be used that carry out the same functional conversion/reaction, but which are so dissimilar in structure that they are typically determined to not be "homologous". For example, tktB is an isozyme of tktA, talA is an isozyme of talB and rpiB is an isozyme of rpiA.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which can also be referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

The disclosure provides accession numbers for various genes, homologs and variants useful in the generation of recombinant microorganism described herein. It is to be understood that homologs and variants described herein are exemplary and non-limiting. Additional homologs, variants and sequences are available to those of skill in the art using various databases including, for example, the National Center for Biotechnology Information (NCBI) access to which is available on the World-Wide-Web.

Culture conditions suitable for the growth and maintenance of a recombinant microorganism provided herein are described in the Examples below. The skilled artisan will recognize that such conditions can be modified to accommodate the requirements of each microorganism. Appropriate culture conditions useful in producing a acetyl-phosphate, acetyl-CoA or other metabolites derived therefrom including, but not limited to 1-butanol, n-hexanol, 2-pentanone and/or octanol products comprise conditions of culture medium pH, ionic strength, nutritive content, etc.; temperature; oxygen/$CO_2$/nitrogen content; humidity; light and other culture conditions that permit production of the compound by the host microorganism, i.e., by the metabolic action of the microorganism. Appropriate culture conditions are well known for microorganisms that can serve as host cells.

It is understood that a range of microorganisms can be modified to include a recombinant metabolic pathway suitable for the production of n-butanol, n-hexanol and octanol. It is also understood that various microorganisms can act as "sources" for genetic material encoding target enzymes suitable for use in a recombinant microorganism provided herein.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt ([NaCl]); and extreme (hyper) thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, Micrococcus, others) (2) low G+C group (*Bacillus*, Clostridia, *Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) Bacteroides, Flavobacteria; (7) Chlamydia; (8) Green sulfur bacteria; (9) Green non-sulfur bacteria (also anaerobic phototrophs); (10) Radioresistant micrococci and relatives; and (11) Thermotoga and Thermosipho thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The disclosure includes recombinant microorganisms that comprise at least one recombinant enzymes of the MEC pathway set forth in FIG. 1. For example, chemoautotrophs, photoautotroph, and cyanobacteria can comprise native F/Xpk enzymes, accordingly, overexpressing FPK, XPK, or F/Xpk by tying expression to a non-native promoter can produce metabolite to drive the MEC pathway when combined with the other appropriate enzymes of FIG. 1. Additional enzymes can be recombinantly engineered to further optimize the metabolic flux, including, for example, balancing ATP, NADH, NADPH and other cofactor utilization and production.

In another embodiment, a method of producing a recombinant microorganism that comprises optimized carbon utilization including a MEC pathway to convert methanol, methane or formaldehyde to acetyl-phosphate, acetyl-CoA or other metabolites derived therefrom including, but not limited to, 1-butanol, 2-pentanone, isobutanol, n-hexanol and/or octanol is provided. The method includes transforming a microorganism with one or more recombinant polynucleotides encoding polypeptides selected from the group consisting of a phosphoketolase (e.g., Fpk, Xpk, or Fpk/Xpk), a transaldolase (e.g., Tal), a transketolase (e.g., Tkt), ribose-5-phosphate isomerase (e.g., Rpi), a ribulose-5-phosphate epimerase (e.g., Rpe), a hexulose-6-phosphate synthase (e.g., lips), a hexulose-6-phosphate isomerase (e.g., Phi), a dihydroxyacetone synthase (e.g., Das), a fructose-6-phosphate aldolase (e.g., Fsa), a methanol dehydrogenase (e.g., Mdh), a keto thiolase or acetyl-CoA acetyltransferase activity, hydroxybutyryl CoA dehydrogenase activity, crotonase activity, crotonyl-CoA reductase or butyryl-CoA dehydrogenase activity, trans-enoyl-CoA reductase and alcohol dehydrogenase activity.

In another embodiment, as mentioned previously, a recombinant organism as set forth in any of the embodiments above, is cultured under conditions to express any/all of the enzymatic polypeptide and the culture is then lysed or a cell free preparation is prepared having the necessary enzymatic activity to carry out the pathway set forth in FIG. 1 and/or the production of a 1-butanol, isobutanol, n-hexanol, octanol, 2-pentanone among other products.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"), each of which is incorporated herein by reference in its entirety.

Examples of protocols sufficient to direct persons of skill through in vitro amplification methods, including the polymerase chain reaction (PCR), the ligase chain reaction (LCR), Q□-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13:563-564.

Improved methods for cloning in vitro amplified nucleic acids are described in Wallace et al., U.S. Pat. No. 5,426,039.

Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The invention is illustrated in the following examples, which are provided by way of illustration and are not intended to be limiting.

EXAMPLES

To construct an in vitro system, all the MEC enzymes were acquired commercially or purified by affinity chromatography, tested for activity, and mixed together in a properly selected reaction buffer. AcP concentration is measured using an end-point colorimetric hydroxamate method.

After demonstrating the feasibility of the pathway using in vitro enzymatic systems, the pathway was engineered into *Escherichia coli*. Xylose was used because it avoids the complication of various glucose-mediated regulations, including the use of phosphotransferase system for transport. In order to engineer a preliminary pathway for xylose in *E. coli*, two enzymes were overexpressed: F/Xpk (encoded by f/xpk from *Bifidobacterium adolescentis*) and Fbp (encoded by *E. coli* fbp). Other enzymes were natively expressed in *E. coli* under the experimental conditions. The genes encoding these two enzymes were cloned on a high copy plasmid (pIB4) under the control of the PLlacO-1 IPTG-inducible promoter. The plasmid was transformed into three *E. coli* strains: JCL16 [wild type], JCL166[ΔldhA, ΔadhE, Δfrd], and JCL 118 [ΔldhA, ΔadhE, Δfrd, ΔpflB]. The latter two strains were used to avoid pathways competing. The expression of F/Xpk and Fbp was demonstrated by protein electrophoresis and their activities were confirmed by enzyme assays. After an initial aerobic growth phase for cell growth, high cell density cells were harvested and re-suspended in anaerobic minimal medium with xylose at a final $OD_{600}$ of 9. Anaerobic conditions were used to avoid the oxidation of acetate through the TCA cycle. HPLC was used for monitoring xylose consumption and organic acids formation. The wild-type host (JCL16) produced a mixture of lactate, formate, succinate, and acetate from xylose, and the yield on acetate was quite low at about 0.4 acetates produced per xylose consumed, indicating that EMP and other fermentative pathways out-competed the synthetic pathway. By removing several fermentative pathways by the Δldh, ΔadhE, and Δfrd knockouts in JCL166, the yield was increased to 1.1 acetate/xylose consumed. After further deleting pflB in JCL118, the yield reach the highest level of 2.2 acetates/xylose consumed, approaching the theoretical maximum of 2.5 mole of acetate/mole of xylose. Some succinate remained, presumably due to succinate dehydrogenase left over from the aerobic growth phase.

One useful enzyme in the pathway is the irreversible Fpk/Xpk which can split F6P or xylulose-5-phosphate into AcP and E4P or G3P, respectively. This class of enzymes has been well-characterized in heterofermentative pathways from Lactobacillae and Bifidobacteria. In Lactobacillae, glucose is first oxidized and decarboxylated to form $CO_2$, reducing power, and xylulose-5-phosphate, which is later split to AcP and G3P. Xpks have also been found in *Clostridium acetobutylicum* where up to 40% of xylose is degraded by the phosphoketolase pathway. Bifidobacteria, utilizes the Bifid Shunt, which oxidizes two glucoses into two lactates and three acetates. This process yields increase the ATP yield to 2.5 ATP/glucose. In both variants G3P continues through the oxidative EMP pathway to form pyruvate. Thus these pathways are still oxidative and are not able to directly convert glucose to three two-carbon compounds. For the pathway to function effectively, Fpk/Xpk and Fbp are simultaneously expressed. However, since Fbp is a gluconeogenic enzyme, it is typically not active in the presence of glucose. Thus, although these organisms have all the genes necessary for the pathway, it is unlikely that the pathway is functional in these organisms in the presence of glucose.

Enzyme abbreviations and EC no. are listed in Table A. Table A: Enzyme abbreviations and EC numbers:

| Name | Abbrev. | EC# | Verified Source |
|---|---|---|---|
| FB6-Phosphoketolase 1a | Fpk | 4.1.2.22 | *B. adolescentis*\* |
| X5P-Phosphoketolase 1b | Xpk | 4.1.2.9 | *L. plantarum* |
| Transaldolase 2 | Tal | 2.2.1.2 | *E. coli* |
| Transketolase 3 | Tkt | 2.2.1.1 | *E. coli* |
| Triose Phosphate Isomerase 6 | Tpi | 5.3.1.1 | *E. coli* |
| Fructose 1,6 Bisphosphatase 8 | Fbp | 3.1.3.11 | *E. coli* |
| Fructose 1,6 bisphosphate Aldolase 7 | Fba | 4.1.2.13 | *E. coli* |
| Ribose-5-phosphate isomerase 4 | Rpi | 5.3.1.6 | *E. coli* |
| Ribulose-3-phosphate epimerase 5 | Rpe | 5.1.3.1 | *E. coli* |
| Glucokinase | Glk | 2.7.1.2 | *E. coli* |
| Glucose-6-phosphate Dehydrogenase | Zwf | 1.1.1.49 | *E. coli* |
| Phosphoglucose isomerase | Pgi | 5.3.1.9 | *E. coli* |
| Acetate Kinase | Ack | 2.7.2.1 | *E. coli* |
| Hexulose-6-phosphate synthase | Hps | 4.1.2.43 | *M. capsulatus* |
| Hexulose 6 phosphate isomerase | Phi | 5.3.1.27 | *M. Capsulatus* |
| Dihydroxyacetone synthase (formaldehyde transketolase) | Das | 2.2.1.3 | *C. boindii* |
| Phosphotransacetylase | Pta | 1.3.1.8 | *E. coli* |
| Methanol dehydrogenase | Mdh | 1.1.99.37 | *B. Methanolicus* |

Thermodynamics of MEC enzymes. The change in standard Gibbs free energy ($\Delta rG'^\circ$ in kJ/mol) for each step was calculated using eQuilibrator with pH=7.5 and ionic strength=0.2 M to represent *E. coli's* cytosolic environment. All values were obtained using the difference of the standard Gibbs free energy of formation between the products and reactants. Since standard state is set at 1 M for all reactants (including water), some of the values do not correspond with experimentally verified data.

Combination of the underlying F/Xpk pathway with the Dihydroxyacetone (DHA) pathway. The F/Xpk pathway can be combined with the DHA pathway, which is analogous to the RuMP pathway for assimilation of formaldehyde. The pathways are shown in FIG. 1. This pathway includes the action of the gene fructose-6-phosphate aldolase (fsa) which has been characterized from *E. coli*. Though the native activity of this enzyme was reported to have a high $K_m$, recent design approaches have improved affinity towards DHA. The overall pathway from two methanol to ethanol is favorable with a $\Delta rG'^\circ=-68.2$ kJ/mol.

Construction of In vivo pathways. For the in vivo production of acetate from xylose, the plasmid pIB4 was made using pZE12 as the vector, F/Xpk from *B. adolenscentis* and Fbp from *E. coli* (JCL16 gDNA). The strains JCL16, JCL166, and JCL118 were constructed (see, e.g., Int'l Patent Publication No. WO 2012/099934). This was done using the P1 phage transduction method with the Keio collection as the template for single-gene knockouts. The strains JCL166 and JCL118 were transformed with pIB4. Single colonies were grown in LB medium overnight and inoculated into fresh LB+1% xylose culture the next day. After reaching an OD=0.4-0.6, the strains were induced with 0.1 mM IPTG. After overnight induction, the cells were concentrated tenfold and resuspended anaerobically in M9 1% xylose. A small portion of the induced cells was extracted for HIS-tag purification to verify the activity of F/Xpk and Fbp, and the rest was incubated anaerobically overnight for acetate production. The final mixture was spin down at 14,000 rpm, and a diluted supernatant was run on HPLC to measure xylose and organic acid concentration.

Phosphoketolase in Nature. Phosphoketolase have been known to exist in many bacteria such as Bifidobacteria for decades. Bifidobacteria make up a large portion of the beneficial flora in human's stomach, are used in the fermentation of various foods from yogurt to kimchi, and are even sold in a dehydrated pill form. These bacteria contain a unique pathway that can ferment sugars to a mixture of lactate and acetate. By using the F6P/X5P phosphoketolase enzyme, they are able to obtain more ATP than other fermentative pathways at 2.5 ATP/glucose.

Certain embodiments of the invention have been described. It will be understood that various modifications may be made without departing from the spirit and scope of the invention. Other embodiments are within the scope of the following claims. Chemoautotrophs, photoautotroph, cyanobacteria overexpress FPK, XPK, tied to non-native promoter.

What is claimed is:

1. A recombinant prokaryote or yeast microorganism comprising a metabolic pathway for the synthesis of acetyl phosphate from methanol, methane or formaldehyde, wherein the microorganism is engineered to express the following enzymes: (a) a phosphoketolase (F/Xpk); (b) a transaldolase (Tal); (c) a transketolase (Tkt); (d) a ribose-5-phosphate isomerase (Rpi); (e) a ribulose-5-phosphate epimerase (Rpe); (f) a methanol dehydrogenase (Mdh); (g) a hexulose-6-phosphate synthase (Hps); (h) a hexulose-6-phosphate isomerase (Phi); (i) a dihydroxyacetone synthase (Das); and (j) a fructose-6-phosphate aldolase (Fsa), wherein at least one enzyme is heterologous to the microorganism, and wherein said microorganism has an acetyl-phosphate yield better than a wild-type or parental organism lacking Fpk and/or Xpk.

2. The recombinant microorganism of claim 1, wherein the microorganism is derived from an *E. coli* microorganism.

3. The recombinant microorganism of claim 1, wherein the microorganism is further engineered to express a phosphotransacetylase.

4. The recombinant microorganism of claim 1, wherein the phosphoketolase comprises a sequence that is at least 49% identical to SEQ ID NO:2 and has phosphoketolase activity.

5. The recombinant microorganism of claim 1, wherein the microorganism is *E. coli* comprising a genotype mdh, hps, phi and f/xpk.

6. The recombinant microorganism of claim 1, wherein the pathway produces acetyl phosphate through carbon rearrangement of erythrose-4-phosphate (E4P) and/or glyceraldehyde-3-phosphate (G3P) and metabolism of a carbon source selected from methane, methanol, or formaldehyde.

7. The recombinant microorganism of claim 6, wherein the microorganism is derived from an *E. coli* microorganism.

8. The recombinant microorganism of claim 7, wherein the *E. coli* is engineered to express an Fpk, Xpk or a bifunctional F/Xpk phosphoketolase.

9. The recombinant microorganism of claim 8, wherein the microorganism is further engineered to express a phosphotransacetylase.

10. The recombinant microorganism of claim 8, wherein the phosphoketolase comprises a sequence that is at least 49% identical to SEQ ID NO:2 and has phosphoketolase activity.

* * * * *